US009512204B2

(12) United States Patent
Maynard et al.

(10) Patent No.: US 9,512,204 B2
(45) Date of Patent: Dec. 6, 2016

(54) HUMANIZED PERTUSSIS ANTIBODIES AND USES THEREOF

(71) Applicants: Board of Regents, The University of Texas System, Austin, TX (US); Synthetic Biologics, Inc., Rockville, MD (US)

(72) Inventors: Jennifer Maynard, Austin, TX (US); Annalee Nguyen, Austin, TX (US); Eduardo Padlan, Rockville, MD (US); Ellen Wagner, Austin, TX (US)

(73) Assignees: BOARD OF REGENTS, THE UNIVERSITY OF TEXAS SYSTEM, Austin, TX (US); SYNTHETIC BIOLOGICS, INC., Rockville, MD (US)

( * ) Notice: Subject to any disclaimer, the term of this patent is extended or adjusted under 35 U.S.C. 154(b) by 0 days.

(21) Appl. No.: 14/675,514

(22) Filed: Mar. 31, 2015

(65) Prior Publication Data

US 2015/0353628 A1    Dec. 10, 2015

Related U.S. Application Data

(60) Provisional application No. 61/973,141, filed on Mar. 31, 2014, provisional application No. 62/046,403, filed on Sep. 5, 2014.

(51) Int. Cl.
| | |
|---|---|
| *A61K 39/40* | (2006.01) |
| *C07K 16/12* | (2006.01) |
| *A61K 45/06* | (2006.01) |
| *A61K 39/00* | (2006.01) |

(52) U.S. Cl.
CPC ........... *C07K 16/1225* (2013.01); *A61K 39/40* (2013.01); *A61K 45/06* (2013.01); *A61K 2039/507* (2013.01); *C07K 2317/14* (2013.01); *C07K 2317/24* (2013.01); *C07K 2317/56* (2013.01); *C07K 2317/76* (2013.01); *C07K 2317/92* (2013.01); *C07K 2317/94* (2013.01)

(58) Field of Classification Search
CPC ........... C07K 16/1225; C07K 2317/24; C07K 2317/76; C07K 2317/94; C07K 2317/55; C07K 2317/622; C07K 2317/14; C07K 2317/56; C07K 2317/92; A61K 2039/507; A61K 39/40; A61K 45/06
See application file for complete search history.

(56) References Cited

U.S. PATENT DOCUMENTS

| | | | |
|---|---|---|---|
| 6,884,879 | B1 | 4/2005 | Baca et al. |
| 8,653,243 | B2 | 2/2014 | Maynard et al. |
| 2007/0237779 | A1 | 10/2007 | Ledbetter et al. |
| 2014/0193401 | A1 | 7/2014 | Maynard et al. |

FOREIGN PATENT DOCUMENTS

EP    0320866 A2    6/1989

OTHER PUBLICATIONS

"1B7 Product Information" sheet from the NIBSC, NISBC code 99/506. (Dated Oct. 4, 2008).
AbYsis Distribution Report for Kabat L65, printout from www.bioinf.org.uk/abysis/searches/distributions/distributions.html (last visited May 28, 2015).
Almagro & Fransson, Frontiers in Bioscience (2008); 13:1619-33.
Antoine, R. et al., "Roles of the disulfide bond and the carboxy-terminal region of the S1 subunit in the assembly and biosynthesis of pertussis toxin", Infection and Immunity 58(6):1518-1526, (Jun. 1990).
Bartoloni, A. et al., "Mapping of a protective epitope of pertussis toxin by in vitro refolding of recombinant fragments", Nature Biotechnology 6:709-712, (Jun. 1988).
Bruss, J.B. et al., "Protective effects of pertussis immunoglobulin (P-IGIV) in the aerosol challenge model", Clinical and Diagnostic Laboratory Immunology 6(4):464-470, (Jul. 1999).
Bruss, J.B. et al., "Quantitative priming with inactivated pertussis toxoid vaccine in the aerosol challenge model", Infection and Immunity 70(8):4600-4608, (Aug. 2002).
Bruss, J.B. et al., "Treatment of severe pertussis: a study of the safety and pharmacology of intravenous pertussis immunoglobulin", The Pediatric Infectious Disease Journal 18(6):505-511, (Jun. 1999).
Burnette, W.N. et al., "Pertussis toxin S1 mutant with reduced enzyme activity and a conserved protective epitope", Science 242:72-74, (1988).
Cherry, J.D., et al., (1998). A search for serologic correlates of immunity to Bordetella pertussis cough illnesses. Vaccine. 16: 1901-1906.
Cieplak, W. et al., "Identification of a region in the S1 subunit of pertussis toxin that is required for enzymatic activity and that contributes to the formation of a neutralizing antigenic determinant", Proc Natl Acad Sci U S A. 85: 4667-4671, (1988).
Corada et al., Blood, (2001); 97:1679-84.
Felici, F., et al., "Mimicking of discontinuous epitopes by phage-displayed peptides, II. Selection of clones recognized by a protective monoclonal antibody against the Bordetella pertussis toxin from phage peptide libraries", Gene 128:21-27, (1993).
Granstrom, M. et al., "Specific immunoglobulin for treatment of whooping cough", Lancet 338:1230-1233, (1991).
Hausman, S.Z. et al., "Use of pertussis toxin encoded by ptx genes from Bordetella bronchiseptica to model the effects of antigenic drift of pertussis toxin on antibody neutralization", Infection and Immunity 68(6):3763-3767, (2000).
Hazes, B. et al., "Crystal structure of the pertussis toxin-ATP complex: a molecular sensor", J. Mol Biol. 258:661-671, (1996).
Hellwig, S.M. et al., "Crucial role of antibodies to pertactin in Bordetella pertussis immunity", J. Infect Dis. 188:738-742, (2003).
Jadhav, S.S. et al., "Composition of acellular pertussis and combination vaccines: a general review", Biologicals 27:105-110, (1999).
Kamachi, K. et al., "Development of safer pertussis DNA vaccine expressing non-toxic C180 polypeptide of pertussis toxin S1 subunit", Vaccine 25:1000-1006, (2007).

(Continued)

*Primary Examiner* — Padma V Baskar
(74) *Attorney, Agent, or Firm* — Mintz Levin Cohn Ferris Glovsky and Popeo, P.C.

(57) ABSTRACT

The present invention relates to humanized antibodies which bind the *pertussis* toxin protein and their use as therapeutic agents. In particular, the present invention is directed to improved humanized 1B7 and 11E6 antibodies which bind the *pertussis* toxin protein.

5 Claims, 21 Drawing Sheets

(56) References Cited

OTHER PUBLICATIONS

Kamachi, K. et al., "DNA vaccine encoding pertussis toxin S1 subunit induces protection against Bordetella pertussis in mice", Vaccine 21:4609-4615, (2003).
Kaslow, H.R. et al., "Detection of antibodies inhibiting the ADP-ribosyltransferase activity of pertussis toxin in human serum", Journal of Clinical Microbiology 30(6):1380-1387, (1992).
Kenimer, J.G. et al., "Monoclonal antibodies to pertussis toxin: utilization as probes of toxin function", Hybridoma 8:37-51, (1989).
Kim, K.J. et al. "Epitopes on the S1 subunit of pertussis toxin recognized by monoclonal antibodies", Infection and Immunity 57(3):944-950, (1989).
Kortemme, T. et al., "A simple physical model for binding energy hot spots in protein-protein complexes", Proc. Natl. Acad. Sci. 99(22):14116-14121, (2002).
Kortemme, T. et al., "Computational alanine scanning of protein-protein interfaces", Sciences STKE 219:1-8, (2004).
Krueger, K.M. et al., "Assignment of functional domains involved in ADP-ribosylation and B-oligomer binding within the carboxyl terminus of the 51 subunit of pertussis toxin", Infection and Immunity 62(5):2071-2078, (May 1994).
Kwak & Yoon, J Immunol Meth (1996); 191:49-54.
Mayrose, I. et al., "Epitope mapping using combinatorial phage-display libraries: a graph-based algorithm", Nucleic Acids Research 35(1):69-78, (2007).
Padlan et al. "Identification of specificity-determining residues in antibodies." Faseb J (1995) 9:133-139. (http://www.fasebj.org/content/9/1/133.full.pdf).
Padlan et al., (1991) Mol Immunol 28:489-498.
Padlan, E.A. Adv Prot Chem 49:57-133; (1996).
Pai et al., Recent Pat Antiinfect Drug Disc., (Jan. 2009);4(1):1-17.
Pizza, M. et al., "Mutants of pertussis toxin suitable for vaccine development", Science 246(4929):497-500, Oct. 27, 1989.
Pootong et al., Asian Pac JAllergy Immunol (2007);25:37-45.
Raupach, B. et al., "Elucidation of linear epitopes of pertussis toxin using overlapping synthetic decapeptides: identification of a human B-cell determinant in the S1 subunit indicative of acute infections", Microbial Pathogenesis 17:213-226, (1994).
Rieber, N. et al., "Differences of humoral and cellular immune response to an acellular pertussis booster in adolescents with a whole cell or acellular primary vaccination", Vaccine 26:6929-6935, (2008).
Sato, H. et al., "Comparison of pertussis toxin (PT)-neutralizing activities and mouse-protective activities of anti-PT mouse monoclonal antibodies", Infection and Immunity 59(10):3832-3835, (Oct. 1991).
Sato, H. et al., "Effect of monoclonal antibody to pertussis toxin on toxin activity", Infection and Immunity, 55(4):909-915, (1987).
Sato, H. et al., "Monoclonal antibody against pertussis toxin: effect on toxin activity and pertussis infections", Infection and Immunity 46(2):422-428, (1984).
Sato, H. et al., "Protective activities in mice of monoclonal antibodies against pertussis toxin", Infection and Immunity 58(10):3369-3374, (1990).
Sato, Y. et al., "Separation and purification of the hemagglutinins from Bordetella pertussis", Infection and Immunity 41(1):313-320, (1983).
Smith, M.J. et al., "Monoclonal antibody 11E10, which neutralizes shiga toxin type 2 (Stx2), recognizes three regions on the Stx2 A subunit, blocks the enzymatic action of the toxin in vitro, and alters the overall cellular distribution of the toxin", Infection and Immunity 77(7):2730-2740, (May 2009).
Storsaeter, J. et al. "Levels of anti-pertussis antibodies related to protection after household exposure to Bordetella pertussis", Vaccine 16(20):1907-1916, (1998).
Sutherland, J.N., et al., Characterization of a key neutralizing epitope on pertussis toxin recognized by monoclonal antibody 1B7. *Biochemistry*, (2009). Vol: p. 11982-11993.
Weiss, A.A. et al., "Tn5-induced mutations affecting virulence factors of Bordetella pertussis", Infection and Immunity 42(1):33-41, (1983).
Williamson & Matthews, FEMS Immunology and Medical Microbiology (1999); 23:313-19.
Witvliet, M.H. et al., "Binding of pertussis toxin to eucaryotic cells and glycoproteins", Infection and Immunity 57(11):3324-3330,( Nov. 1989).

21A

Antibody Serum Concentration

21B

Antibody Half-Life

US 9,512,204 B2

HUMANIZED PERTUSSIS ANTIBODIES AND USES THEREOF

CROSS-REFERENCES TO RELATED APPLICATIONS

This application claims the benefit of U.S. Provisional Appl. No. 61/973,141, filed Mar. 31, 2014, and U.S. Provisional Appl. No. 62/046,403, filed Sep. 5, 2014, the content of each of which is incorporated herein by reference in its entirety and for all purposes.

STATEMENT AS TO RIGHTS TO INVENTIONS MADE UNDER FEDERALLY SPONSORED RESEARCH OR DEVELOPMENT

This invention was made with government support under Grant No. R21 AI066239 awarded by the National Institutes of Health. The Government has certain rights in the invention.

REFERENCE TO A "SEQUENCE LISTING," A TABLE, OR A COMPUTER PROGRAM LISTING APPENDIX SUBMITTED AS AN ASCII FILE

The Sequence Listing written in file T9333-522001WO_ST25.TXT, created on Mar. 31, 2015, 26,452 bytes, machine format IBM-PC, MS Windows operating system, is hereby incorporated by reference.

FIELD OF THE INVENTION

The present invention relates, in part, to humanized antibodies which bind the *pertussis* toxin protein and their use as therapeutic agents. In particular, the present invention is directed to, in part, humanized antibodies derived from murine antibodies 1B7 and 11E6 which bind the *pertussis* toxin protein.

BACKGROUND

*Bordetella pertussis* (*B. pertussis*) is a gram-negative bacterium that infects the upper respiratory tract, causing uncontrollable, violent coughing. According to the World Health Organization, *B. pertussis* infection causes an estimated 300,000 deaths worldwide each year, primarily among young, unvaccinated infants. Infants with *pertussis* often require hospitalization in pediatric intensive care units, and their treatments frequently involve mechanical ventilation. *Pertussis* in adults generally leads to a chronic cough referred to as the "cough of 100 days." The incidence of *pertussis* is increasing due to exposures of unvaccinated and under-vaccinated individuals including infants who are not yet fully vaccinated, individuals whose immunity has diminished over time, and asymptomatic carriers.

Recent news reports throughout the United States indicate that the *pertussis* vaccine introduced in the 1990s does not provide long-term protection. There is no approved treatment for *pertussis*. Antibiotic treatments do not have a major effect on the course of *pertussis*, because while the treatment can eliminate the *B. pertussis* bacteria from the respiratory tract, it does not neutralize the *pertussis* toxin protein. Accordingly, there remains a need for more effective therapies against *pertussis*.

Further, in the developing world, access to the existing *pertussis* vaccine, however flawed, is inconsistent and often difficult.

Naturally occurring antibodies are multimeric proteins that contain four polypeptide chains. Two of the polypeptide chains are called heavy chains (H chains), and two of the polypeptide chains are called light chains (L chains). The immunoglobulin heavy and light chains are connected by an interchain disulfide bond. The immunoglobulin heavy chains are connected by interchain disulfide bonds. A light chain consists of one variable region ($V_L$) and one constant region ($C_L$). The heavy chain consists of one variable region ($V_H$) and at least three constant regions ($CH_1$, $CH_2$ and $CH_3$). The variable regions determine the specificity of the antibody. Each variable region comprises three hypervariable regions also known as complementarity determining regions (CDRs) flanked by four relatively conserved framework regions (FRs). The three CDRs, referred to as $CDR_1$, $CDR_2$, and $CDR_3$, contribute to the antibody binding specificity. Naturally occurring antibodies have been used as starting material for engineered antibodies, such as humanized antibodies.

Antibodies that bind the *pertussis* toxin protein have been developed, but the effectiveness of these antibodies in patients is either minimal or unclear. There remains a need for improved antibodies against the *pertussis* toxin protein with increased efficacy and reduced sides effects to be used as therapeutics.

SUMMARY

Accordingly, in various aspects, the present invention is directed to one or more humanized antibodies that bind to and/or neutralize a *pertussis* toxin protein and the uses of the same in the treatment or prevention of *pertussis*.

In one aspect, the present invention is directed to a humanized 1B7 antibody that binds a *pertussis* toxin protein. The humanized 1B7 antibody includes an immunoglobulin heavy chain variable region and an immunoglobulin light chain variable region. In various embodiments, the humanized 1B7 antibody includes an immunoglobulin heavy chain variable region comprising an amino acid sequence selected from SEQ ID NO:1, SEQ ID NO:2, SEQ ID NO:3, SEQ ID NO:4, SEQ ID NO:5, and SEQ ID NO:6, and an immunoglobulin light chain variable region comprising an amino acid sequence selected from SEQ ID NO:7, SEQ ID NO:8, SEQ ID NO:9, SEQ ID NO:10, SEQ ID NO:11, and SEQ ID NO:12.

In another aspect, the present invention is directed to a humanized 11E6 antibody that binds a *pertussis* toxin protein. The humanized 11E6 antibody includes an immunoglobulin heavy chain variable region comprising an amino acid sequence selected from SEQ ID NO:13, SEQ ID NO:14, SEQ ID NO:15, SEQ ID NO:16, SEQ ID NO:17, and SEQ ID NO:18, and an immunoglobulin light chain variable region comprising an amino acid sequence selected from SEQ ID NO:19, SEQ ID NO:20, SEQ ID NO:21, SEQ ID NO:22, SEQ ID NO:23, and SEQ ID NO:24.

In various embodiments, the humanized 1B7 and 11E6 antibodies show improved properties. In an embodiment, the humanized 1B7 antibody binds the *pertussis* toxin protein with a $K_D$ of less than about 3 nM, or about 2 nM, or about 1 nM, or about 0.5 nM. In another embodiment, the humanized 11E6 antibody binds the *pertussis* toxin protein with a $K_D$ of less than about 12 nM, or about 10 nM, or about 8 nM, or about 6 nM, or 4 nM, or 2 nM, or about 1 nM, or about 0.5 nM.

In various embodiments, the present invention also provides nucleic acids, expression vectors, host cells, and methods for making the humanized 1B7 and 11E6 antibodies. The present invention also provides pharmaceutical compositions comprising the humanized 1B7 and/or 11E6 antibodies.

In one aspect, the method of the invention involves treating a patient with *Bordetella pertussis*, comprising administering to the patient the humanized 1B7 antibody and/or the humanized 11E6 antibody, or pharmaceutical compositions including the antibody or antibodies. In an embodiment, the humanized 1B7 antibody and the humanized 11E6 antibody are co-administered to the patient producing synergistic effects. In another embodiment, the method includes administering to the patient the humanized 1B7 antibody and/or the humanized 11E6 antibody, along with antimicrobial agents. In a further embodiment, the method of the invention is directed to preventing *Bordetella pertussis* infection in a subject by administering to the subject the humanized 1B7 antibody and/or the humanized 11E6 antibody, or pharmaceutical compositions including the antibody or antibodies.

In some embodiments, the method of the invention involves preventing the onset of *pertussis* by preventatively administering the humanized 1B7 antibody and/or the humanized 11E6 antibody, or pharmaceutical compositions including the antibody or antibodies for a patient, including an infant that has yet to be vaccinated.

In one embodiment, the method of the invention comprises reducing white blood cell count in the patient. In another embodiment, the method of the invention comprises reducing the duration and/or the frequency of cough in the patient. In a further embodiment, the method of the invention comprises reducing the levels of the *Bordetella pertussis* in the nasopharynx and the lung of the patient. In another embodiment, the method of the invention neutralizes the *pertussis* toxin protein.

In another aspect, the method of the invention involves treating a patient with *Bordetella parapertussis*, comprising administering to the patient the humanized 1B7 antibody and/or the humanized 11E6 antibody, or pharmaceutical compositions including the antibody or antibodies. In another aspect, the method of the invention is directed to preventing *Bordetella parapertussis* infection in a subject by administering to the subject the humanized 1B7 antibody and/or the humanized 11E6 antibody, or pharmaceutical compositions including the antibody or antibodies.

Other aspects and embodiments of the invention will be apparent from the following detailed description and examples.

DESCRIPTION OF THE DRAWINGS

FIG. 6A shows thermal unfolding for the hu11E6 antibody (hu11E6-15x). The top line corresponds to 10 uM hu11E6-15x, the second line from the top corresponds to 20 uM hu11E6-15x, the second line from the bottom corresponds to 5 uM hu11E6-15x, and the bottom line corresponds to PBS. FIG. 6B shows thermal unfolding for the hu1B7 antibody. The top line corresponds to 20 uM hu1B7, the second line from the top corresponds to 10 uM hu1B7, the second line from the bottom corresponds to 5 uM hu1B7, and the bottom line corresponds to PBS. FIG. 6C shows thermal unfolding for the m11E6 antibody. The top line corresponds to 3 uM m11E6, the second line from the top corresponds to 1.5 uM m11E6, the second line from the bottom corresponds to 0.75 uM m11E6, and the bottom line corresponds to PBS. FIG. 6D shows thermal unfolding for the m1B7 antibody. The top line corresponds to 3 uM m1B7, the second line from the top corresponds to 1.5 uM m1B7, the second line from the bottom corresponds to 0.75 uM m1B7, and the bottom line corresponds to PBS.

DETAILED DESCRIPTION

Figure 1:
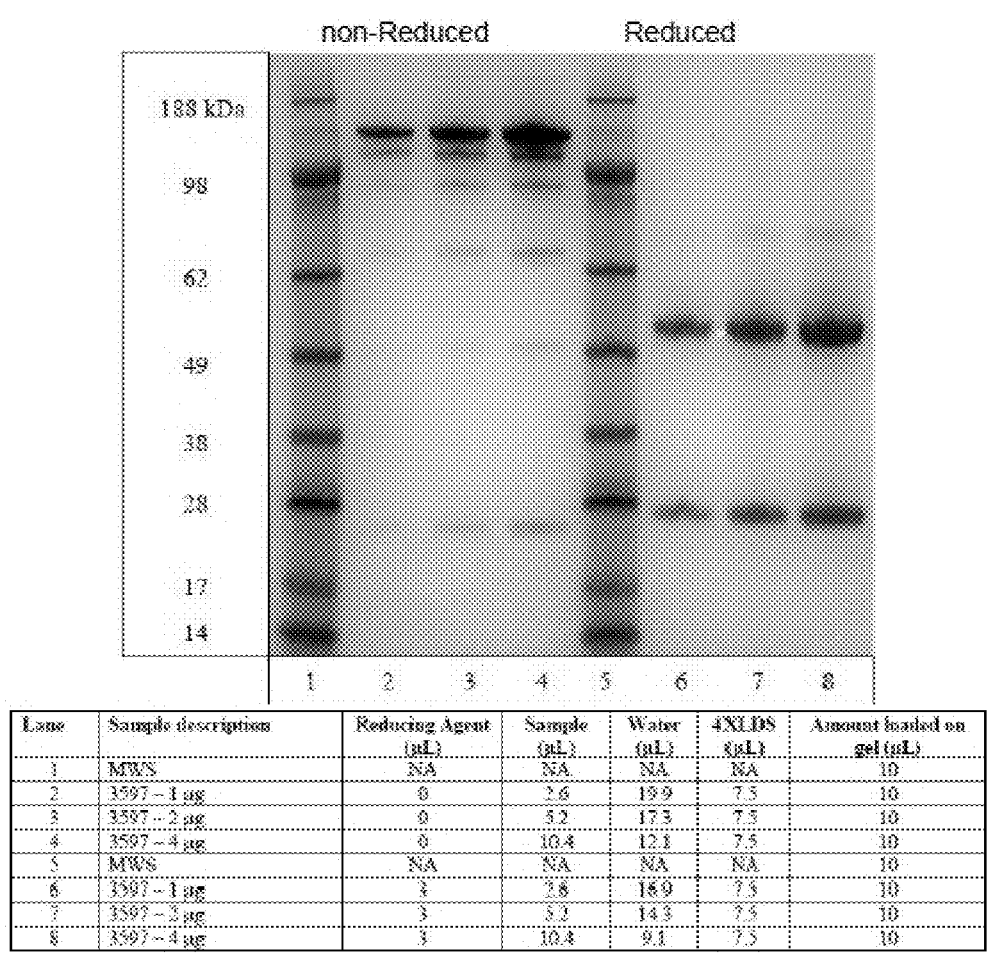
FIG. 1 shows a SDS PAGE gel of a humanized hu1B7 antibody under reducing and non-reducing conditions.

The present invention is based, in part, on the discovery of humanized 1B7 and 11E6 antibodies that exhibit improved biological activities. Because of the binding and/or neutralizing activity of these antibodies against the *pertussis* toxin protein, they are useful for treating patients infected with the *Bordetella pertussis* bacteria. The disclosed antibodies are engineered to target the *pertussis* toxin protein with high specificity while causing minimal side effects in patients. Furthermore, the disclosed antibodies exhibit enhanced stability and long in vivo half-lives. Various features and aspects of the invention are discussed in more detail below.

As used herein, unless otherwise indicated, the term "antibody" means an intact antibody (e.g., an intact monoclonal antibody) or antigen-binding fragment of an antibody (e.g., an antigen-binding fragment of a monoclonal antibody), including an intact antibody or antigen-binding fragment that has been modified, engineered or chemically conjugated, or that is a human antibody. Examples of antibodies that have been modified or engineered are chimeric antibodies, humanized antibodies, and multispecific antibodies (e.g., bispecific antibodies). Examples of antigen-binding fragments include Fab, Fab', F(ab')$_2$, Fv, single chain antibodies (e.g., scFv), minibodies and diabodies. An antibody conjugated to a toxin moiety is an example of a chemically conjugated antibody.

Antibodies that Bind the *Pertussis* Toxin Protein

In one aspect, the present invention is directed to a humanized 1B7 antibody and a humanized 11E6 antibody that bind a *pertussis* toxin protein. In various embodiments, a humanized antibody is a non-human antibody that has been altered to increase its similarity to a human antibody. In some embodiments, a humanized antibody is a genetically engineered antibody in which at least one CDR (or functional fragment thereof) from a non-human, e.g. mouse, antibody ("donor antibody", which can also be rat, hamster or other non-human species) is grafted onto a human antibody ("acceptor antibody"). In some embodiments, more than one mouse CDR is grafted (e.g., all six mouse CDRs are grafted). The sequence of the acceptor antibody can be, for example, a mature human antibody sequence (or fragment thereof), a consensus sequence of a human antibody sequence (or fragment thereof), or a germline region sequence (or fragment thereof). Thus, in some embodiments, a humanized antibody may be an antibody having one or more CDRs from a donor antibody and variable region framework (FR). The FR may form part of a constant region within a human antibody.

In addition, in order to retain high binding affinity, amino acids in the human acceptor sequence may be replaced by the corresponding amino acids from the donor sequence, for example where: (1) the amino acid is in a CDR; (2) the amino acid is in the human framework region (e.g., the amino acid is immediately adjacent to one of the CDR's). See, U.S. Pat. Nos. 5,530,101 and 5,585,089, incorporated herein by reference, which provide detailed instructions for construction of humanized antibodies. Indeed, this selection of residues in, for example, the human framework region is often central to a humanized antibodies desirability. Although humanized antibodies often incorporate all six CDRs (e.g., as defined by Kabat, but often also including hypervariable loop H1 as defined by Chothia) from a mouse antibody, they can also be made with fewer mouse CDRs and/or less than the complete mouse CDR sequence (e.g. a functional fragment of a CDR).

In various embodiments, the humanized light chain variable region is fused to a light chain constant region (e.g. human kappa or a lambda light chain). In various embodiments, the humanized heavy chain variable region is fused to a heavy chain constant region, including various allotypes and isotypes of each. For example, the heavy chain constant region can be derived from any immunoglobulin type (e.g. IgG, IgM, IgA, IgD, or IgE). In some embodiments, IgG is used. For IgG, the constant region can come from IgG1, IgG2, IgG3, or IgG4. In some embodiments, IgG1 is used. Moreover, there are many isotypes of each IgG that can be chosen, some are naturally occurring and some are derivatives of naturally occurring isotypes. The type of IgG that is chosen will determine the effector functions of the antibody (e.g. opsonophagocytosis, complement fixation, etc.).

In one aspect, the present invention is directed to a humanized 1B7 antibody that binds a *pertussis* toxin protein, and comprises an immunoglobulin heavy chain variable region and an immunoglobulin light chain variable region. The immunoglobulin heavy chain variable region comprises an amino acid sequence selected from:

1B7:

(SEQ ID NO: 1)
QVQLQQPGSELVRPGASVKLSCKASGYKFTSYWMHWVKQRPGQGLEWIG

NIFPGSGSTNYDEKFNSKATLTVDTSSNTAYMQLSSLTSEDSAVYYCTR

WLSGAYFDYWGQGTTVTVSS

```
cdr1B7:
                                      (SEQ ID NO: 2)
QVQLVQSGAEVKKPGASVKVSCKASGYKFTSYWMHWVRQAPGQGLEWIG

NIFPGSGSTNYDEKFNSRVTLTVDTSTSTAYMELSSLRSEDTAVYYCTR

WLSGAYFDYWGQGTTVTVSS abb1B7:
                                      (SEQ ID NO: 3)
QVQLVQSGAEVKKPGASVKVSCKASGYKFTSYWMHWVRQAPGQGLEWIG

NIFPGSGSTNYAQKFQGRVTLTVDTSTSTAYMELSSLRSEDTAVYYCTR

WLSGAYFDYWGQGTTVTVSS sdr1B7:
                                      (SEQ ID NO: 4)
QVQLVQSGAEVKKPGASVKVSCKASGYKFTSYWMHWVRQAPGQGLEWIG

NIFPGSGSTNYAQKFQGRVTLTVDTSTSTAYMELSSLRSEDTAVYYCTR

WLSGAYFDYWGQGTTVTVSS fra1B7:
                                      (SEQ ID NO: 5)
QVQLQQSGSELKKPGASVKISCKASGYKFTSYWMHWVKQRPGQGLEWIG

NIFPGSGSTNYDEKFNSRVTLTVDTSTSTAYMELSSLRSEDTAVYYCTR

WLSGAYFDYWGQGTTLTVSS ven1B7:
                                      (SEQ ID NO: 6)
QVQLVQSGAELVKPGASVKLSCKASGYKFTSYWMHWVKQRPGQGLEWIG

NIFPGSGSTNYDEKFNSKATLTVDTSTSTAYMELSSLRSEDTAVYYCTR

WLSGAYFDYWGQGTTLTVSS
```

The immunoglobulin light chain variable region comprises an amino acid sequence selected from:

```
1B7:
                                      (SEQ ID NO: 7)
QIVLTQSPALMSASPGEKVTMTCSASSSVSFMYWYQQKPRSSPKPWIY

LTSNLPSGVPARFSGSGSGTSYSLTISSMEAEDAATYYCQQWSSHPPT

FGSGTKLEIK cdr1B7:
                                      (SEQ ID NO: 8)
QIVLTQSPDFQSVTPKEKVTITCSASSSVSFMYWYQQKPDQSPKPLIY

LTSNLPSGVPARFSGSGSGTSYTLTINSLEAEDAATYYCQQWSSHPPT

FGSGTKVEIK abb1B7:
                                      (SEQ ID NO: 9)
QIVLTQSPDFQSVTPKEKVTITCRASSSVSFMYWYQQKPDQSPKPLIY

LTSNLPSGVPARFSGSGSGTDYTLTINSLEAEDAATYYCQQWSSHPPT

FGSGTKVEIK sdr1B7:
                                      (SEQ ID NO: 10)
QIVLTQSPDFQSVTPKEKVTITCRASSIVSFLYWYQQKPDQSPKPLIY

LASNLPSGVPARFSGSGSGTDYTLTINSLEAEDAATYYCQQWSSHPPT

FGSGTKVEIK fra1B7:
                                      (SEQ ID NO: 11)
QIVLTQSPATLSVSPGERVTLTCSASSSVSFMYWYQQKPGRAPKPLIY

LTSNLPSGVPARFSGSGSGTSYTLTINSLEAEDAATYYCQQWSSHPPT

FGSGTKLEIK ven1B7:
                                      (SEQ ID NO: 12)
QIVLTQSPDFMSATPGEKVTMTCSASSSVSFMYWYQQKPRQSPKPWIY

LTSNLPSGVPARFSGSGSGTDYTLTINSMEAEDAATYYCQQWSSHPPT

FGSGTKLEIK
```

Any one of the disclosed 1B7 heavy chains can be paired with any of the disclosed 1B7 light chains. By way of illustration, the following pairs can be incorporated into an antibody of the present compositions and methods: SEQ ID NO: 1/SEQ ID NO: 7; SEQ ID NO: 1/SEQ ID NO: 8; SEQ ID NO: 1/SEQ ID NO: 9; SEQ ID NO: 1/SEQ ID NO: 10; SEQ ID NO: 1/SEQ ID NO: 11; SEQ ID NO: 1/SEQ ID NO: 12; SEQ ID NO: 2/SEQ ID NO: 7; SEQ ID NO: 2/SEQ ID NO: 8; SEQ ID NO: 2/SEQ ID NO: 9; SEQ ID NO: 2/SEQ ID NO: 10; SEQ ID NO: 2/SEQ ID NO: 11; SEQ ID NO: 2/SEQ ID NO: 12; SEQ ID NO: 3/SEQ ID NO: 7; SEQ ID NO: 3/SEQ ID NO: 8; SEQ ID NO: 3/SEQ ID NO: 9; SEQ ID NO: 3/SEQ ID NO: 10; SEQ ID NO: 3/SEQ ID NO: 11; SEQ ID NO: 3/SEQ ID NO: 12; SEQ ID NO: 4/SEQ ID NO: 7; SEQ ID NO: 4/SEQ ID NO: 8; SEQ ID NO: 4/SEQ ID NO: 9; SEQ ID NO: 4/SEQ ID NO: 10; SEQ ID NO: 4/SEQ ID NO: 11; SEQ ID NO: 4/SEQ ID NO: 12; SEQ ID NO: 5/SEQ ID NO: 7; SEQ ID NO: 5/SEQ ID NO: 8; SEQ ID NO: 5/SEQ ID NO: 9; SEQ ID NO: 5/SEQ ID NO: 10; SEQ ID NO: 5/SEQ ID NO: 11; SEQ ID NO: 5/SEQ ID NO: 12; SEQ ID NO: 6/SEQ ID NO: 7; SEQ ID NO: 6/SEQ ID NO: 8; SEQ ID NO: 6/SEQ ID NO: 9; SEQ ID NO: 6/SEQ ID NO: 10; SEQ ID NO: 6/SEQ ID NO: 11; and SEQ ID NO: 6/SEQ ID NO: 12.

In one embodiment, the humanized 1B7 antibody comprises an immunoglobulin heavy chain variable region comprising the amino acid sequence of SEQ ID NO: 2, and an immunoglobulin light chain variable region comprising the amino acid sequence of SEQ ID NO:8.

In one embodiment, the humanized 1B7 antibody comprises an immunoglobulin heavy chain variable region comprising the amino acid sequence of SEQ ID NO: 3, and an immunoglobulin light chain variable region comprising the amino acid sequence of SEQ ID NO:9.

In one embodiment, the humanized 1B7 antibody comprises an immunoglobulin heavy chain variable region comprising the amino acid sequence of SEQ ID NO: 4, and an immunoglobulin light chain variable region comprising the amino acid sequence of SEQ ID NO:10.

In one embodiment, the humanized 1B7 antibody comprises an immunoglobulin heavy chain variable region comprising the amino acid sequence of SEQ ID NO: 5, and an immunoglobulin light chain variable region comprising the amino acid sequence of SEQ ID NO:11.

In one embodiment, the humanized 1B7 antibody comprises an immunoglobulin heavy chain variable region comprising the amino acid sequence of SEQ ID NO: 6, and an immunoglobulin light chain variable region comprising the amino acid sequence of SEQ ID NO:12.

In other embodiments, the humanized 1B7 antibody comprises an immunoglobulin heavy chain variable region comprising an amino acid sequence having at least about 50% identity, about 51% identity, about 52% identity, about 53% identity, about 54% identity, about 55% identity, about 56% identity, about 57% identity, about 58% identity, about 59% identity, about 60% identity, about 61% identity, about 62% identity, about 63% identity, about 64% identity, about 65% identity, about 66% identity, about 67% identity, about 68% identity, about 69% identity, about 70% identity, about 71% identity, about 72% identity, about 73% identity, about 74% identity, about 75% identity, about 76% identity, about 77% identity, about 78% identity, about 79% identity, about 80% identity, about 81% identity, about 82% identity, about 83% identity, about 84% identity, about 85% identity, about 86% identity, about 87% identity, about 88% identity, about 89% identity, or about 90% identity to the entire variable region, the complementarity determining regions, or the framework region sequence of SEQ ID NO:1, SEQ ID NO:2, SEQ ID NO:3, SEQ ID NO:4, SEQ ID NO:5, or SEQ ID NO:6.

In other embodiments, the humanized 1B7 antibody comprises an immunoglobulin light chain variable region comprising an amino acid sequence having at least about 50% identity, about 51% identity, about 52% identity, about 53% identity, about 54% identity, about 55% identity, about 56% identity, about 57% identity, about 58% identity, about 59% identity, about 60% identity, about 61% identity, about 62% identity, about 63% identity, about 64% identity, about 65% identity, about 66% identity, about 67% identity, about 68% identity, about 69% identity, about 70% identity, about 71% identity, about 72% identity, about 73% identity, about 74% identity, about 75% identity, about 76% identity, about 77% identity, about 78% identity, about 79% identity, about 80% identity, about 81% identity, about 82% identity, about 83% identity, about 84% identity, about 85% identity, about 86% identity, about 87% identity, about 88% identity, about 89% identity, or about 90% identity to the entire variable region, the complementarity determining regions, or the framework region sequence of SEQ ID NO:7, SEQ ID NO:8, SEQ ID NO:9, SEQ ID NO:10, SEQ ID NO:11, or SEQ ID NO:12.

In one aspect, the present invention is directed to a humanized 11E6 antibody that binds a *pertussis* toxin protein, and comprises an immunoglobulin heavy chain variable region and an immunoglobulin light chain variable region. The immunoglobulin heavy chain variable region comprises an amino acid sequence selected from:

11E6:
(SEQ ID NO: 13)
EVKVVESGGGLVQPGGSLRLSCTTSGFTFTDYYVSWVRQPPGKALEWLGF

IRNKVNGYTTEFSSSVKGRFTISRDNSQSILYLQMNTLRVEDSATYYCAR

VSYYGRGWYFDYWGQGTTLTVSS cdr11E6:
(SEQ ID NO: 14)
EVQVVESGGGLVQPGRSLRLSCTTSGFTFTDYYVSWVRQAPGKALEWLGF

IRNKVNGYTTEFSSSVKGRFTISRDNSKSILYLQMNSLKIEDTAVYYCAR

VSYYGRGWYFDYWGQGTTVTVSS abb11E6:
(SEQ ID NO: 15)
EVQVVESGGGLVQPGRSLRLSCTTSGFTFTDYYVSWVRQAPGKALEWVGF

IRNKVNGYTTEFAASVRGRFTISRDNSKSILYLQMNSLKIEDTAVYYCAR

VSYYGRGWYFDYWGQGTTVTVSS sdr11E6:
(SEQ ID NO: 16)
EVQVVESGGGLVQPGRSLRLSCTTSGFTFTDYYVSWVRQAPGKALEWVGF

IRNKVNGYTTEFAASVRGRFTISRDNSKSILYLQMNSLKIEDTAVYYCAR

VSYYGRGWYFDYWGQGTTVTVSS fra11E6:
(SEQ ID NO: 17)
EVQVVESGGGLVQPGGSLRLSCTTSGFTFTDYYVSWVRQPPGKALEWLGF

IRNKVNGYTTEFSSSVKGRFTISRDNSKSTLYLQMNTLRVDDTAVYYCAR

VSYYGRGWYFDYWGQGTTLTVSS ven11E6:
(SEQ ID NO: 18)
EVQVVESGGGLVQPGRSLRLSCTTSGFTFTDYYVSWVRQAPGKALEWLGF

IRNKVNGYTTEFSSSVKGRFTISRDNSKSILYLQMNSLKIEDTAVYYCAR

VSYYGRGWYFDYWGQGTTLTVSS

The immunoglobulin light chain variable region comprises an amino acid sequence selected from:

11E6:
(SEQ ID NO: 19)
DIVMTQSTSSLSASLGDRVTISCRASQDIDNYLSWFQQKPDGTVKLLIYY

TSRLHSGVPSRFSGSGSGTDYSLTISSLDQEDIATYFCQQGNTFPWTFGG

GTKLEIK cdr11E6:
(SEQ ID NO: 20)
DIVMTQSPSSLSASVGDRVTISCRASQDIDNYLSWFQQKPGGTVKLLIYY

TSRLHSGVPSRFSGSGSGTDYTLTISSLQPEDIATYFCQQGNTFPWTFGG

GTKVEIK abb11E6:
(SEQ ID NO: 21)
DIVMTQSPSSLSASVGDRVTITCRASQDIDNYLSWFQQKPGGTVKLLIYY

TSRLHSGVPSRFSGSGSGTDYTLTISSLQPEDIATYFCQQGNTFPWTFGG

GTKVEIK sdr11E6:
(SEQ ID NO: 22)
DIVMTQSPSSLSASVGDRVTITCRASQDIDNYLSWFQQKPGGTVKLLIYY

TSRLHSGVPSRFSGSGSGTDYTLTISSLQPEDIATYFCQQGNTFPWTFGG

GTKVEIK fra11E6:
(SEQ ID NO: 23)
DIVMTQSPSSLSASVGDRVTISCRASQDIDNYLSWFQQKPGGTVKLLIYY

TSRLHSGVPSRFSGSGSGTDYTLTISSLQPEDIATYFCQQGNTFPWTFGG

GTKLEIK ven11E6:
(SEQ ID NO: 24)
DIVMTQSPSSLSASVGDRVTISCRASQDIDNYLSWFQQKPGGTVKLLIYY

TSRLHSGVPSRFSGSGSGTDYTLTISSLQPEDIATYFCQQGNTFPWTFGG

GTKLEIK

Any one of the disclosed 11E6 heavy chains can be paired with any of the disclosed 11E6 light chains. By way of illustration, the following pairs can be incorporated into an antibody of the present compositions and methods: SEQ ID NO: 13/SEQ ID NO: 19; SEQ ID NO: 13/SEQ ID NO: 20; SEQ ID NO: 13/SEQ ID NO: 21; SEQ ID NO: 13/SEQ ID NO: 22; SEQ ID NO: 13/SEQ ID NO: 23; SEQ ID NO: 13/SEQ ID NO: 24; SEQ ID NO: 14/SEQ ID NO: 19; SEQ ID NO: 14/SEQ ID NO: 20; SEQ ID NO: 14/SEQ ID NO: 21; SEQ ID NO: 14/SEQ ID NO: 22; SEQ ID NO: 14/SEQ ID NO: 23; SEQ ID NO: 14/SEQ ID NO: 24; SEQ ID NO: 15/SEQ ID NO: 19; SEQ ID NO: 15/SEQ ID NO: 20; SEQ ID NO: 15/SEQ ID NO: 21; SEQ ID NO: 15/SEQ ID NO: 22; SEQ ID NO: 15/SEQ ID NO: 23; SEQ ID NO: 15/SEQ ID NO: 24; SEQ ID NO: 16/SEQ ID NO: 19; SEQ ID NO: 16/SEQ ID NO: 20; SEQ ID NO: 16/SEQ ID NO: 21; SEQ ID NO: 16/SEQ ID NO: 22; SEQ ID NO: 16/SEQ ID NO: 23; SEQ ID NO: 16/SEQ ID NO: 24; SEQ ID NO: 17/SEQ ID NO: 19; SEQ ID NO: 17/SEQ ID NO: 20; SEQ ID NO: 17/SEQ ID NO: 21; SEQ ID NO: 17/SEQ ID NO: 22; SEQ ID NO: 17/SEQ ID NO: 23; SEQ ID NO: 17/SEQ ID NO: 24; SEQ ID NO: 18/SEQ ID NO: 19; SEQ ID NO: 18/SEQ ID NO: 20; SEQ ID NO: 18/SEQ ID NO: 21; SEQ ID NO: 18/SEQ ID NO: 22; SEQ ID NO: 18/SEQ ID NO: 23; and SEQ ID NO: 18/SEQ ID NO: 24.

In one embodiment, the humanized 11E6 antibody comprises an immunoglobulin heavy chain variable region comprising the amino acid sequence of SEQ ID NO: 14, and an immunoglobulin light chain variable region comprising the amino acid sequence of SEQ ID NO:20.

In one embodiment, the humanized 11E6 antibody comprises an immunoglobulin heavy chain variable region comprising the amino acid sequence of SEQ ID NO: 15, and an immunoglobulin light chain variable region comprising the amino acid sequence of SEQ ID NO:21.

In one embodiment, the humanized 11E6 antibody comprises an immunoglobulin heavy chain variable region comprising the amino acid sequence of SEQ ID NO: 16, and an immunoglobulin light chain variable region comprising the amino acid sequence of SEQ ID NO:22.

In one embodiment, the humanized 11E6 antibody comprises an immunoglobulin heavy chain variable region comprising the amino acid sequence of SEQ ID NO:17, and an immunoglobulin light chain variable region comprising the amino acid sequence of SEQ ID NO:23.

In one embodiment, the humanized 11E6 antibody comprises an immunoglobulin heavy chain variable region comprising the amino acid sequence of SEQ ID NO:18, and an immunoglobulin light chain variable region comprising the amino acid sequence of SEQ ID NO:24.

In other embodiments, the humanized 11E6 antibody comprises an immunoglobulin heavy chain variable region comprising an amino acid sequence having at least about 50% identity, about 51% identity, about 52% identity, about 53% identity, about 54% identity, about 55% identity, about 56% identity, about 57% identity, about 58% identity, about 59% identity, about 60% identity, about 61% identity, about 62% identity, about 63% identity, about 64% identity, about 65% identity, about 66% identity, about 67% identity, about 68% identity, about 69% identity, about 70% identity, about 71% identity, about 72% identity, about 73% identity, about 74% identity, about 75% identity, about 76% identity, about 77% identity, about 78% identity, about 79% identity, about 80% identity, about 81% identity, about 82% identity, about 83% identity, about 84% identity, about 85% identity, about 86% identity, about 87% identity, about 88% identity, about 89% identity, or about 90% identity to the entire variable region, the complementarity determining regions, or the framework region sequence of SEQ ID NO:13, SEQ ID NO:14, SEQ ID NO:15, SEQ ID NO:16, SEQ ID NO:17, and SEQ ID NO:18.

In other embodiments, the humanized 11E6 antibody comprises an immunoglobulin light chain variable region comprising an amino acid sequence having at least about 50% identity, about 51% identity, about 52% identity, about 53% identity, about 54% identity, about 55% identity, about 56% identity, about 57% identity, about 58% identity, about 59% identity, about 60% identity, about 61% identity, about 62% identity, about 63% identity, about 64% identity, about 65% identity, about 66% identity, about 67% identity, about 68% identity, about 69% identity, about 70% identity, about 71% identity, about 72% identity, about 73% identity, about 74% identity, about 75% identity, about 76% identity, about 77% identity, about 78% identity, about 79% identity, about 80% identity, about 81% identity, about 82% identity, about 83% identity, about 84% identity, about 85% identity, about 86% identity, about 87% identity, about 88% identity, about 89% identity, or about 90% identity to the entire variable region, the complementarity determining regions, or the framework region sequence of SEQ ID NO:19, SEQ ID NO:20, SEQ ID NO:21, SEQ ID NO:22, SEQ ID NO:23, and SEQ ID NO:24.

Homology or identity may be determined in various ways that are within the skill in the art, for instance, using publicly available computer software such as BLAST, BLAST-2, ALIGN or Megalign (DNASTAR) software. BLAST (Basic Local Alignment Search Tool) analysis using the algorithm employed by the programs blastp, blastn, blastx, tblastn and tblastx (Karlin et al., (1990) PROC. NATL. ACAD. SCI. USA 87, 2264-2268; Altschul, (1993) J. MOL. EVOL. 36, 290-300; Altschul et al., (1997) NUCLEIC ACIDS RES. 25, 3389-3402, incorporated by reference) are tailored for sequence similarity searching. The approach used by the BLAST program is to first consider similar segments between a query sequence and a database sequence, then to evaluate the statistical significance of all matches that are identified and finally to summarize only those matches which satisfy a preselected threshold of significance. For a discussion of basic issues in similarity searching of sequence databases see Altschul et al., (1994) NATURE GENETICS 6, 119-129 which is fully incorporated by reference. Those skilled in the art can determine appropriate parameters for measuring alignment, including any algorithms needed to achieve maximal alignment over the full length of the sequences being compared. The search parameters for histogram, descriptions, alignments, expect (i.e., the statistical significance threshold for reporting matches against database sequences), cutoff, matrix and filter are at the default settings. The default scoring matrix used by blastp, blastx, tblastn, and tblastx is the BLOSUM62 matrix (Henikoff et al., (1992) PROC. NATL. ACAD. SCI. USA 89, 10915-10919, fully incorporated by reference). Four blastn parameters may be adjusted as follows: Q=10 (gap creation penalty); R=10 (gap extension penalty); wink=1 (generates word hits at every wink.sup.th position along the query); and gapw=16 (sets the window width within which gapped alignments are generated). The equivalent Blastp parameter settings may be Q=9; R=2; wink=1; and gapw=32. Searches may also be conducted using the NCBI (National Center for Biotechnology Information) BLAST Advanced Option parameter (e.g.: -G, Cost to open gap [Integer]: default=5 for nucleotides/11 for proteins; -E, Cost to extend gap [Integer]: default=2 for nucleotides/1 for proteins; -q, Penalty for nucleotide mismatch [Integer]: default=-3; -r, reward for nucleotide match [Integer]: default=1; -e, expect value [Real]: default=10; -W, wordsize [Integer]: default=11 for nucleotides/28 for megablast/3 for proteins; -y, Dropoff (X) for blast extensions in bits: default=20 for blastn/7 for others; -X, X dropoff value for gapped alignment (in bits): default=15 for all programs, not applicable to blastn; and -Z, final X dropoff value for gapped alignment (in bits): 50 for blastn, 25 for others). ClustalW for pairwise protein alignments may also be used (default parameters may include, e.g., Blosum62 matrix and Gap Opening Penalty=10 and Gap Extension Penalty=0.1). A Bestfit comparison between sequences, available in the GCG package version 10.0, uses DNA parameters GAP=50 (gap creation penalty) and LEN=3 (gap extension penalty) and the equivalent settings in protein comparisons are GAP=8 and LEN=2.

In each of the foregoing embodiments, it is contemplated herein that the immunoglobulin heavy chain variable region sequences and/or light chain variable region sequences may contain amino acid alterations (e.g., amino acid substitutions, deletions, or insertions) relative to SEQ ID NOs:1-24. For example, the immunoglobulin heavy chain variable region sequences and/or light chain variable region sequences may contain from about 1 to about 50 mutations, from about 1 to about 40 mutations, from about 1 to about 35 mutations, from about 1 to about 30 mutations, about 1 to about 25 mutations, from about 1 to about 20 mutations, about 1 to about 15 mutations, or from about 1 to about 10 mutations independently selected from substitutions, deletions, or insertions with respect to SEQ ID NOs:1-24. In various embodiments, the immunoglobulin heavy chain variable region sequences and/or light chain variable region sequences have about 1 mutation, about 2 mutations, about 3 mutations, about 4 mutations, about 5 mutations, about 6 mutations, about 7 mutations, about 8 mutations, about 9 mutations, about 10 mutations, about 11 mutations, about 12 mutations, about 13 mutations, about 14 mutations, about 15 mutations, about 16 mutations, about 17 mutations, about 18 mutations, about 19 mutations, about 20 mutations, about 21 mutations, about 22 mutations, about 23 mutations, about 24 mutations, about 25 mutations, about 26 mutations, about 27 mutations, about 28 mutations, about 29 mutations, about 30 mutations, about 31 mutations, about 32 mutations, about 33 mutations, about 34 mutations, about 35 mutations, about 36 mutations, about 37 mutations, about 38 mutations, about 39 mutations, about 40 mutations, about 41 mutations, about 42 mutations, about 43 mutations, about 44 mutations, about 45 mutations, about 46 mutations, about 47 mutations, about 48 mutations, about 49 mutations, or about 50 mutations, relative to SEQ ID NOs:1-24. Illustrative amino acids that may be incorporated include a hydrophilic amino acid residue, which may include a polar and positively charged hydrophilic residue selected from arginine (R) and lysine (K), a polar and neutral of charge hydrophilic residue selected from asparagine (N), glutamine (Q), serine (S), threonine (T), proline (P), and cysteine (C), a polar and negatively charged hydrophilic residue selected from aspartate (D) and glutamate (E), or an aromatic, polar and positively charged hydrophilic including histidine (H); a hydrophobic amino acid residue which may include a hydrophobic, aliphatic amino acid selected from glycine (G), alanine (A), leucine (L), isoleucine (I), methionine (M), or valine (V) or a hydrophobic, aromatic amino acid selected from phenylalanine (F), tryptophan (W), or tyrosine (Y).

The ability of an antibody to bind a specific epitope can be described by the equilibrium dissociation constant ($K_D$). In certain embodiments, the present invention provides a humanized 1 B7 antibody that binds the *pertussis* toxin protein with a $K_D$ of about 20 nM or lower, or about 15 nM or lower, or about 10 nM or lower, or about 5 nM or lower. In an embodiment, the humanized 1B7 antibody binds the *pertussis* toxin protein with a $K_D$ of about 5 nM or lower or about 3 nM or lower. In illustrative embodiments, the humanized 1B7 antibody binds the *pertussis* toxin protein with a $K_D$ of about 5 nM, about 4.5 nM, about 4 nM, about 3.5 nM, about 3 nM, about 2.5 nM, about 2 nM, about 1.5 nM, about 1 nM, or about 0.5 nM.

In certain embodiments, the present invention provides a humanized 11E6 antibody that binds the *pertussis* toxin protein with a $K_D$ of about 20, about 19, or about 18, or about 17, or about 16, or about 15 nM or lower. In an embodiment, the humanized 11E6 antibody binds the *pertussis* toxin protein with a $K_D$ of 12 nM or lower. In illustrative embodiments, the humanized 1B7 antibody binds the *pertussis* toxin protein with a $K_D$ of about 15 nM, about 14.5 nM, about 14 nM, about 13.5 nM, about 13 nM, about 12.5 nM, about 12 nM, about 11.5 nM, about 11 nM, about 10.5 nM, about 10 nM, about 9.5 nM, about 9 nM, about 8.5 nM, about 8 nM, about 7.5 nM, about 7 nM, about 6.5 nM, about 6 nM, about 5.5 nM, about 5 nM, about 4.5 nM, about 4 nM, about 3.5 nM, about 3 nM, about 2.5 nM, about 2 nM, about 1.5 nM, about 1 nM, or about 0.5 nM.

In some embodiments, the humanized antibodies described herein compete with an antibody that is capable of binding a *pertussis* toxin protein. Where the humanized antibody competes with an antibody (competitor antibody) for binding a *pertussis* toxin protein, the humanized antibodies of the invention inhibit (completely or partially) binding of the competitor antibody to a measurable extent. The inhibition of binding may be measured by any of the methods known in the art. In general, a humanized antibody is considered to competitively inhibit binding of a competitor antibody (e.g., mouse 1B7 or 11E6 antibody as described by Sato et al., (1990), Infection and Immunity, 58(10): 3369-3374 or humanized 1B7 antibody as described by Maynard et al., U.S. Pat. No. 8,653,243, which are herein incorporated by reference in their entireties), if binding of the competitor antibody to the antigen is reduced by at least about 10%, at least about 20%, at least about 30%, at least about 40%, at least about 50%, at least about 60%, at least about 70%, at least about 80%, or at least about 90%, in the presence of the humanized antibody. Thus, in some embodiments, the antibody provided herein binds to a *pertussis* toxin protein competitively with a mouse 1B7 or 11E6 antibody as described by Sato et al., (1990), Infection and Immunity, 58(10): 3369-3374. In other embodiments, the antibody provided herein inhibits (completely or partially) the binding of a mouse 1B7 or 11E6 antibody. In some further embodiments, the antibody provided herein decreases the binding of a mouse 1B7 or 11E6 antibody in a competition assay by about 10%, about 20%, about 30%, about 40%, about 50%, about 60%, about 70%, about 80%, about 90% or about 100%.

Although the embodiments illustrated in the Examples may comprise pairs of variable regions, pairs of full length antibody chains, or pairs of CDR1, CDR2 and CDR3 regions, one from a heavy chain and one from a light chain, a skilled artisan will recognize that alternative embodiments may comprise single heavy chain variable regions or single light chain variable regions, single full length antibody chains, or CDR1, CDR2 and CDR3 regions from one antibody chain, either heavy or light.

Production of Antibodies

Methods for producing antibodies of the invention are described herein. For example, DNA molecules encoding light chain variable regions and/or heavy chain variable regions can be chemically synthesized using the sequence information provided herein. Synthetic DNA molecules can be ligated to other appropriate nucleotide sequences, including, e.g., constant region coding sequences, and expression control sequences, to produce gene expression constructs encoding the desired antibodies. Alternatively, the sequences provided herein can be cloned out of hybridomas by hybridization techniques or polymerase chain reaction (PCR) techniques using synthetic nucleic acid probes.

Nucleic acids encoding desired antibodies can be incorporated (ligated) into expression vectors, which can be introduced into host cells through transfection, transformation, or transduction techniques. For example, nucleic acids encoding desired antibodies can be introduced into host cells by retroviral transduction. Illustrative host cells are *E. coli* cells, Chinese hamster ovary (CHO) cells, human embryonic kidney 293 (HEK 293) cells, HeLa cells, baby hamster kidney (BHK) cells, monkey kidney cells (COS), human hepato cellular carcinoma cells (e.g., Hep G2), and myeloma cells that do not otherwise produce IgG protein. Transformed host cells can be grown under conditions that permit the host cells to express the genes that encode the immunoglobulin light and/or heavy chain variable regions.

Specific expression and purification conditions will vary depending upon the expression system employed. For example, if a gene is to be expressed in *E. coli*, it is first cloned into an expression vector by positioning the engineered gene downstream from a suitable bacterial promoter, e.g., Trp or Tac, and a prokaryotic signal sequence. The expressed secreted protein accumulates in refractile or inclusion bodies, and can be harvested after disruption of the cells by French press or sonication. The refractile bodies then are solubilized, and the proteins refolded and cleaved by methods known in the art.

If the engineered gene is to be expressed in eukaryotic host cells, e.g., CHO cells, it is first inserted into an expression vector containing a suitable eukaryotic promoter, a secretion signal, IgG enhancers, and various introns. This expression vector optionally contains sequences encoding all or part of a constant region, enabling an entire, or a part of, a heavy or light chain to be expressed. The gene construct can be introduced into eukaryotic host cells using transfection, transformation, or transduction techniques. The host cells express $V_L$ or $V_H$ fragments, $V_L$-$V_H$ heterodimers, $V_H$-$V_L$ or $V_L$-$V_H$ single chain polypeptides, complete heavy or light immunoglobulin chains, or portions thereof, each of which may be attached to a moiety having another function. In some embodiments, a host cell is transfected with a single vector expressing a polypeptide expressing an entire, or part of, a heavy chain (e.g., a heavy chain variable region) or a light chain (e.g., a light chain variable region). In other embodiments, a host cell is transfected with a single vector encoding (a) a polypeptide comprising a heavy chain variable region and a polypeptide comprising a light chain variable region, or (b) an entire immunoglobulin heavy chain and an entire immunoglobulin light chain. In still other embodiments, a host cell is co-transfected with more than one expression vector (e.g., one expression vector expressing a polypeptide comprising an entire, or part of, a heavy chain or heavy chain variable region, and another expression vector expressing a polypeptide comprising an entire, or part of, a light chain or light chain variable region).

A polypeptide comprising an immunoglobulin heavy chain variable region or light chain variable region can be produced by growing a host cell transfected with an expression vector encoding such variable region, under conditions that permit expression of the polypeptide. Following expression, the polypeptide can be harvested and purified using techniques well known in the art, e.g., affinity tags such as glutathione-S-transferase (GST) and histidine tags or by chromatography (by way of non-limiting example, based on size, charge, and/or specific binding).

A monoclonal antibody that binds the *pertussis* toxin protein, or an antigen-binding fragment of the antibody, can be produced by growing a host cell transfected, transformed or transduced with: (a) an expression vector that encodes a complete or partial immunoglobulin heavy chain, and a separate expression vector that encodes a complete or partial immunoglobulin light chain; or (b) a single expression vector that encodes both chains (e.g., complete or partial heavy and light chains), under conditions that permit expression of both chains. The intact antibody (or antigen-binding fragment) can be harvested and purified using techniques well known in the art, e.g., Protein A, Protein G, affinity tags such as glutathione-S-transferase (GST) and histidine tags or by chromatography. It is within ordinary skill in the art to express the heavy chain and the light chain from a single expression vector or from two separate expression vectors.

Antibody Modifications

There are standard methods for reducing or eliminating the antigenicity of antibodies and antibody fragments that are known in the art. When the antibodies are to be administered to a human, the antibodies preferably are "humanized" to reduce or eliminate antigenicity in humans. It is contemplated that the humanized antibodies have at least the same or substantially the same affinity for the antigen as the non-humanized mouse antibody from which it was derived.

However, it is noted that while humanization approaches are known in the art, such humanization approaches are often hindered by reductions in affinity (e.g. relative to the original murine antibody). This may be, without wishing to be bound by theory, due to the fact that the CDRs are not maintained workable configuration by the human frameworks. In this case, a small number of changes to the human framework sequences are made. These individual amino acid changes improve the affinity without making significant deviations from the human antibody structure so that the antibodies continue to resemble human antibodies. In that way, the antibodies can be used as for therapeutic purposes in humans without inducing an immune response. The choice of amino acids to change and the specific changes to be made are part of the present invention.

In one humanization approach, chimeric proteins are created in which mouse immunoglobulin constant regions are replaced with human immunoglobulin constant regions. See, e.g., Morrison et al., 1984, PROC. NAT. ACAD. SCI. 81:6851-6855, Neuberger et al., 1984, NATURE 312:604-608; U.S. Pat. No. 6,893,625 (Robinson); U.S. Pat. No. 5,500,362 (Robinson); and U.S. Pat. No. 4,816,567 (Cabilly). For example, in some embodiments, any one of SEQ ID NO: 1, or SEQ ID NO: 7, or SEQ ID NO: 13, or SEQ ID NO: 19 can be the variable regions that are paired with a human constant region.

In an approach known as CDR grafting, the CDRs of the light and heavy chain variable regions are grafted into frameworks from another species. For example, murine CDRs and non-CDR residues involved in antigen binding can be grafted into human sequences. Residues involved in maintaining the combining site structure and residues involved in maintaining $V_L$:$V_H$ contact may also be grafted. CDR grafting is described in U.S. Pat. No. 7,022,500 (Queen); U.S. Pat. No. 6,982,321 (Winter); U.S. Pat. No. 6,180,370 (Queen); U.S. Pat. No. 6,054,297 (Carter); U.S. Pat. No. 5,693,762 (Queen); U.S. Pat. No. 5,859,205 (Adair); U.S. Pat. No. 5,693,761 (Queen); U.S. Pat. No. 5,565,332 (Hoogenboom); U.S. Pat. No. 5,585,089 (Queen); U.S. Pat. No. 5,530,101 (Queen); Jones et al. (1986) NATURE 321: 522-525; Riechmann et al. (1988) NATURE 332: 323-327; Verhoeyen et al. (1988) SCIENCE 239: 1534-1536; and Winter (1998) FEBS LETT 430: 92-94.

In an approach called grafting of abbreviated CDRs, abbreviated CDRs, as defined by Padlan et al., (1995) FASEB J 9:133-139, and non-CDR residues involved in antigen binding, are transplanted into a human sequence. Residues involved in maintaining the combining site structure and residues involved in maintaining $V_L:V_H$ contact may also be grafted.

Other methods to reduce immunogenicity include "SDR-transfer," "veneering," and "Frankensteining" See, e.g., Padlan et al., (1995) FASEB J 9:133-139, Wu et al., (1992) MOL IMMUNOL 29:1141-1146, and Padlan et al., (1991) MOL IMMUNOL 28:489-498. In the SDR-transfer approach, residues involved in antigen binding (i.e., the specificity-determining residues or SDRs) are transplanted into a human sequence. Residues involved in maintaining the combining site structure and residues involved in maintaining $V_L:V_H$ contact may also be transplanted. In the veneering approach, the surface accessible amino acid residues in the murine antibody are replaced by amino acid residues more frequently found at the same positions in a human antibody. For example, the framework residues, which are exposed to solvent, are replaced with their homologues from a human sequence. The CDRs and non-CDR residues involved in antigen binding are preserved. In the Frankensteining approach, the CDRs are transplanted into a composite sequence constructed from the most similar human framework regions. Residues involved in maintaining the combining site structure and residues involved in maintaining $V_L:V_H$ contact may also be transplanted.

Any suitable approach, including any of the above approaches, can be used to reduce or eliminate human immunogenicity of an antibody.

In addition, it is possible to create fully human antibodies in mice. Fully human mAbs lacking any non-human sequences can be prepared from human immunoglobulin transgenic mice by techniques referenced in, e.g., Lonberg et al., NATURE 368:856-859, 1994; Fishwild et al., NATURE BIOTECHNOLOGY 14:845-851, 1996; and Mendez et al., NATURE GENETICS 15:146-156, 1997. Human mAbs can also be prepared and optimized from phage display libraries by techniques referenced in, e.g., Knappik et al., J. MOL. BIOL. 296:57-86, 2000; and Krebs et al., J. Immunol. Meth. 254:67-84 2001).

If the antibody is for use as a therapeutic, it can be conjugated to an effector agent such as a small molecule or a radionuclide using standard in vitro conjugation chemistries. If the effector agent is a polypeptide, the antibody can be chemically conjugated to the effector or joined to the effector as a fusion protein. Construction of fusion proteins is within ordinary skill in the art.

Methods of Using Antibodies

In one aspect, the method of the invention involves treating a patient with *Bordetella pertussis*, comprising administering to the patient the humanized 1B7 antibody (e.g. in an effective amount) and/or the humanized 11E6 antibody (e.g. in an effective amount), or pharmaceutical compositions including the antibody or antibodies.

In another aspect, the method of the invention involves a method of preventing a *Bordetella pertussis* infection, comprising administering to a patient the humanized 1B7 antibody (e.g. in an effective amount) and/or the humanized 11E6 antibody (e.g. in an effective amount), or pharmaceutical compositions including the antibody or antibodies and, in some embodiments, the patient is at risk for a *Bordetella pertussis* infection (e.g. the patient is a pre-vaccination infant and/or the patient has been exposed to a *pertussis* toxin).

Leukocytosis or elevation in white blood cell count is characteristic of *Bordetella pertussis* infections. In one embodiment, the method of the invention comprises a reduction in white blood cell count in the patient. In an embodiment, the method of the invention results in an acceleration of the resolution of leukocytosis. In another embodiment, the method of the invention results in a reduction of the maximum white blood cell count during the course of the infection.

In various embodiments, the method of the invention results in an improvement of whooping cough in the patient. In one embodiment, the coughing symptoms of the patient are improved. For example, the method reduces the frequency of coughing or the number of coughs (or coughing episodes) in the patient. In various embodiments, the method reduces the number of coughs or coughing episodes by at least about 1 per hour, at least about 2 per hour, at least about 3 per hour, at least about 4 per hour, at least about 5 per hour, at least about 6 per hour, at least about 7 per hour, at least about 8 per hour, at least about 9 per hour, at least about 10 per hour, at least about 15 per hour, at least about 20 per hour, at least about 25 per hour, at least about 30 per hour, at least about 35 per hour, at least about 40 per hour, at least about 45 per hour, at least about 50 per hour, at least about 55 per hour, at least about 60 per hour, at least about 65 per hour, at least about 70 per hour, at least about 75 per hour, at least about 80 per hour, at least about 85 per hour, at least about 90 per hour, at least about 95 per hour, or at least about 100 per hour. In another example, the method reduces the duration of coughing in the patient. For example, the method reduces the duration of coughing during the course of the infection by at least about three months, about two months, about one month, about 4 weeks, about 3 weeks, about 2 weeks, about 1 week, about 5 days, about 4 days, about 3 days, about 2 days, or about 1 day. In a further embodiment, the number of whoops is reduced in the patient.

In another embodiment, the method of the invention reduces the level of the *Bordetella pertussis* bacteria in the nasopharynx of the patient. In a further embodiment, the method of the invention reduces the level of the *Bordetella pertussis* bacteria in the lung of the patient (e.g. bacterial lung colonization). For example, the method reduces the *Bordetella pertussis* levels in the nasopharynx and/or the lungs by about 95%, about 90%, about 80%, about 70%, about 60%, about 50%, about 40%, about 30%, about 20%, about 10%, or about 5%.

In one embodiment, the method of the invention results in neutralization (inhibition or antagonization) of the *pertussis* toxin protein. For example, antibodies of the invention can bind to the *pertussis* toxin protein so as to partially or completely inhibit one or more biological activities of the *pertussis* toxin protein. Among the biological activities of a *pertussis* toxin protein that a neutralizing antibody may inhibit or block is the ability of a *pertussis* toxin protein to bind cellular receptors. The receptor binding region of a *pertussis* toxin protein consists of four polypeptide subunits referred to as subunit S2, subunit S3, subunit S4 and subunit S5, respectively. Examples of cellular receptors that are bound by the subunits S2, S3, S4, and S5 of a *pertussis* toxin protein are members of the N-linked sialoglycoprotein family such as fetuin, haptoblobin, and transferrin. In an illustrative embodiment, the humanized antibodies of the invention prevent the *pertussis* toxin protein from binding to its cellular receptor. In another embodiment, the humanized antibodies of the invention alter the intracelluar trafficking steps of the *pertussis* toxin such that the toxin does not reach the cellular cytosol. Another important activity of a *pertussis* toxin protein that may be inhibited by antibodies of the invention is the enzymatic activity of the *pertussis* toxin protein as ADP ribosylase towards G proteins. The subunit conferring to the enzymatic activity as ADP -ribosylase in a *pertussis* toxin protein is subunit S1. In some embodiments, the *pertussis* toxin protein is a *pertussis* holotoxin. A *pertussis* holotoxin as referred to herein as a *pertussis* toxin protein that includes all five *pertussis* toxin protein subunits. In other embodiments, the *pertussis* toxin protein is a truncated *pertussis* toxin protein. A truncated *pertussis* protein as referred to herein includes at least one of the *pertussis* toxin protein subunits (i.e., S1, S2, S3, S4 and S5). *Pertussis* toxin proteins of various forms are described in, for example, U.S. Pat. No. 8,653,243, which is herein incorporated by reference in its entirety.

In various embodiments, the present compositions and methods are useful in the treatment or prevention of any of the stages of *pertussis* infections. For example, the incubation period of *pertussis* is commonly 7-10 days, with a range of 4-21 days, and rarely may be as long as 42 days. In various embodiments, the present compositions and methods increase the length of the incubation period by making the infection more difficult to come about. The clinical course of the illness is divided into three stages. The first stage, the catarrhal stage, is characterized by the insidious onset of coryza, sneezing, low-grade fever, and a mild, occasional cough, similar to the common cold. The cough gradually becomes more severe, and after 1-2 weeks, the second, or paroxysmal stage, begins. In various embodiments, the present compositions and methods, reduce the length of the catarrhal stage and, optionally, prevent it from advancing to the paroxysmal stage. In various embodiments, the present compositions and methods treat one or more of coryza, sneezing, low-grade fever, and cough. It is during the paroxysmal stage that the diagnosis of *pertussis* is usually suspected. Characteristically, a patient has bursts, or paroxysms, of numerous, rapid coughs, apparently due to difficulty expelling thick mucus from the tracheobronchial tree. At the end of the paroxysm, a long inspiratory effort is usually accompanied by a characteristic high-pitched whoop. During such an attack, the patient may become cyanotic. Children and young infants, especially, appear very ill and distressed. Vomiting and exhaustion commonly follow the episode. In various embodiments, the present compositions and methods reduce the quantity and/or frequency of paroxysms. In various embodiments, the present compositions and methods prevent a patient from becoming cyanotic. Paroxysmal attacks occur more frequently at night, with an average of 15 attacks per 24 hours. During the first 1 or 2 weeks of this stage, the attacks increase in frequency, remain at the same level for 2 to 3 weeks, and then gradually decrease. The paroxysmal stage usually lasts 1 to 6 weeks but may persist for up to 10 weeks. In various embodiments, the present compositions and methods reduce the length of this stage. In the convalescent stage, recovery is gradual. The cough becomes less paroxysmal and disappears in 2 to 3 weeks. In various embodiments, the present compositions and methods accelerate the onset of this stage and/or reduce its duration. Further, in various embodiments, the present compositions and methods prevent or reduce the recurrence of paroxysms, which may occur with subsequent respiratory infections. In various embodiments, the present compositions and methods prevent or reduce one or more of the onset of secondary bacterial pneumonia, neurologic complications such as seizures and encephalopathy, hypoxia, otitis media, dehydration, pneumothorax, epistaxis, subdural hematomas, hernias, rectal prolapsed, difficulty sleeping, urinary incontinence, pneumonia, and rib fracture. Further, in some embodiments, the present compositions and methods reduce or prevent necrotizing bronchiolitis, pneumonia (e.g. from *Bordetella pertussis*), pulmonary edema, pulmonary hypertension, and death.

In an embodiment, methods of the invention involve co-administration of the humanized 1B7 antibody and the humanized 11E6 antibody to the patient. In some embodiments, co-administration produces synergistic effects. Co-administration of the humanized 1B7 antibody and the humanized 11E6 antibody may be simultaneous or sequential.

In some embodiments, the humanized 1B7 antibody and the humanized 11E6 antibody are administered to a subject simultaneously. The term "simultaneously" as used herein, means that the humanized 1B7 antibody and the humanized 11E6 antibody are administered with a time separation of no more than about 60 minutes, such as no more than about 30 minutes, no more than about 20 minutes, no more than about 10 minutes, no more than about 5 minutes, or no more than about 1 minute. Administration of the humanized 1B7 antibody and the humanized 11E6 antibody can be by simultaneous administration of a single formulation (e.g., a formulation comprising the humanized 1B7 antibody and the humanized 11E6 antibody) or of separate formulations (e.g., a first formulation including the humanized 1B7 antibody and a second formulation including the humanized 11E6 antibody).

Co-administration does not require the therapeutic agents to be administered simultaneously, if the timing of their administration is such that the pharmacological activities of the humanized 1B7 antibody and the 11E6 antibody overlap in time, thereby exerting a combined therapeutic effect. For example, the humanized 1B7 antibody and the humanized 11E6 antibody can be administered sequentially. The term "sequentially" as used herein means that the humanized 1B7 antibody and the humanized 11E6 antibody are administered with a time separation of more than about 60 minutes. For example, the time between the sequential administration of the humanized 1B7 antibody and the humanized 11E6 antibody can be more than about 60 minutes, more than about 2 hours, more than about 5 hours, more than about 10 hours, more than about 1 day, more than about 2 days, more than about 3 days, or more than about 1 week apart. The optimal administration times will depend on the rates of metabolism, excretion, and/or the pharmacodynamic activity of the humanized 1B7 antibody and the humanized 11E6 antibody being administered.

For example, in some embodiments, the antibodies of the present invention have a peak in a serum concentration (e.g. a beta half-life) of at least about 30, or about 35, or about 40, or about 45, or about 50, or about 55, or about 60, or about 65, or about 70, or about 75, or about 80 hours post-administration or at least about 1 day, about 2 days, about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, about 21 days, about 22 days, about 23 days, about 24 days, or about 25 days). In some embodiments, the antibodies of the present invention have prolonged half-lives. In some embodiments, the antibodies of the present invention have an in vivo half-life of about 200, or about 225, or about 250, or about 275, or about 300 hours or about 7 days, about 8 days, about 9 days, about 10 days, about 11 days, about 12 days, about 13 days, about 14 days, about 15 days, about 16 days, about 17 days, about 18 days, about 19 days, about 20 days, about 21 days, about 22 days, about 23 days, about 24 days, about 25 days, about 26 days, about 27 days, about 28 days, about 29 days, about 30 days, about 31 days, about 32 days, about 33 days, about 34 days, or about 35 days, e.g. about 1 or about 2 weeks, or about 3 weeks, about 4 weeks, or about 5 weeks).

Accordingly, in some embodiments, a patient may receive a first administration (e.g. infusion or intramuscular (IM) injection) of the inventive antibodies as part of a treatment method and may receive a further administration (e.g. infusion or intramuscular injection) after a peak in serum concentration and/or the in vivo half-life of the antibodies of the present invention (e.g. the dose of the further administration may be identical to the first administration or may be lower, e.g. a maintenance dose). In some embodiments, the further administration is about one day from the first administration, or about one week from the first administration. In some embodiments, the present methods provide for about 1-3 (e.g. about 1, or about 2, or about 3) doses (e.g. IV doses or IM doses) of the antibodies of the present invention per week (or about every 5, or 6, or 7, or 10 days). In some embodiments, the present methods maintain a therapeutic window of antibody levels in the blood serum of about 5 µg/mL, about 10 µg/mL, about 20 µg/mL, about 25 µg/mL, about 50 µg/mL, about 75 µg/mL, or about 100 µg/mL, or about 125 µg/mL, or about 150 µg/mL, or about 175 µg/mL, or about 200 µg/mL, or about 225 µg/mL, or about 250 µg/mL, or about 300 µg/mL. In some embodiments, the present methods allow for infrequent dosing and/or lower dosing (e.g. longer half-lives permitting lower and less frequent dosing).

Either the humanized 1B7 antibody or the humanized 11E6 antibody can be administered first. For example, the humanized 1B7 antibody can be administered to a subject after the time at which the humanized 11E6 antibody is administered. In this case, it is generally desirable to administer the humanized 1B7 antibody prior to the time at which about 50% (e.g., prior to the time at which about 40%, about 30%, about 20%, about 10%, or about 5%) of the humanized 11E6 antibody is metabolized or excreted by the subject, or the time at which the humanized 11E6 antibody has reached about 50%, about 60%, about 70%, about 80%, about 90%, or about 100% of its pharmacodynamic activity. In another example, the humanized 1 B7 antibody can be administered to a subject before the administration of the humanized 11E6 antibody. In this case, it is generally desirable to administer the humanized 11E6 antibody prior to the time at which about 50% (e.g., prior to the time at which about 40%, about 30%, about 20%, about 10%, or about 5%) of the humanized 1B7 antibody is metabolized or excreted by the subject, or the time at which the humanized 1B7 antibody being administered has reached about 50%, about 60%, about 70%, about 80%, about 90%, or about 100% of its pharmacodynamic activity.

Co-administration also does not require the therapeutic agents to be administered to the patient by the same route of administration. Rather, each therapeutic agent can be administered by any appropriate route, for example, parenterally or non-parenterally. In an embodiment, the therapeutic agents may be administered orally to the subject. In another embodiment, the therapeutic agents may be administered parenterally, including for example, intravenous, intramuscular, intraperitoneal, subcutaneous and intra-articular injection and infusion, among others. In an embodiment, the therapeutic agents may be administered through intramuscular injection to the subject.

In another embodiment, the method includes administering to a patient the humanized 1B7 antibody and/or the 11E6 antibody, along with antimicrobial agents. It is contemplated that co-administration of the humanized 1B7 antibody and/or the 11E6 antibody along with antimicrobial agents produces synergistic effects. Illustrative antimicrobial agents that may be used for the invention include, but are not limited to azithromycin, clarithromycin, erythromycin, trimethoprim-sulfamethoxasole, roxithromycin, ketolides (e.g., telithromycin) ampicillin, amoxicillin, tetracycline, chloramphenicol, fluoroquinolones (e.g., ciprofloxacin, levofloxacin, ofloxacin, moxifloxacin), and cephalosporins. In an embodiment, the antimicrobial agent is erythromycin.

In various embodiments, the method of the invention treats human patients. In an embodiment, the human patient is an infant. In an embodiment, the human patient is a newborn. In another embodiment, the human patient is a neonate who is less than four weeks old, less than three weeks old, less than two weeks old, less than one week old, less than six days old, less than five days old, less than four days old, less than three days old, less than two days old, or less than one day old. In some embodiments, the human is one month old, two months old, three months old, four months old, five months old, or six months old. In some embodiments, the human has an age in a range of from about 6 to about 18 months old, from about 18 to about 36 months old, from about 1 to about 5 years old, from about 5 to about 10 years old, from about 10 to about 15 years old, from about 15 to about 20 years old, from about 20 to about 25 years old, from about 25 to about 30 years old, from about 30 to about 35 years old, from about 35 to about 40 years old, from about 40 to about 45 years old, from about 45 to about 50 years old, from about 50 to about 55 years old, from about 55 to about 60 years old, from about 60 to about 65 years old, from about 65 to about 70 years old, from about 70 to about 75 years old, from about 75 to about 80 years old, from about 80 to about 85 years old, from about 85 to about 90 years old, from about 90 to about 95 years old or from about 95 to about 100 years old.

In a further aspect, the method of the invention prevents *Bordetella pertussis* infection in a subject previously exposed to the bacteria, comprising administering to the subject the humanized 1B7 antibody and/or the humanized 11E6 antibody, or pharmaceutical compositions including the antibody or antibodies. In various embodiments, the method provides an effective prophylactic treatment in preventing *Bordetella pertussis* infection in a subject exposed to the bacteria.

In some embodiments, the antibody of the invention (e.g., humanized hu1B7 antibody and/or hu11E6 antibody) is utilized in prophylactic applications in a subject who has not been previously vaccinated against the bacteria. In an embodiment, the antibody of the invention is administered to a subject as a prophylactic treatment prior to the subject receiving a *pertussis* vaccination. In various embodiments, the antibody of the invention is utilized in prophylactic treatments of a subject who is less than one year old, less than eleven months old, less than ten months old, less than nine months old, less than eight months old, less than seven months old, less than six months old, less than five months old, less than four months old, less than three months old, less than two months old, less than one month old, less than four weeks old, less than three weeks old, less than two weeks old, less than one week old, less than six days old, less than five days old, less than four days old, less than three days old, less than two days old, or less than one day old. Accordingly, in some embodiments, the present methods involving bridging the time between birth and vaccination in an infant patient.

In various embodiments, the methods of the invention treat or prevent *Bordetella pertussis* infection in a subject previously vaccinated against the bacteria. In an embodiment, the subject is an infant or child vaccinated with DtaP (e.g., INFANRIX (with three antigens, mostly *pertussis* toxin (PT) and. FHA), TRIPEDIA (which contains two components, FHA and PT, in equal amounts) and DAPTACEL (which contains five components, PT, FHA, pertactin, and fimbriae types 2 and 3)). In another embodiment, the subject is an adult vaccinated with the *pertussis* booster vaccine Tdap (e.g. BOOSTRIX (with three *pertussis* antigens (PT, FHA, and pertactin) in a reduced quantity compared with INFANRIX) and ADACEL (with the same five *pertussis* components as DAPTACEL but with a reduced quantity of PT). In other embodiments, the patient of the present invention may or may not have received any one of the following *pertussis* combination vaccines: PEDIARIX, PENTACEL, or KINRIX.

It is contemplated that the humanized antibodies of the invention may further function as adjuvant for vaccinations such as DtaP or Tdap. Further, in various embodiments, the methods of the invention treat or prevent *Bordetella pertussis* infection in a subject that has not been previously vaccinated against the bacteria In various embodiments, the present compositions and methods supplement or supplant treatment with palivizumab (SYNAGIS).

In various embodiments, the present compositions and methods can treat *pertussis* infections that have various strains as their etiology, including, by way of non-limiting example, pertactin-negative *pertussis*.

Furthermore, *Bordetella parapertussis* is a closely related species *Bordetella pertussis*. Both bacteria are linked to outbreaks of whooping cough in humans and produce similar virulence factors. Co-infection of *Bordetella pertussis* and *Bordetella parapertussis* is not unusual. Accordingly, in one aspect of the invention, the method of the invention involves treating a patient with *Bordetella parapertussis*, comprising administering to the patient the humanized 1B7 antibody and/or the humanized 11E6 antibody, or pharmaceutical compositions including the antibody or antibodies. In another aspect of the invention, the method of the invention prevents *Bordetella parapertussis* infection in a subject previously exposed to the bacteria, comprising administering to the subject the humanized 1B7 antibody and/or the humanized 11E6 antibody, or pharmaceutical compositions including the antibody or antibodies.

In various embodiments, the methods of the invention are effective in treating *Bordetella pertussis* infection and/or *Bordetella parapertussis* infection when the humanized 1B7 antibody and/or the humanized 11E6 antibody is administered to the patient at about 3 months after infection. In other embodiments, the methods of the invention are effective in treating *Bordetella pertussis* infection and/or *Bordetella parapertussis* infection when the humanized 1B7 antibody and/or the humanized 11E6 antibody is administered to the patient at about 2 months, about 1 month, about 4 weeks, about 3 weeks, about 2 weeks, about 7 days, about 6 days, about 5 days, about 4 days, about 3 days, about 2 days, or about 1 day after infection. In an embodiment, the humanized 1B7 antibody and/or the humanized 11E6 antibody is administered to the patient on the day of infection.

As used herein, "treat," "treating" and "treatment" mean the treatment of a disease in a mammal, e.g., in a human. In various embodiments, this includes: (a) inhibiting the disease, i.e., arresting its development and/or (b) relieving the disease, i.e., causing regression of the disease state.

Pharmaceutical Compositions and Administration

The pharmaceutical compositions of the invention can be administered for therapeutic or prophylactic treatment. For such uses, an antibody preferably is combined with a pharmaceutically acceptable carrier. As used herein, "pharmaceutically acceptable carrier" means buffers, carriers, and excipients suitable for use in contact with the tissues of human beings and animals without excessive toxicity, irritation, allergic response, or other problem or complication, commensurate with a reasonable benefit/risk ratio. The carrier(s) should be "acceptable" in the sense of being compatible with the other ingredients of the formulations and not deleterious to the recipient. Pharmaceutically acceptable carriers include buffers, solvents, dispersion media, coatings, isotonic and absorption delaying agents, and the like, that are compatible with pharmaceutical administration. The use of such media and agents for pharmaceutically active substances is known in the art.

Pharmaceutical compositions containing antibodies, such as those disclosed herein, can be presented in a dosage unit form and can be prepared by any suitable method. A pharmaceutical composition should be formulated to be compatible with its intended route of administration. Examples of routes of administration are oral, intranasal, pulmonary, intravenous (IV), intradermal, inhalation, transdermal, topical, transmucosal, subcutaneous, intramuscular (IM), intraperitoneal, and rectal administration. In an embodiment, the route of administration for antibodies of the invention is IV infusion. In another embodiment, the route of administration for antibodies of the invention is IM injection.

Useful formulations can be prepared by methods well known in the pharmaceutical art. For example, pharmaceutical compositions of the invention can be formulated as a colloidal dispersion system, macromolecular complex, nanocapsule, microsphere, bead, oil-in-water emulsion, micelle, mixed micelle, or liposome. For example, see *Remington's Pharmaceutical Sciences*, 18th ed. (Mack Publishing Company, 1990).

Formulation components suitable for parenteral administration include a sterile diluent such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as EDTA; buffers such as acetates, citrates or phosphates; and agents for the adjustment of tonicity such as sodium chloride or dextrose.

For intravenous administration, suitable carriers include physiological saline, bacteriostatic water, Cremophor ELTM (BASF, Parsippany, N.J.) or phosphate buffered saline (PBS). The carrier should be stable under the conditions of manufacture and storage, and should be preserved against microorganisms. The carrier can be a solvent or dispersion medium containing, for example, water, ethanol, polyol (for example, glycerol, propylene glycol, and liquid polyetheylene glycol), and suitable mixtures thereof.

The compositions provided herein, alone or in combination with other suitable components, can be made into aerosol formulations (i.e., "nebulized") to be administered via inhalation. Aerosol formulations can be placed into pressurized acceptable propellants, such as dichlorodifluoromethane, propane, nitrogen, and the like.

Pharmaceutical formulations preferably are sterile. Sterilization can be accomplished, for example, by filtration through sterile filtration membranes. Where the composition is lyophilized, filter sterilization can be conducted prior to or following lyophilization and reconstitution.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. The composition can also contain other compatible therapeutic agents. For example, the composition may additionally include antimicrobial agents described herein.

The combined administrations contemplates co-administration, using separate formulations or a single pharmaceutical formulation, and consecutive administration in either order, wherein preferably there is a time period while both (or all) active agents simultaneously exert their biological activities. In an embodiment, a pharmaceutical composition of the invention includes a formulation of the humanized 1B7 antibody. In another embodiment, a pharmaceutical composition of the invention includes a formulation of the humanized 11E6 antibody. In a further embodiment, a pharmaceutical composition of the invention includes a co-formulation of both the humanized 1B7 antibody and the humanized 11E6 antibody.

It will be appreciated that the actual dose of the antibodies (e.g., humanized hu1B7 antibody and/or hu11E6 antibody) to be administered according to the present invention will vary according to, for example, the particular dosage form and the mode of administration. Many factors that may modify the action of the antibodies (e.g., body weight, gender, diet, time of administration, route of administration, rate of excretion, condition of the subject, drug combinations, genetic disposition and reaction sensitivities) can be taken into account by those skilled in the art. Administration can be carried out continuously or in one or more discrete doses within the maximum tolerated dose. Optimal administration rates for a given set of conditions can be ascertained by those skilled in the art using conventional dosage administration tests.

Individual doses of the antibody (e.g., humanized hu1B7 antibody and/or hu11E6 antibody) can be administered in unit dosage forms containing, for example, from about 0.01 mg to about 1,000 mg, from about 0.01 mg to about 950 mg, from about 0.01 mg to about 900 mg, from about 0.01 mg to about 850 mg, from about 0.01 mg to about 800 mg, from about 0.01 mg to about 750 mg, from about 0.01 mg to about 700 mg, from about 0.01 mg to about 650 mg, from about 0.01 mg to about 600 mg, from about 0.01 mg to about 550 mg, from about 0.01 mg to about 500 mg, from about 0.01 mg to about 450 mg, from about 0.01 mg to about 400 mg, from about 0.01 mg to about 350 mg, from about 0.01 mg to about 300 mg, from about 0.01 mg to about 250 mg, from about 0.01 mg to about 200 mg, from about 0.01 mg to about 150 mg, from about 0.01 mg to about 100 mg, from about 0.1 mg to about 90 mg, from about 0.1 mg to about 80 mg, from about 0.1 mg to about 70 mg, from about 0.1 mg to about 60 mg, from about 0.1 mg to about 50 mg, from 0.1 mg to about 40 mg active ingredient, from about 0.1 mg to about 30 mg, from about 0.1 mg to about 20 mg, from about 0.1 mg to about 10 mg, from about 0.1 mg to about 5 mg, from about 0.1 mg to about 3 mg, from about 0.1 mg to about 1 mg per unit dosage form, or from about 5 mg to about 80 mg per unit dosage form. For example, a unit dosage form can be about 0.01 mg, about 0.02 mg, about 0.03 mg, about 0.04 mg, about 0.05mg, about 0.06 mg, about 0.07 mg, about 0.08 mg, about 0.09 mg, about 0.1 mg, about 0.2 mg, about 0.3 mg, about 0.4 mg, about 0.5 mg, about 0.6 mg, about 0.7 mg, about 0.8 mg, about 0.9 mg, about 1 mg, about 2 mg, about 3 mg, about 4 mg, about 5 mg, about 6 mg, about 7 mg, about 8 mg, about 9 mg about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 150 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, or about 1,000 mg, inclusive of all values and ranges therebetween.

In one embodiment, the antibody (e.g., humanized hu1B7 antibody and/or hu11E6 antibody) is administered at an amount of from about 0.01 mg to about 100 mg daily, an amount of from about 0.01 mg to about 1,000 mg daily from about 0.01 mg to about 950 mg daily, from about 0.01 mg to about 900 mg daily, from about 0.01 mg to about 850 mg daily, from about 0.01 mg to about 800 mg daily, from about 0.01 mg to about 750 mg daily, from about 0.01 mg to about 700 mg daily, from about 0.01 mg to about 650 mg daily, from about 0.01 mg to about 600 mg daily, from about 0.01 mg to about 550 mg daily, from about 0.01 mg to about 500 mg daily, from about 0.01 mg to about 450 mg daily, from about 0.01 mg to about 400 mg daily, from about 0.01 mg to about 350 mg daily, from about 0.01 mg to about 300 mg daily, from about 0.01 mg to about 250 mg daily, from about 0.01 mg to about 200 mg daily, from about 0.01 mg to about 150 mg daily, from about 0.1 mg to about 100 mg daily, from about 0.1 mg to about 95 mg daily, from about 0.1 mg to about 90 mg daily, from about 0.1 mg to about 85 mg daily, from about 0.1 mg to about 80 mg daily, from about 0.1 mg to about 75 mg daily, from about 0.1 mg to about 70 mg daily, from about 0.1 mg to about 65 mg daily, from about 0.1 mg to about 60 mg daily, from about 0.1 mg to about 55 mg daily, from about 0.1 mg to about 50 mg daily, from about 0.1 mg to about 45 mg daily, from about 0.1 mg to about 40 mg daily, from about 0.1 mg to about 35 mg daily, from about 0.1 mg to about 30 mg daily, from about 0.1 mg to about 25 mg daily, from about 0.1 mg to about 20 mg daily, from about 0.1 mg to about 15 mg daily, from about 0.1 mg to about 10 mg daily, from about 0.1 mg to about 5 mg daily, from about 0.1 mg to about 3 mg daily, from about 0.1 mg to about 1 mg daily, or from about 5 mg to about 80 mg daily. In various embodiments, the antibody is administered at a daily dose of about 0.01 mg, about 0.02 mg, about 0.03 mg, about 0.04 mg, about 0.05mg, about 0.06 mg, about 0.07 mg, about 0.08 mg, about 0.09 mg, about 0.1 mg, about 0.2 mg, about 0.3 mg, about 0.4 mg, about 0.5 mg, about 0.6 mg, about 0.7 mg, about 0.8 mg, about 0.9 mg, about 1 mg, about 2 mg, about 3 mg, about 4 mg, about 5 mg, about 6 mg, about 7 mg, about 8 mg, about 9 mg about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 150 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, or about 1,000 mg, inclusive of all values and ranges therebetween.

In some embodiments, a suitable dosage of the antibody (e.g., humanized hu1B7 antibody and/or hu11E6 antibody) is in a range of about 0.01 mg/kg to about 100 mg/kg of body weight of the subject, for example, about 0.01 mg/kg, about 0.02 mg/kg, about 0.03 mg/kg, about 0.04 mg/kg, about 0.05 mg/kg, about 0.06 mg/kg, about 0.07 mg/kg, about 0.08 mg/kg, about 0.09 mg/kg, about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1 mg/kg, about 1.1 mg/kg, about 1.2 mg/kg, about 1.3 mg/kg, about 1.4 mg/kg, about 1.5mg/kg, about 1.6 mg/kg, about 1.7 mg/kg, about 1.8 mg/kg, 1.9 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, or about 100 mg/kg body weight, inclusive of all values and ranges therebetween. In other embodiments, a suitable dosage of the antibody in a range of about 0.01 mg/kg to about 100 mg/kg of body weight, in a range of about 1 mg/kg to about 100 mg/kg of body weight, in a range of about 1 mg/kg to about 90 mg/kg of body weight, in a range of about 1 mg/kg to about 80 mg/kg of body weight, in a range of about 1 mg/kg to about 70 mg/kg of body weight, in a range of 1 mg/kg to about 60 mg/kg of body weight, in a range of 1 mg/kg to about 50 mg/kg of body weight, in a range of 1 mg/kg to about 40 mg/kg of body weight, in a range of 1 mg/kg to about 30 mg/kg of body weight, in a range of 1 mg/kg to about 20 mg/kg of body weight, in a range of about 5 mg/kg to about 50 mg/kg of body weight, in a range of about 5 mg/kg to about 40 mg/kg of body weight, in a range of about 5 mg/kg to about 30 mg/kg of body weight, in a range of about 5 mg/kg to about 20 mg/kg of body weight, inclusive of all values and ranges therebetween.

In accordance with certain embodiments of the invention, the antibody (e.g., humanized hu1B7 antibody and/or hu11E6 antibody) may be administered, for example, more than once daily, about once per day, about every other day, about every third day, about once a week, about once every two weeks, about once every month, about once every two months, about once every three months, about once every six months, or about once every year.

Antibody can be administered on multiple occasions. Intervals between single dosages can be weekly, monthly or yearly. Intervals can also be irregular as indicated by measuring blood levels of the antibody in the subject. In some embodiments, the antibody can be administered as a sustained release formulation, in which case less frequent administration is required.

In some methods, the antibody of the invention is administered at a dosage to achieve a plasma or serum antibody concentration of 1-1000 µg/ml and in some methods 25-300 µg/ml. For example, the antibody of the invention can be administerd at a dosage to achieve a plasma or serum level of about 1-1000 µg/ml, 1-900 µg/ml, 1-800 µg/ml, 1-700 µg/ml, 1-600 µg/ml, 1-500 µg/ml, 1-400 µg/ml, 1-300 µg/ml, 1-200 µg/ml, 1-100 µg/ml, 10-500 µg/ml, 10-400 µg/ml, 10-300 µg/ml, 10-200 µg/ml, 10-100 µg/ml, 100-400 µg/ml, 100-300 µg/ml, or 100-200 µg/ml, inclusive of all values and ranges therebetween. For example, the antibody of the invention can be administerd at a dosage to achieve a plasma or serum level of about 1 µg/ml, about 5 µg/ml, about 10 µg/ml, about 15 µg/ml, about 20 µg/ml, about 25 µg/ml, about 30 µg/ml, about 35 µg/ml, about 40 µg/ml, about 45 µg/ml, about 50 µg/ml, about 55 µg/ml, about 60 µg/ml, about 65 µg/ml, about 70 µg/ml, about 75 µg/ml, about 80 µg/ml, about 85 µg/ml, about 90 µg/ml, about 95 µg/ml, about 100 µg/ml, about 105 µg/ml, about 110 µg/ml, about 115 µg/ml, about 120 mg µg/ml, about 125 µg/ml, about 130 µg/ml, about 135 µg/ml, about 140 µg/ml, about 145 µg/ml, about 150 µg/ml, about 155 µg/ml, about 160 µg/ml, about 165 µg/ml, about 170 µg/ml, about 175 µg/ml, about 180 µg/ml, about 185 µg/ml, about 190 µg/ml, about 195 µg/ml, about 200 µg/ml, about 205 µg/ml, about 210 µg/ml, about 215 µg/ml, about 220 mg µg/ml, about 225 µg/ml, about 230 µg/ml, about 235 µg/ml, about 240 µg/ml, about 245 µg/ml, about 250 µg/ml, about 255 µg/ml, about 260 µg/ml, about 265 µg/ml, about 270 µg/ml, about 275 µg/ml, about 280 µg/ml, about 285 µg/ml, about 290 µg/ml, about 295 µg/ml, or about 300 µg/ml.

In some methods, the antibody of the invention (e.g., humanized hu1B7 antibody and/or hu11E6 antibody) achieves a potency of at least about 1 EU/ug, at least about 2 EU/ug, at least about 3 EU/ug, at least about 4 EU/ug, at least about 5 EU/ug, at least about 6 EU/ug, at least about 7 EU/ug, at least about 8 EU/ug, at least about 9 EU/ug, at least about 10 EU/ug, at least about 15 EU/ug, at least about 20 EU/ug, at least about 25 EU/ug, at least about 30 EU/ug, at least about 35 EU/ug, at least about 40 EU/ug, at least about 45 EU/ug, at least about 50 EU/ug, at least about 55 EU/ug, at least about 60 EU/ug, at least about 65 EU/ug, at least about 70 EU/ug, at least about 75 EU/ug, at least about 80 EU/ug, at least about 85 EU/ug, at least about 90 EU/ug, at least about 95 EU/ug, at least or about 100 EU/ug. In some methods, the antibody of the invention (e.g., humanized hu1B7 antibody and/or hu11E6 antibody) achieves a potency of at least about 1 EU/ml, at least about 2 EU/ml, at least about 3 EU/ml, at least about 4 EU/ml, at least about 5 EU/ml, at least about 6 EU/ml, at least about 7 EU/ml, at least about 8 EU/ml, at least about 9 EU/ml, at least about 10 EU/ml, at least about 15 EU/ml, at least about 20 EU/ml, at least about 25 EU/ml, at least about 30 EU/ml, at least about 35 EU/ml, at least about 40 EU/ml, at least about 45 EU/ml, at least about 50 EU/ml, at least about 55 EU/ml, at least about 60 EU/ml, at least about 65 EU/ml, at least about 70 EU/ml, at least about 75 EU/ml, at least about 80 EU/ml, at least about 85 EU/ml, at least about 90 EU/ml, at least about 95 EU/ml, at least or about 100 EU/ml. EU stands for equivalent units as defined by the WHO polyclonal serum standard. In various embodiments, the antibody of the invention is able to maintain potency after at least about 1 day, about 2 days, about 3 days, about 4 days, about 5 days, about 6 days, about 1 week, about 2 weeks, about 3 weeks, about 4 weeks, about 5 months, about 6 months, about 7 months, about 8 months, about 9 months, about 10 months, about 11 months, or about 12 months.

Dosage and frequency vary depending on factors such as route of administration, dosage amount, the disease being treated, and the half-life of the antibody in the patient. The dosage and frequency of administration can vary depending on whether the treatment is prophylactic or therapeutic. In prophylactic applications, a relatively low dosage is administered at relatively infrequent intervals over a long period of time. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime. Illustrative dosing frequencies are once per day, twice per day, three times per day, once per week and once every two weeks. In some embodiments, dosing is once every two weeks.

The invention also provides kits that can simplify the administration of any agent described herein (e.g. the humanized antibodies with or without various combination agents). An illustrative kit of the invention comprises any composition described herein in unit dosage form. In one embodiment, the unit dosage form is a container, such as a pre-filled syringe, which can be sterile, containing any agent described herein and a pharmaceutically acceptable carrier, diluent, excipient, or vehicle. The kit can further comprise a label or printed instructions instructing the use of any agent described herein. The kit may also include a lid speculum, topical anesthetic, and a cleaning agent for the administration location. The kit can also further comprise one or more additional agent described herein. In one embodiment, the kit comprises a container containing an effective amount of a composition of the invention and an effective amount of another composition, such those described herein.

In some embodiments, the kit ma comprises a pre-filled syringe in unit dose form (e.g. an injector pen). In various embodiments, the kits are suited for use away from a traditional medical center, e.g. in the field, e.g. in the third world.

EXAMPLES

The following Examples are merely illustrative and are not intended to limit the scope or content of the invention in any way.

Example 1

Screening and Evaluation of Humanized 11E6 Heavy and Light Chain Variable Regions An expression plasmid construct encoding a chimeric 11E6 heavy chain was generated. The construct encoded an antibody with the mouse variable region followed by a human constant region. Specifically, the construct encoded SEQ ID NO: 13 fused to a human IgG1 heavy chain constant region. Similarly, an expression plasmid construct encoding a chimeric 11E6 light chain was generated. The construct encoded SEQ ID NO: 19 fused to a human Kappa light chain constant region. The two expression constructs also encoded a promoter, 5' untranslated sequence, and heterologous signal peptide for expression in, and secretion from CHO cells.

An expression plasmid construct encoding a chimeric 11E6 heavy chain was generated. The construct encoded an antibody with the mouse variable region followed by a human constant region. Specifically, the construct encoded SEQ ID NO: 13 fused to a human IgG1 heavy chain constant region. Similarly, an expression plasmid construct encoding a chimeric 11E6 light chain was generated. The construct encoded SEQ ID NO: 19 fused to a human Kappa light chain constant region. The two expression constructs also encoded a promoter, 5' untranslated sequence, and heterologous signal peptide for expression in, and secretion from CHO cells.

In analogous fashion, four expression plasmids encoding humanized 11E6 heavy chains were constructed utilizing SEQ ID NOs: 14, 15, 17, and 18. These were designated H1, H2, H3, and H4 respectively. Three expression plasmids encoding humanized 11E6 light chains were constructed utilizing SEQ ID NOs: 20, 21, and 23. These were designated L1, L2, and L3, respectively.

The heavy and light chain chimeric expression plasmids were co-transfected into CHO cells, which then secreted bivalent chimeric antibodies into the tissue culture medium. Similarly, all 12 combinations for the humanized heavy and light chain constructs were co-transfected into CHO cells. Specifically, H1 was co-transfected with L1, L2, L3, and L4; H2 was co-transfected with L1, L2, L3, and L4; and H3 was co-transfected with L1, L2, L3, and L4. Media was collected from each transfection, antibody levels in the samples were quantified, and binding to *pertussis* toxin was determined by ELISA. Both the chimeric constructs and all of the 12 humanized combinations yielded antibodies that specifically bound *pertussis* toxin. H1 and H4 in combinations with L2 and L3 generated the highest ELISA signals. The combination of H4 and L3 was chosen for further evaluation.

The dissociation constants (Kd) for the parental murine antibody, the chimeric antibody, the H4/L3 antibody were determined with a *pertussis* toxin-binding competition assay. In this assay, increasing concentrations of *pertussis* toxin are exposed to a constant amount of antibody. The amount of unbound antibody remaining is then quantified by ELISA. The dissociation constants for the three antibodies were nearly identical.

Thus, the 11E6 antibody was humanized without any loss of affinity versus the parental murine antibody.

Example 2

Screening and Evaluation of Humanized 1B7 Heavy and Light Chain Variable Regions The same evaluation was performed with the 1B7 chimeric sequences as well as 20 combinations of humanized 1B7 heavy and light chains. Expression plasmids were generated encoding the 1B7 chimeric heavy and light chains, SEQ ID NOs: 1 and 7, respectively. Expression plasmids for four 1B7 humanized heavy chains were prepared encoding SEQ ID NOs: 2, 3, 5, and 6, which were designated H1, H2, H3, H4, respectively. Expression plasmids for five 1B7 humanized light chains were prepared encoding SEQ ID NOs: 8, 9, 11, 12, and 10, which were designated L1, L2, L3, L4, and L5 respectively. For each expression plasmid the promoter, 5' untranslated region, signal peptide, and constant region (IgG1 and Kappa) were the same as was used for the 11E6 constructs in Example 1.

The chimeric heavy and light chain-encoding plasmids were co-transfected into CHO cells to generate a chimeric 1B7 antibody. Plasmids for each combination of humanized 1B7 heavy and light chain were also co-transfected into CHO cells to produce 20 different humanized 1B7 antibodies. The antibodies were then evaluated via the *pertussis* toxin binding ELISA as was done with 11E6 in Example 1. H1 and H2 in combinations with L3 and L4 produced the highest ELISA signals. H2/L3 was the combination chosen for further development. In the *pertussis* toxin competition assay, the dissociation constants for the parental murine 1 B7 antibody and the H2/L3 humanized 1B7 antibody were 0.15 and 0.16 nM respectively.

Thus, the 1 B7 antibody was humanized without any loss of affinity versus the parental murine antibody.

Example 3

Construction of Humanized Antibodies that Bind the *Pertussis* Toxin Protein

The two humanized antibodies identified in Examples 1 and 2, above, were produced in CHO cells. Specifically, for each antibody, two retroviral vectors were prepared, one encoding the heavy chain and the second encoding the light chain. For each antibody, the pair of retroviral vectors was used to repeatedly transduce and genetically modify a non-clonal pool of CHO cells. The recombinant CHO cells were then grown in shake flasks for two weeks. Each antibody was purified from the CHO cell tissue culture medium via a Protein A column. The humanized hu1B7 and hu11E6 antibodies were analyzed using SDS-PAGE gel (see FIGS. 1 and 3). In addition, the humanized hu1B7 and hu11E6 antibodies as well as a mixture of the two antibodies were also analyzed by size exclusion chromatography (see FIGS. 2, 4, and 5). Specifically, 500 µL of the antibodies in PBS (100 µg/mL) was incubated for 24 hour at 4° C. and the samples were run on a S200 column with PBS buffer.

Figure 2:
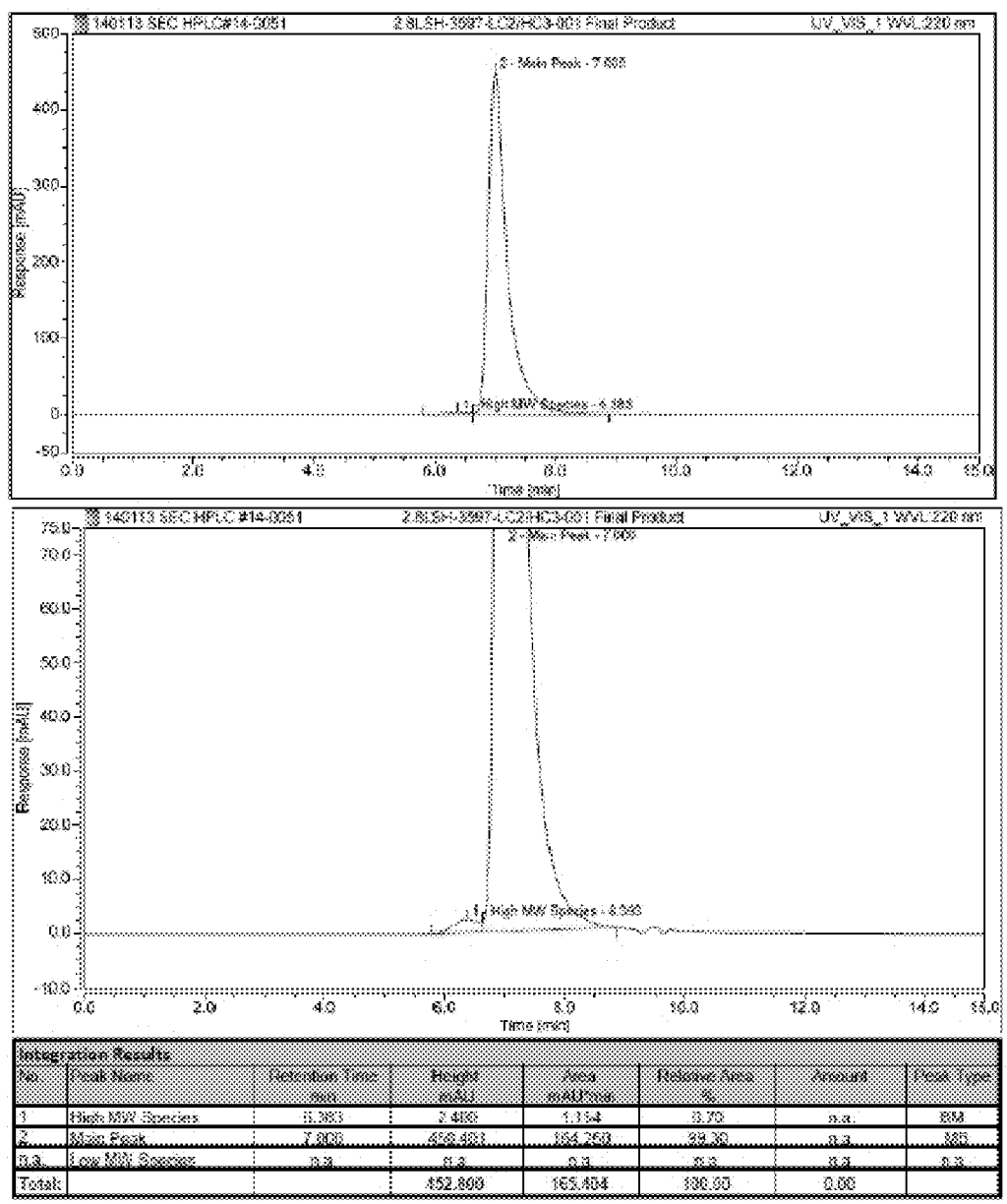
FIG. 2 shows size exclusion chromatography of a humanized hu1B7 antibody.
Figure 3:
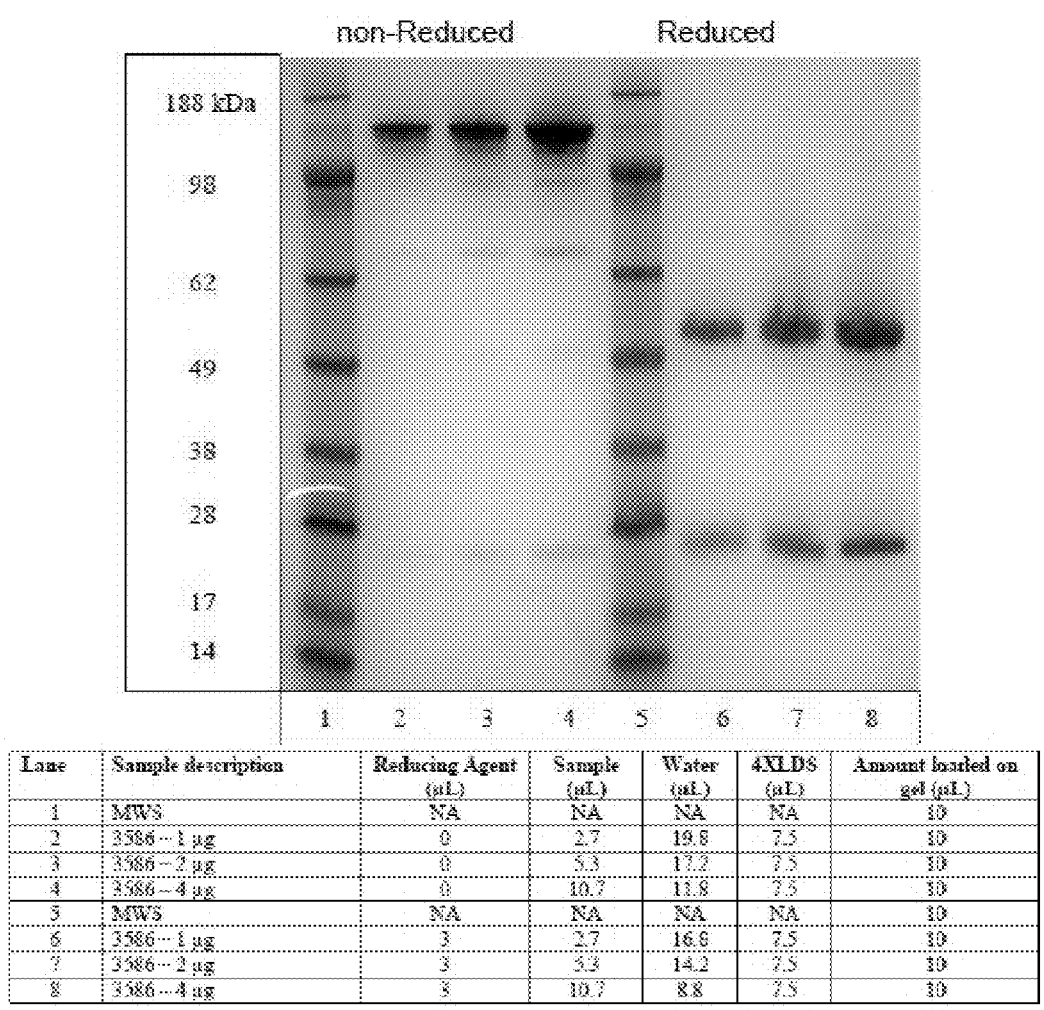
FIG. 3 shows a SDS PAGE gel of a humanized hu11E6 antibody under reducing and non-reducing conditions.
Figure 4:
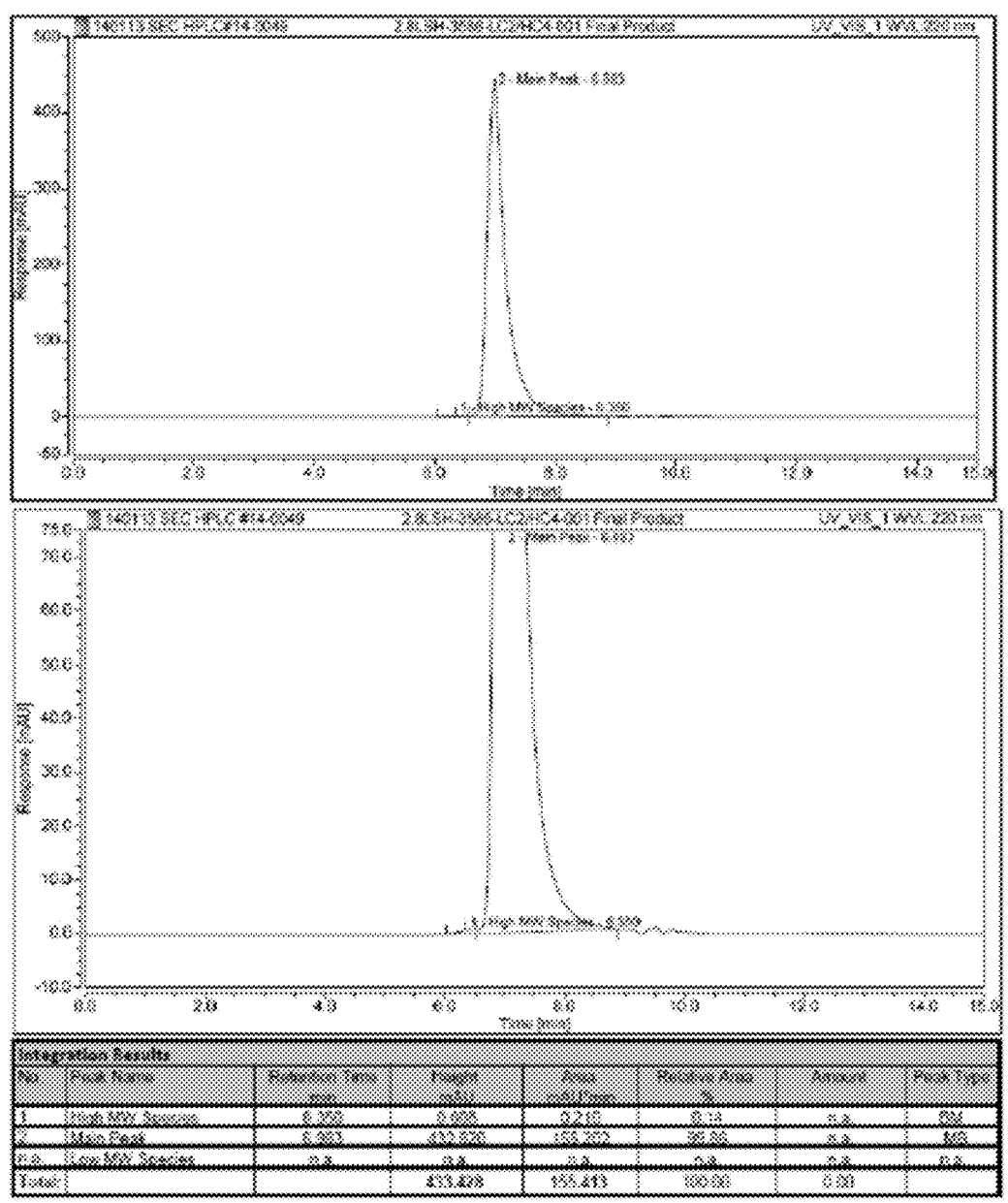
FIG. 4 shows size exclusion chromatography of a humanized hu11E6 antibody.

The humanized hu1B7 and hu11E6 antibodies were analyzed using SDS-PAGE gel (see FIGS. 1 and 3). In addition, the humanized hu1B7 and hu11E6 antibodies as well as a mixture of the two antibodies were also analyzed by size exclusion chromatography (see FIGS. 2, 4, and 5). Specifically, 500 µL of the antibodies in PBS (100 µg/mL) was incubated for 24 hour at 4° C. and the samples were run on a S200column with PBS buffer.

The following results were obtained for the humanized hu1B7 antibody: concentration: 5.78 mg/mL (using an A280 absorbance coefficient of 1.64 (mg/mL)$^{-1}$); endotoxin of <0.25 EU/mL (<0.04 EU/mg); and bioburden of <0.2 CFU/mL (Pass).

The following results were obtained for the humanized hu11E6 antibody: concentration: 5.62 mg/mL (using an A280 absorbance coefficient of 1.56 (mg/mL)$^{-1}$); endotoxin of <0.25 EU/mL (<0.04 EU/mg); and bioburden of <0.2 CFU/mL (Pass).

Figure 5:
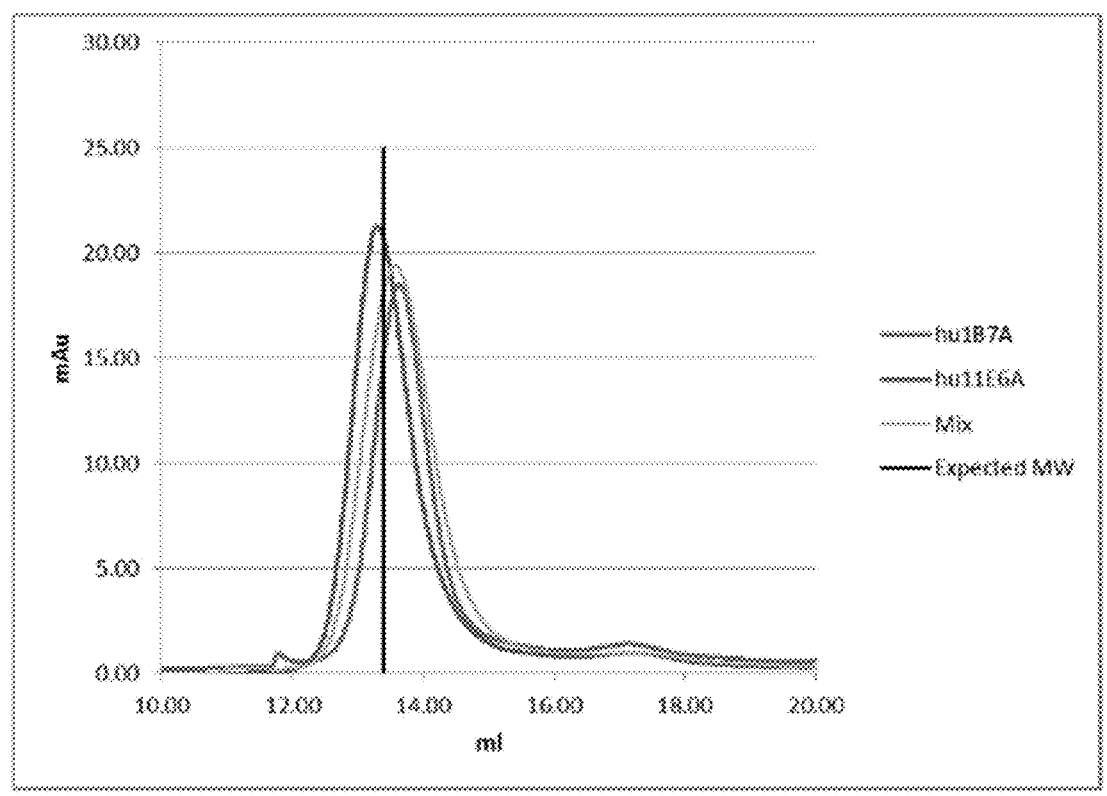
FIG. 5 shows size exclusion chromatography of, from left to right, a humanized hu1B7A antibody (third line), hu11E6A (first line), and a mixture of the two antibodies (second line). The results are measured in mL vs. mAu, and all lines are in comparison to the expected molecular weight (MW, perpendicular black line).
Figures 6A, 6B, 6C, 6D:
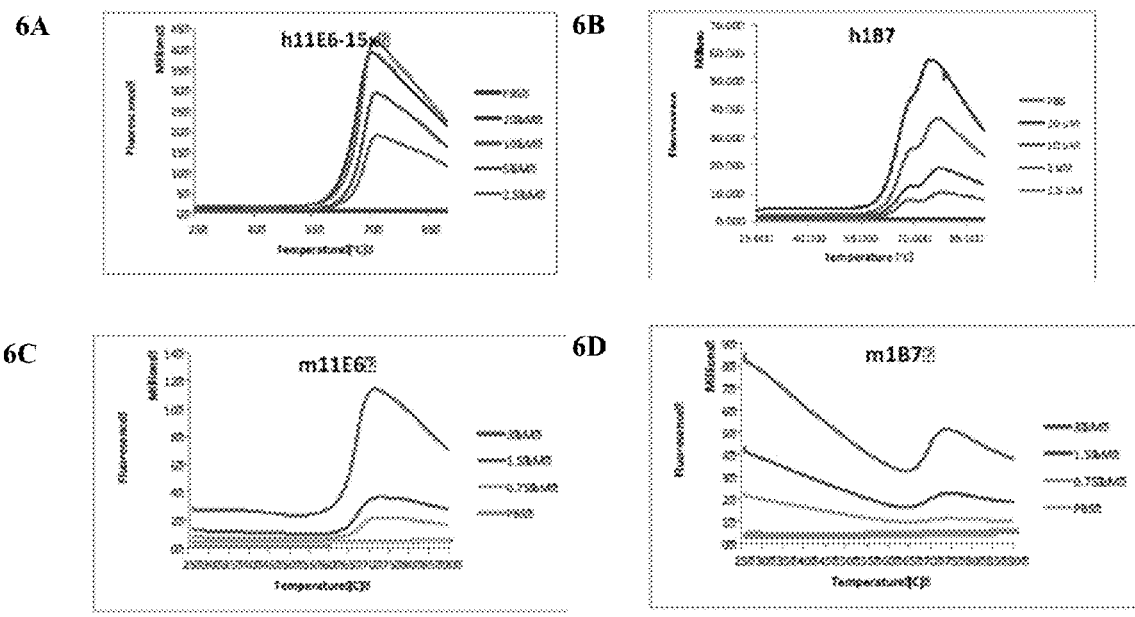
FIGS. 6A-6D show thermal unfolding plotted as Temperature (° C.) vs. Fluorescence for a humanized hu11E6 antibody, a humanized hu1B7 antibody, a murine m11E6 antibody, and a murine m1B7 antibody.

As shown in FIG. 5, the antibody preparations exhibited no apparent aggregation.

Example 4

Manufacturing of Humanized Antibodies

Large-scale manufacturing of the humanized hu1B7 and hu11E6 antibodies was carried out. Specifically, the humanized hu1B7 and hu11E6 antibodies were expressed in CHO cells using retroviral transduction technology followed by a monoclonal antibody purification process. Clones and backup clones for producing each antibody were identified. Each clone was characterized for expression, and the quality of the resultant antibodies was verified. The upstream process was scaled to 100 L for production of the hu1B7 antibody and to 250 L for production of the hu11E6 antibody. The upstream process utilized serum-free, chemically defined, and commercially available cell culture medium and feeds. The downstream process utilized a three-step purification by sequential chromatography (i.e., protein-A, anion exchange, and cation exchange). The manufacturing process also included a detergent-based virus inactivation step and tangential flow filtration into a PBS formulation buffer (pH 7.0) at 10 mg/mL. The two antibody preparations were sterilized through a 0.2 um filter and bulk filled into high density polyethylene bottles. The purified preparations were stored long-term at <−35° C. Yields of the humanized hu1B7 and hu11E6 antibodies were 47 and 70 grams, respectively. This yield is more than an order of magnitude higher compared to CHO cell manufacturing lines generated by standard plasmid transfection methods.

A panel of bio-analytical assays was conducted for batch analysis and stability studies of the manufactured antibodies. These methods included product-related tests such as A280 absorption reading, SDS-PAGE, SE-HPLC, IEF, and ELISA activity assay, as well as process-related tests such as analysis of host cell DNA and protein, endotoxin, bioburden, and mycoplasma. Appearance, osmolality, and pH were also measured. Both monoclonal antibodies exhibited superior characteristics in these assays.

Example 5

Characterization of the Humanized Antibodies

Thermal stability assays were used to assess the stability of the humanized hu11E6 and hu1B7 antibodies as well as their murine counterparts, as shown FIGS. 6A-6D.

Figure 7:
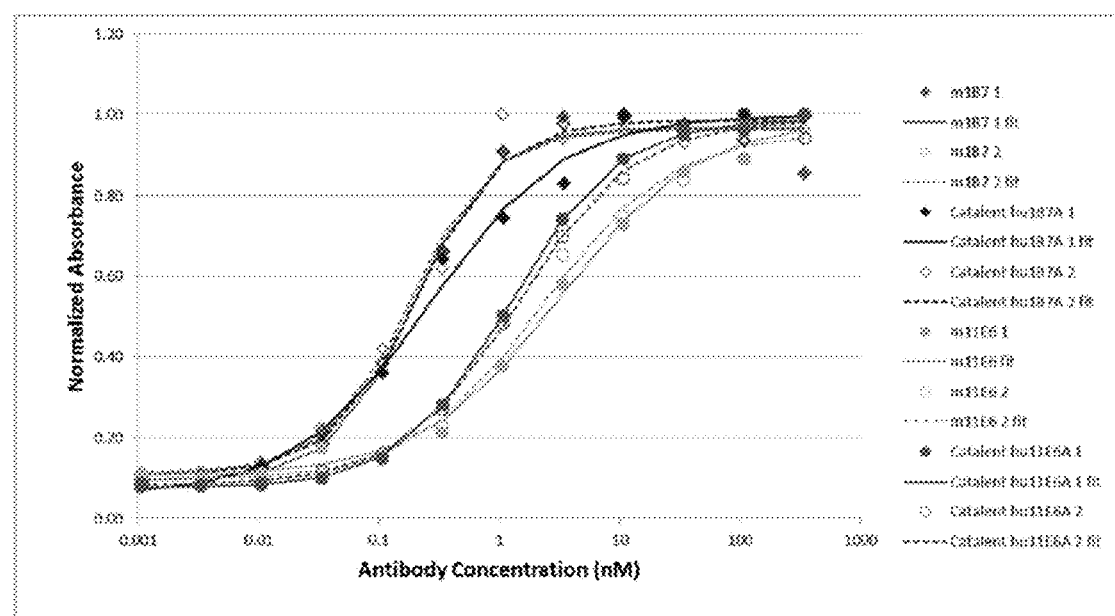
FIG. 7 shows the results of a *Pertussis* Toxin (PTx) ELISA assay which compares the PTx binding affinities of humanized hu1B7 and hu11E6 antibodies versus the mouse m1B7 and m11E6 antibodies. Results are shown as antibody concentration (nM) vs. normalized absorbance.

An ELISA assay was performed to determine the ability of the humanized hu11E6 and hu1B7 antibodies to bind the *pertussis* toxin protein (see FIG. 7). Specifically, the *pertussis* toxin protein was used for coating while anti-mouse-HRP or anti-human Fc-HRP were used as secondary antibodies. TMB(3,3',5,5'-Tetramethylbenzidine) was used as substrate for the assay. The following $EC_{50}$ (nM) data was obtained:

m1B7: 0.19±0.01;
hu1B7A: 0.23±0.04;
m11E6: 2.7±0.7; and
hu11E6A 1.3±0.2.

As indicated, the humanized hu11E6 and hu1B7 antibodies exhibited high affinity for the *pertussis* toxin protein that is either comparable to or superior to the murine antibodies.

Figure 8:
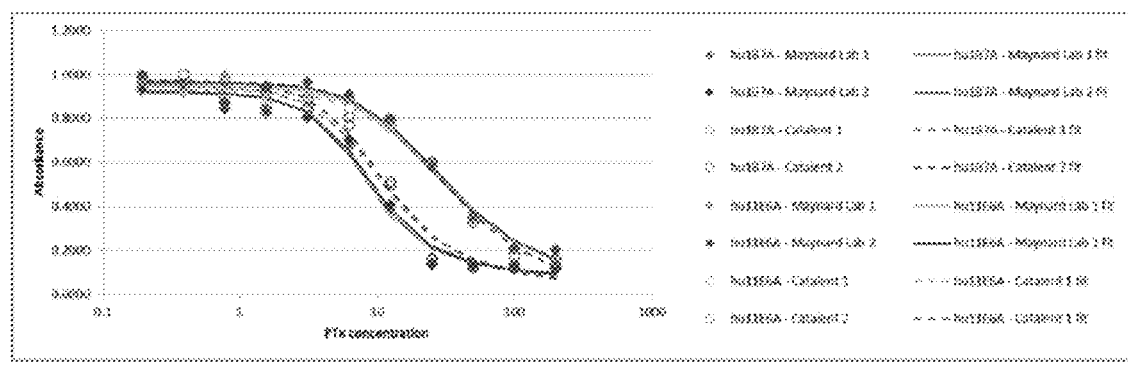
FIG. 8 shows the results of a Competition ELISA assay which determines the PTx binding affinities of the humanized hu1B7 and hu11E6 antibodies as produced in two different laboratories. Results are shown as PTx concentration vs. absorbance.

FIG. 8 shows the results of a Competition ELISA assay which determines the binding affinities of the humanized hu1B7 and hu11E6 antibodies. The dissociation constants were assayed on antibody preparations generated in an academic research lab compared to those generated at a Contract Research Organization (CRO). For the ELISA, the *pertussis* toxin protein was used for coating while anti-human Fc-HRP were used as a secondary antibody. TMB (3,3',5,5'-Tetramethylbenzidine) was used as a substrate.

The following Kd (nM) data were obtained:
Research lab hu1B7A=1.7±0.2;
CRO hu1B7A 2.6±0.1;
Research lab hu11E6A 10.7±0.3; and
CRO hu11E6A 11.3±0.4.

The binding affinities of the humanized hu1B7 and hu11E6 antibodies were also measured by BIAcore, and the following Kd data were obtained as shown in Table 1.

TABLE 1

|  | Kd, competition ELISA (nM); n# x exp | Kd, BIAcore (nM) ch12 | on-rate BIAcore $(sec^{-1} M^{-1})$ | Off-rate, BIAcore $(sec^{-1})$ | Melting temp (° C.) |
|---|---|---|---|---|---|
| m1B7 | 0.4 ± 0.2 | 0.7 ± 0.2 (0.32) | 1.7 ± 0.3 ×10$^8$ | 1.2 ± 0.3 ×10$^{-4}$ | 74.8 ± 0.7 |
| ch1B7 | 0.5 ± 0.3 | 0.5 ± 0.4 (0.74) | 1.5 ± 0.1 ×10$^8$ | 0.8 ± 0.5 ×10$^{-4}$ | 78.1 ± 0.5 |
| hu1B7A | 1.2 ± 0.7 | 0.7 ± 0.5 (0.75) | 0.9 ± 0.2 ×10$^8$ | 0.7 ± 0.5 ×10$^{-4}$ | 79.0 ± 0.3 |
| m11E6 | 5 ± 1 | 0.2 ± 0.2 * (0.13) | 0.8 ± 0.1 ×10$^8$ | 0.2 ± 0.1 ×10$^{-4}$ * | 67.3 ± 0.4 |
| ch11E6 | 5 ± 2 |  |  |  | 69.4 ± 0.4 |
| hu11E6 | 7 ± 3 | 0.4 ± 0.7 * (0.26) | 0.65 ± 0.05 ×10$^8$ | 0.3 ± 0.4 ×10$^{-4}$ * | 74.4 ± 0.4 |

Figure 9:
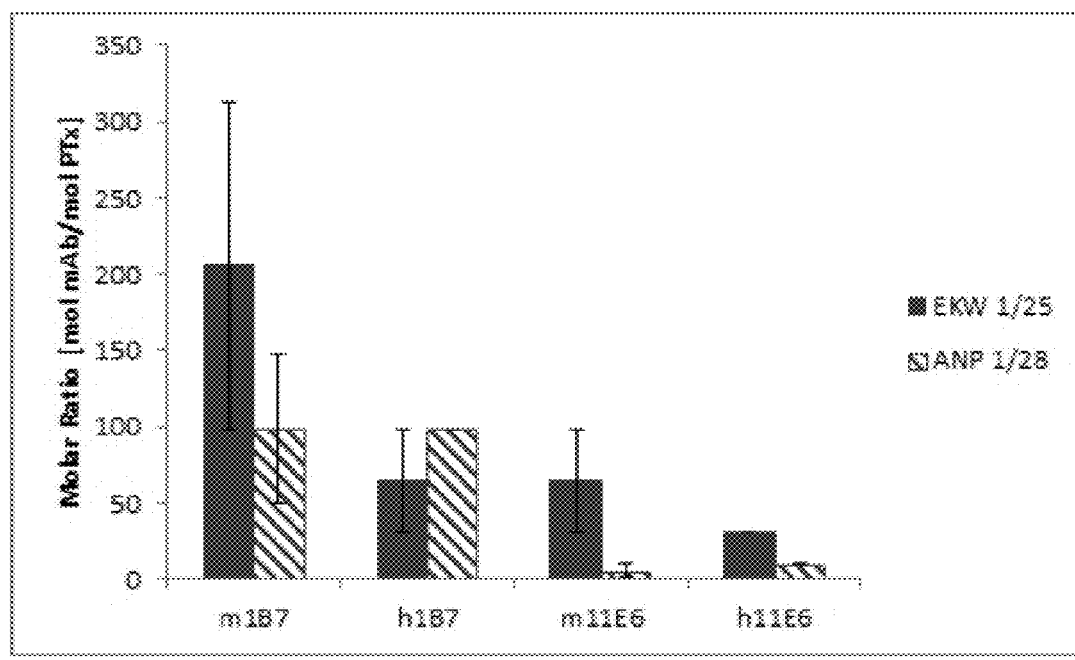
FIG. 9 shows the results of a CHO cell in vitro protection assay that measures the ability of the humanized hu1B7 and hu11E6 antibodies to neutralize the *pertussis* toxin protein. Results as shown in molar ratios (mol mAb/mol PTx).

A CHO cell in vitro protection assay was conducted to compare the neutralization activity of the humanized hu1B7 and hu11E6 antibodies. The assays was performed by two different technicians (see FIG. 9). Specifically, this assay measured the ability of the antibodies to neutralize the *pertussis* toxin protein. As shown in FIG. 9, the humanized and mouse antibodies were comparable at neutralizing the *pertussis* toxin protein.

Figure 10:
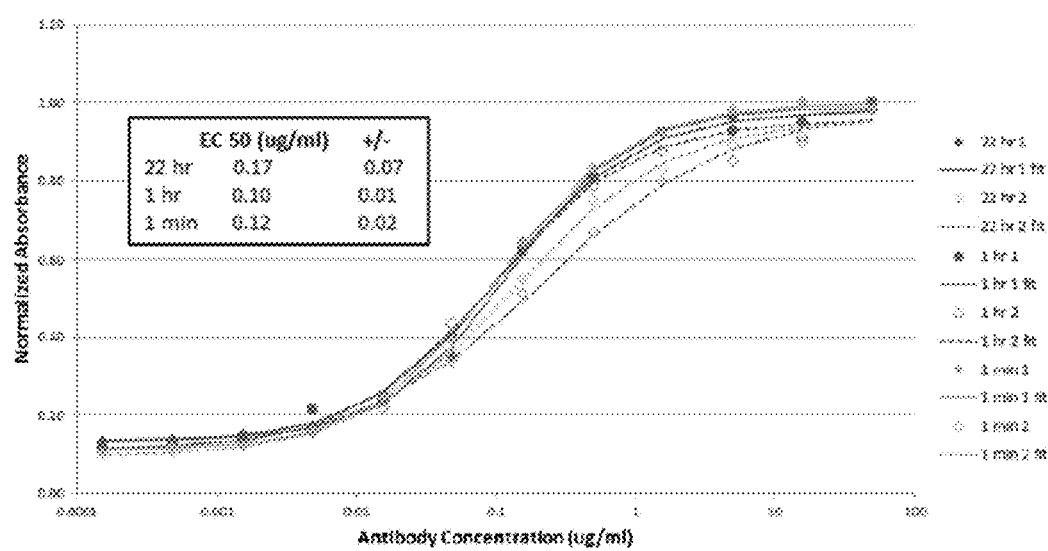
FIG. 10 shows the results of a PTx toxin ELISA assay along with the $EC_{50}$ (μg/mL) values for a mixture of the humanized hu1B7 and hu11E6 antibodies. The antibodies were mixed and stored at 4° C. for 1 minute, 1 hour, and 22 hours. Results are shown as antibody concentration (μg/mL) vs. normalized absorbance.
Figure 11:
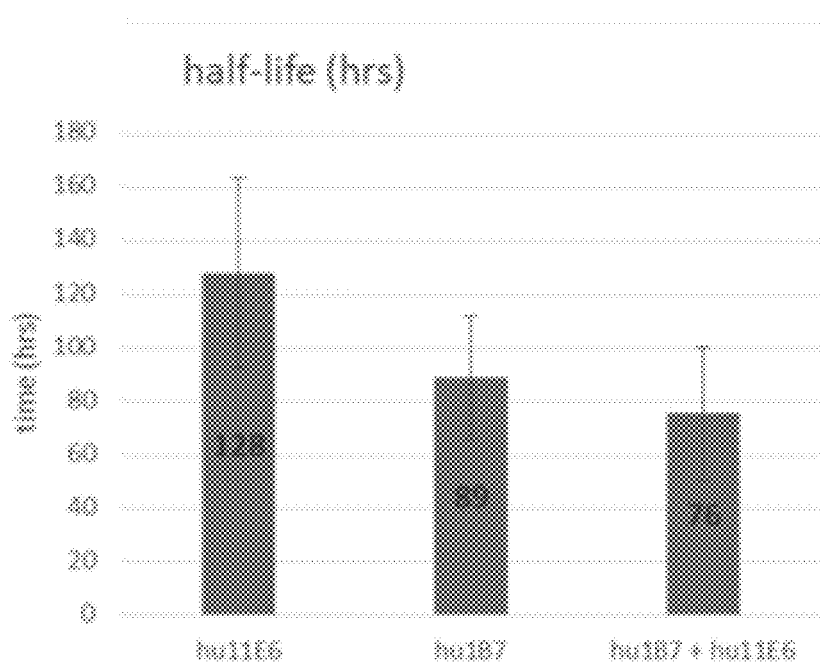
FIG. 11 demonstrates the elimination (β) half-lives (t½β) of a humanized hu11E6 antibody, a humanized hu1B7 antibody, and a mixture of the humanized hu1B7 and humanized hu11E6 antibodies. All half-lives were determined in mice.
Figure 12:
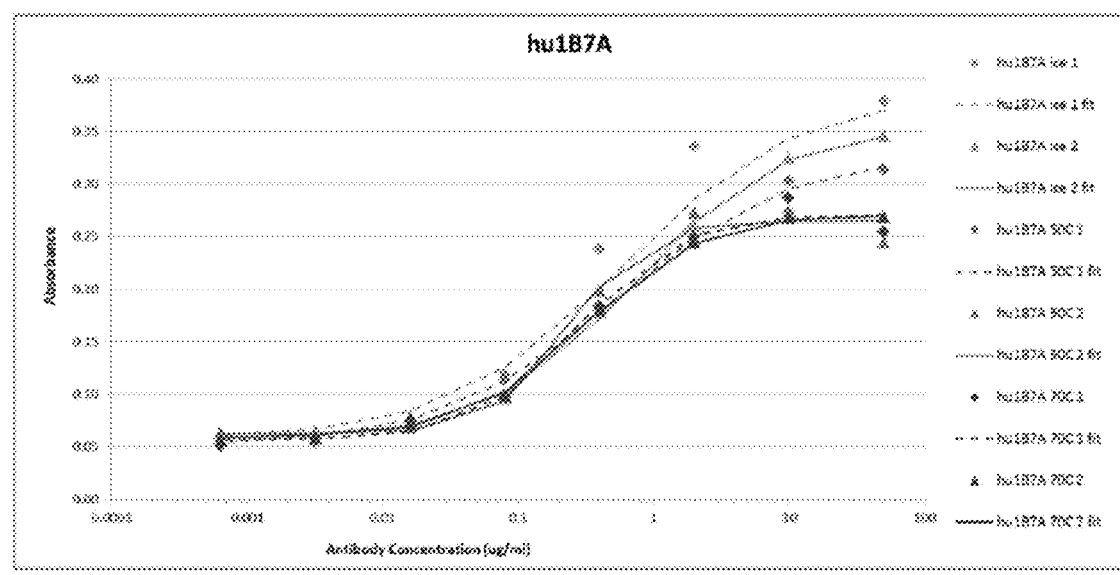
FIG. 12 shows the results of a PTx toxin ELISA assay which determines the effects of heat treatment on the activity of the humanized hu1B7A antibody. Specifically, 50 μg/mL of the antibody were incubated in PBS for 30 minutes on ice, at 50° C., or at 70° C., and quenched on ice for 1 minute. The results are measured as antibody concentration (μg/mL) vs. absorbance.
Figure 13:
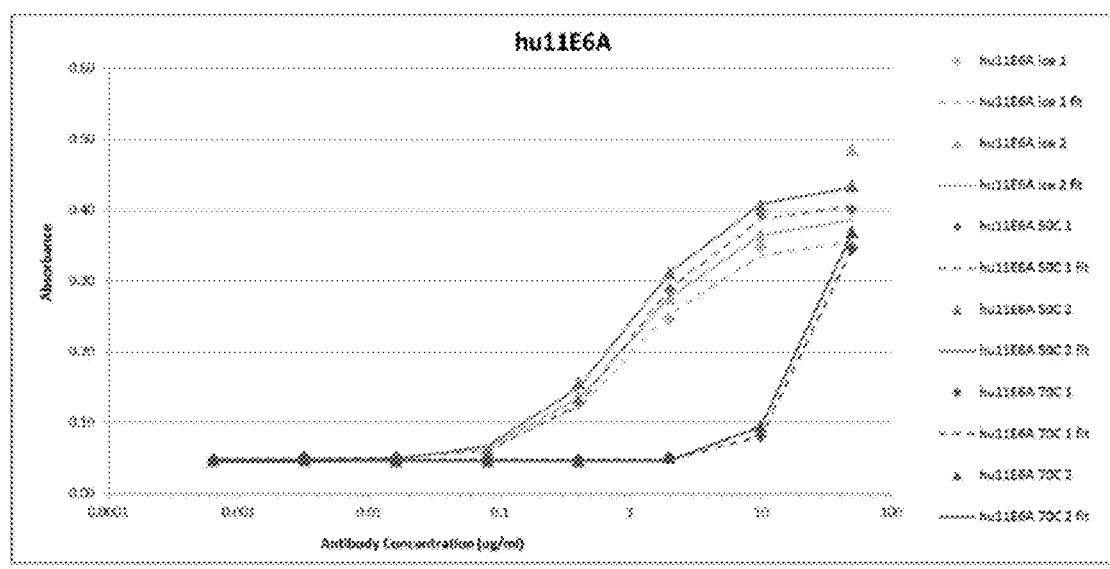
FIG. 13 shows the results of a PTx toxin ELISA assay which determines the effects of heat treatment on the activity of the humanized hu11E6A antibody. Specifically, 50 μg/mL of the antibody were incubated in PBS for 30 minutes on ice, at 50° C., or at 70° C., and quenched on ice for 1 minute. The results are measured as antibody concentration (μg/mL) vs. absorbance.

A mixture of the humanized 11E6 and 1B7 antibodies was prepared by mixing the antibodies and storing at 4° C. for 1 minute, 1 hour, and 22 hours. The binding affinity of the mixture for the *pertussis* toxin protein was evaluated using an ELISA assay as previously described (see FIG. 10). The following $EC_{50}$ (nM) data was obtained:

1 minute=0.12±0.02;

1 hour=0.10±0.01; and 22 hours=0.17±0.07.

As evidenced by the $EC_{50}$ data, there was no apparent adverse interaction between the humanized hu1B7 antibody and the humanized hu11E6 antibody upon storage as a mixture that would interfere with their binding affinities for the *pertussis* toxin protein.

Table 2 below summarizes a pharmacokinetic (PK) analysis of the humanized hu1B7 antibody as compared to the murine m1B7 antibody.

Figure 14:
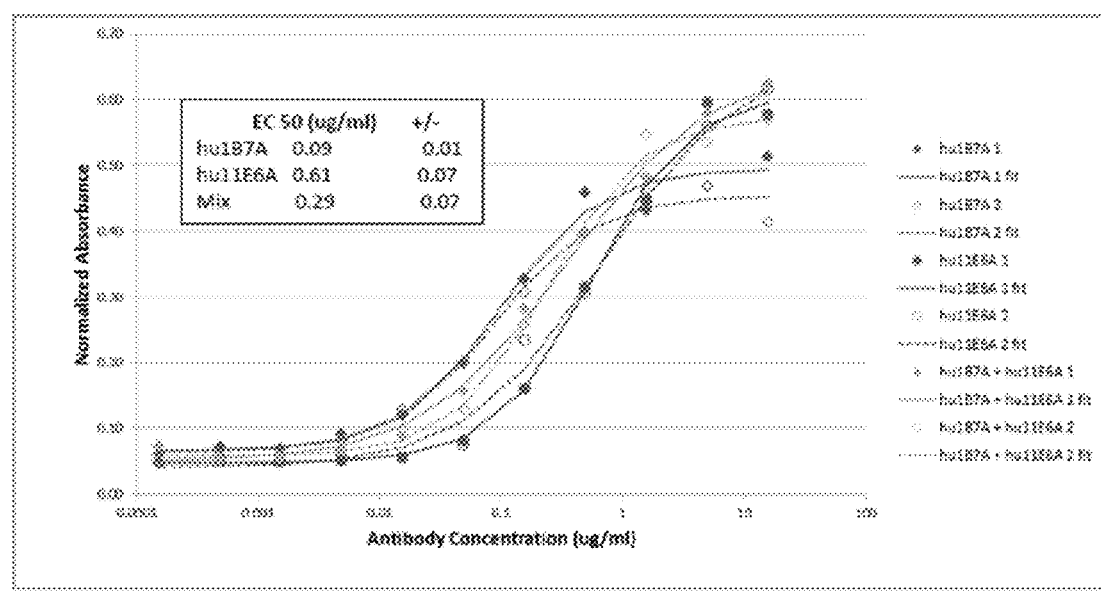
FIG. 14 shows the results of a PTx toxin ELISA assay along with the $EC_{50}$ (μg/mL) values for a humanized hu1B7A antibody, a humanized hu11E6A antibody and a mixture of the two antibodies. Results are shown as antibody concentration (μg/mL) vs. normalized absorbance.
Figure 15:
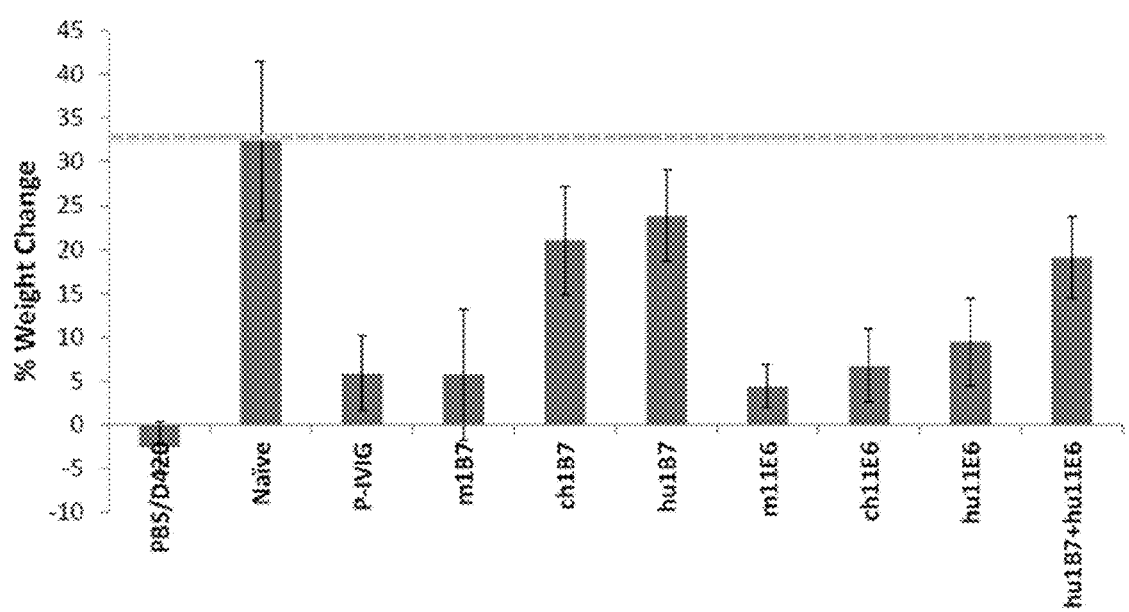
FIG. 15 shows the efficacy of the humanized 11E6 and 1B7 antibodies in treating mice infected with the *B. pertussis* D420 strain (as measured by % weight gain). Mice were treated with either PBS, P-IVIG, a murine m1B7 antibody, a ch1B7 antibody, a humanized hu1B7 antibody, a murine m11E6 antibody, a ch11E6 antibody, a humanized hu11E6 antibody, or a mixture of humanized hu1B7 and hu11E6 antibodies, and their body weight was measured at 10 days post post-infection. Uninfected naive mice served as baseline control.
Figures 16A, 16B:
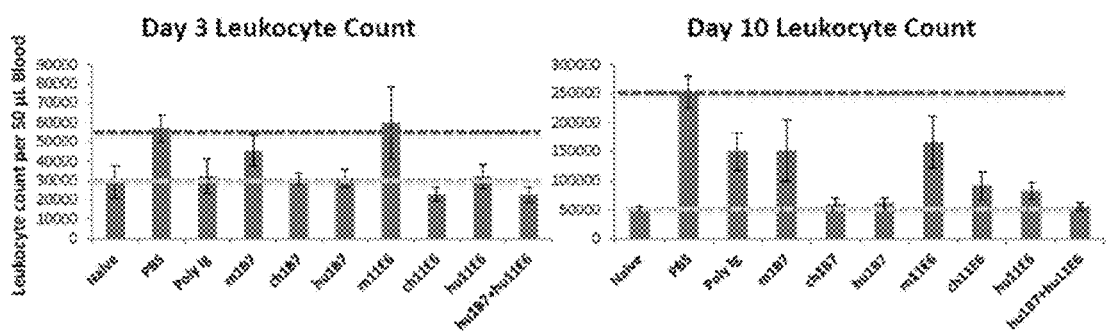
FIGS. 16A and 16B show the efficacy of the humanized 11E6 and 1B7 antibodies in treating mice infected with the *B. pertussis* D420 strain (as measured by leukocyte count per 50 μL of blood). Mice were treated with either PBS, P-IVIG, a murine m1B7 antibody, a ch1B7 antibody, a humanized hu1B7 antibody, a murine m11E6 antibody, a ch11E6 antibody, a humanized hu11E6 antibody, or a mixture of humanized hu1B7 and hu11E6 antibodies, and their blood leukocyte count was evaluated at 3 days and 10 days post infection. Uninfected naive mice served as baseline control.
Figure 17:
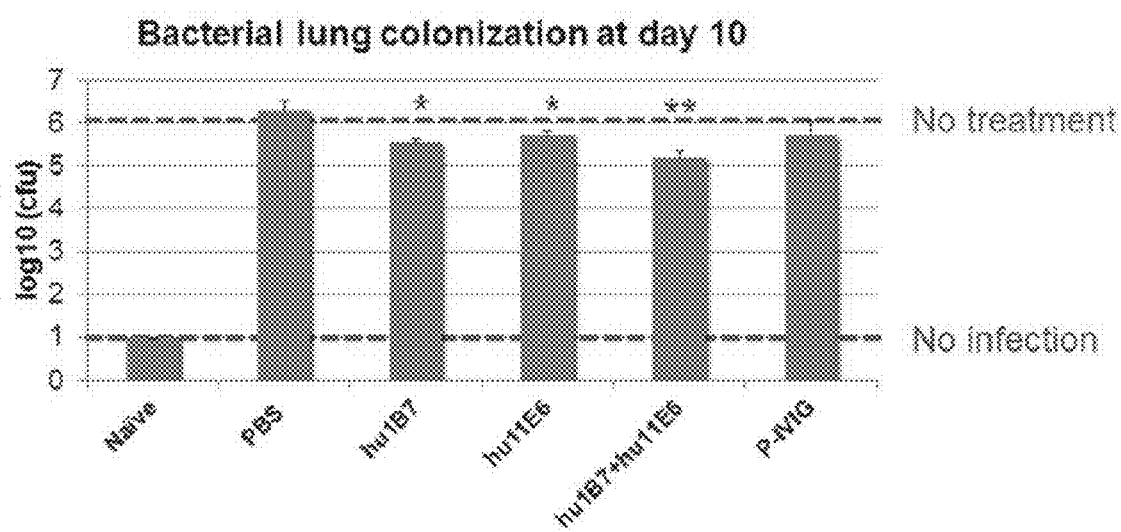
FIG. 17 shows the efficacy of the humanized 11E6 and 1B7 antibodies in reducing the colonization of mouse lungs by the *B. pertussis* bacteria.
Figures 18A, 18B:
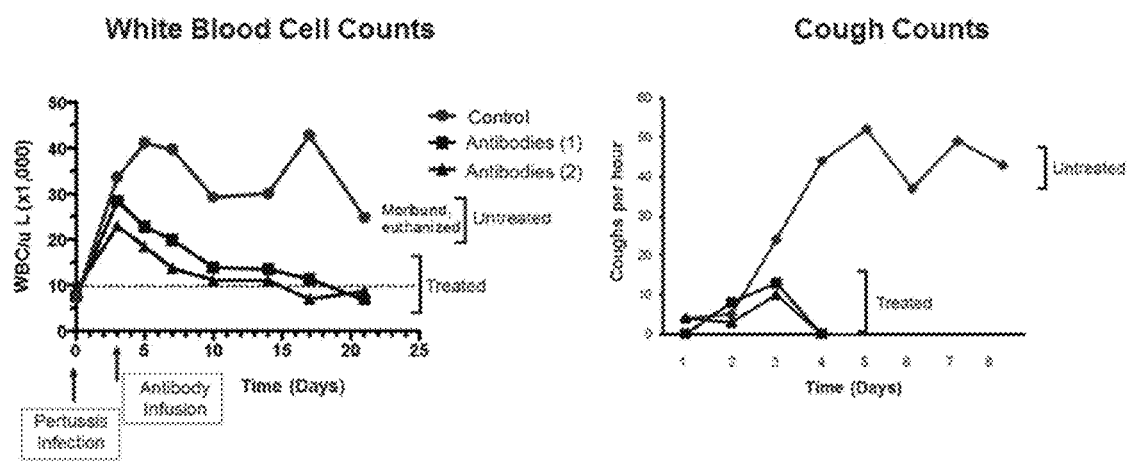
FIGS. 18A and 18B show the therapeutic effect of a cocktail of the humanized 11E6 and 1B7 antibodies on *B. pertussis* infected baboons. Specifically, white blood cell counts and cough counts were assessed.
Figure 19:
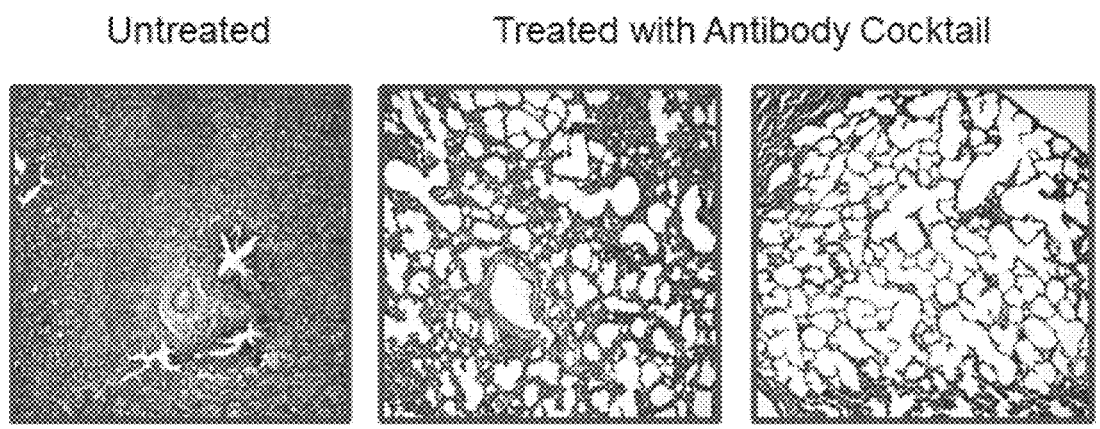
FIG. 19 shows the pathology sections from the lungs of *B. pertussis* infected baboons that were treated with the humanized 11E6 and 1B7 antibodies.
Figures 20A, 20B:
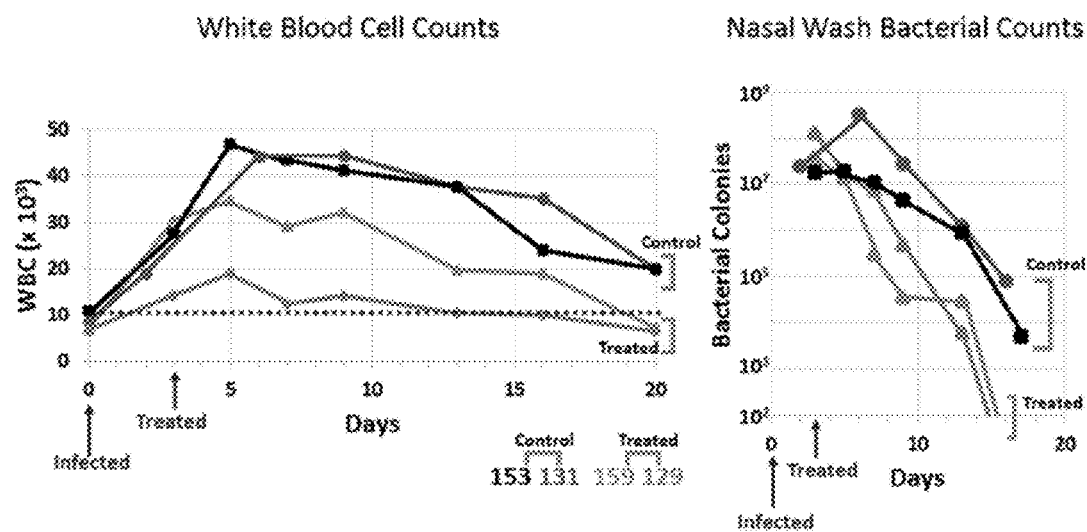
FIGS. 20A and 20B show the therapeutic effect of a cocktail of the humanized 11E6 and 1B7 antibodies on *B. pertussis* infected baboons. Specifically, white blood cell counts and nasal wash bacterial counts were assessed.
Figure 21A:
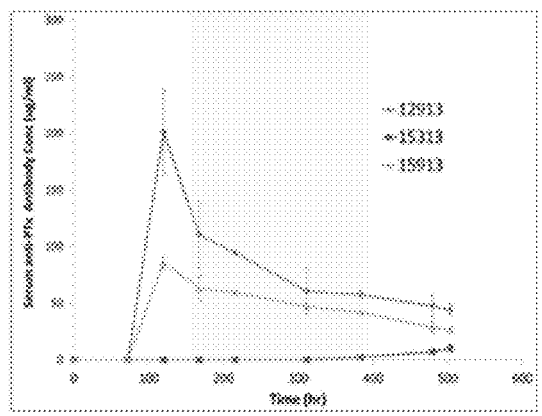
FIGS. 21A and 21B show the antibody serum concentration and antibody half-life, respectively, of the humanized 11E6 and 1B7 antibodies in two *B. pertussis* infected baboons (i.e., baboon #12913 and 15913). The timing shown on the Y-axis of FIG. 21A is as shown in FIGS. 20A and 20B (i.e. infection at time=0, treatment at 3 days).
Figure 21B:
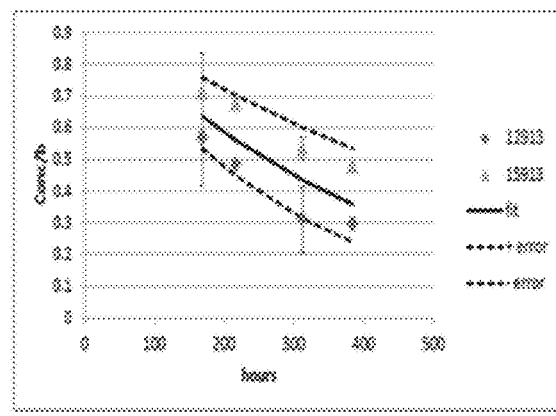

TABLE 2

| | Mass injected (ug) | $AUC_{0->}\infty$ (ug * hr/ml) | $\beta_{m1B7}$ ($hr^{-2}$) | $t_{1/2\beta}$ (hr) | b (ug/ml) | Est. conc. @ t = 3 days (ug/ml) | Est. conc. @ t = 7 days (ug/ml) | Est. conc. @ t = 10 days (ug/ml) |
|---|---|---|---|---|---|---|---|---|
| m1B7 | 1* | 107.9 | 0.0033 | 210 | 0.36 | 0.28 | 0.21 | 0.16 |
| | 5* | 539.8 | 0.0033 | 210 | 1.8 | 1.4 | 1.03 | 0.82 |
| | 20* | 2,159 | 0.0033 | 210 | 7.1 | 5.6 | 4.1 | 3.2 |
| | 140 | 15,114 | 0.0033 | 210 | 49.9 | 39.3 | 28.7 | 22.6 |
| h1B7 | 1 | 25 ± 7 | 0.0078 | 89 | 0.20 ± 0.08 | 0.11 ± 0.03 | 0.05 ± 0.02 | 0.03 ± 0.01 |
| | 5 | 127 ± 38 | 0.0078 | 89 | 1.0 ± 0.4 | 0.6 ± 0.2 | 0.26 ± 0.08 | 0.15 ± 0.06 |
| | 20 | 509 ± 149 | 0.0078 | 89 | 3.9 ± 1.6 | 2.2 ± 0.7 | 1.0 ± 0.3 | 0.6 ± 0.2 |

From the PK analysis, it was determined that 5 ug of the murine m1B7 antibody fully protected mice infected with *B. pertussis* and had an elimination half-life of about 210 hours. In comparison, 20 ug of the humanized hu1B7 had an elimination half-life of about 89 hours (see FIG. 11) and had a similar blood concentration through day 7. Accordingly, the 20 ug dose of the humanized hu1B7 antibody was expected to protect infected mice in a similar manner to the 5 ug dose of the murine m1B7 antibody. Further, as shown in FIG. 10, the humanized 11E6 antibody had an elimination half-life of about 128 hours, while a mixture of the two antibodies had an elimination half-life of about 76 hours.

An ELISA assay was conducted to determine whether heat affected the binding affinities of the humanized hu1B7A and hu11E6A antibodies for the *pertussis* toxin protein (see FIGS. 12 and 13). The ELISA assay was performed as previously described. Particularly, 50 μg/mL of the antibody was incubated in PBS for 30 minutes on ice, at 50° C., or at 70° C. and quenched on ice for 1 minute. As shown in FIG. 12, the humanized hu1B7A antibody remained stable and did not irreversibly unfold after 30 minutes of heating at 50° C. or 70° C. As shown in FIG. 13, the humanized hu11E6A antibody remained stable after 30 minutes of heating at 50° C. but irreversibly unfolded after heating at 70° C.

An ELISA assay was conducted to compare the binding affinities of the individual humanized hu1B7A or hu11E6A antibody as compared to the mixture of the two antibodies (see FIG. 14). The ELISA assay was performed as previously described. The following $EC_{50}$ (nM) data were obtained:

hu1B7A: 0.09±0.01;

hu11E6A: 0.61±0.07; and mixture of hu1B7A and hu11E6A: 0.29±0.07.

Example 6

Evaluation of the Humanized Antibodies in Treating *B. pertussis* Infections in Mice The efficacy of the humanized hu1B7 and hu11E6 antibodies in treating *B. pertussis* infections was evaluated in a mouse model.

Specifically, mice infected with the *B. pertussis* D420 strain were treated with the humanized hu1B7 antibody, the humanized hu11E6 antibody, and a mixture of the two antibodies. The infected mice were subsequently analyzed for their body weight and white blood cell count. As shown in FIG. 15, treatment with each humanized antibody separately or in combination allowed for greater weight gain in the infected mice than those treated with PBS or with the murine m1B7 antibody. FIGS. 16A-16B show that treatment with the humanized antibodies also significantly reduced the white blood cell count of the infected mice at 3 and 10 days post infections.

The effect of antibody treatments on bacterial lung colonization was also assessed. Specifically, mice were treated with either PBS, P-IVIG, the humanized hu1B7 antibody, the humanized hu11E6 antibody, or a mixture of the two antibodies. Bacterial lung colonization was evaluated at 10 days postinfection. Uninfected naive mice served as the baseline control. Infected mice were euthanized by $CO_2$ inhalation on day 10 postinfections, and the respiratory tract was excised for enumeration by serial plating on Regan Lowe agar supplemented with 10% sheep's blood (Hemostat Resources) containing 40 ug/ml cephalexin. Colonies were counted after 5 days at 37° C. As shown in FIG. 17, mice treated with the antibodies displayed a significant drop in bacterial colonization compared to the untreated controls (PBS) or the P-IVIG-treated animals. $P<0.05$ (*) for animals treated with hu1B7, and hu11E6 alone, and $P<0.01$ (**) for animals treated with the combination of hu1B7 and 11E6.

Altogether, these data supports the in vivo efficacy of the humanized hu11E6 and hu1B7 antibodies in treating *B. pertussis* infection.

Example 7

Evaluation of the Humanized Antibodies in Treating B. pertussis Infections in Baboons The efficacy of the humanized hu1B7 and hu11E6 antibodies in treating *B. pertussis* infections was evaluated in a baboon model.

Specifically, weanling (6-9 month old) male and female baboons (*Papio anubus*, olive baboons) of about 2-3 kg in weight were infected by intranasal administration of the *B. pertussis* D420 strain and treated intravenously with the humanized hu1B7 and the humanized hu11E6 antibodies. The infected baboons were analyzed for clinical signs of illness (for example, coughing, weight and temperature), white blood cell counts, and/or nasal carriage levels of *B. pertussis.*

For the *B. pertussis* infection, a *B. pertussis* strain, D420, was suspended in PBS at $10^9$-$10^{10}$ cfu/ml. One ml was delivered via endotracheal tube to the top of the baboon trachea. 0.5 ml was delivered via an intranasal catheter to the back of each naris. Baboons were then placed in a sitting position for 3 minutes. For the phlebotomy, <5 ml of blood was collected via venipuncture with a butterfly catheter and was aliquoted into tubes for white blood cell determination and serum separation. Throughout the study, the baboons were anesthetized with an intramuscular injection of ketamine for activities including antibody infusions, *B. pertussis* infection, blood draws, nasopharyngeal washes, and clinical observations. These activities were combined whenever possible to minimize the use of anesthesia.

Two studies were conducted. In one, three baboons were each infected with $6\times10^9$ CFU of *B. pertussis*. Three days later, two of the animals were treated with both the humanized hu1B7 and the humanized hu11E6 antibodies, and the third animal remained untreated. Three weeks after infection, the untreated animal became moribund and was euthanized. The other two treated animals were also euthanized. Histological evaluation of lung sections were performed. In the second study, four baboons were infected with $4\times10^9$ CFU of *B. pertussis* and three days later, two of the animals were treated with both the humanized hu1B7 and the humanized hu11E6 antibodies, and two animals remained untreated. The antibodies were administered via intravenous injection, and each was used at dose of 20 mg/kg.

As shown in FIG. 18A, the untreated animal developed a leukocytosis that peaked above 40,000 cells per uL. In this animal, the elevated white count persisted. Three weeks after infection, the animal suddenly became moribund and was euthanized. In contrast, the white counts in the treated animals began to decrease within two days after antibody administration. The counts continued to drop and were nearly normal within one week. These animals remained healthy and were sacrificed in parallel with the untreated animal. The cough counts displayed a similar pattern (FIG. 18B). The control animal displayed a rapid increase in coughing from Day 3 to the end of the study peaking at 5 days at over 50 coughs per hour. In contrast, the two treated animals showed increasing coughing up to Day 3 (treatment) which rapidly declined to zero by Day 4.

The lungs of the infected baboons were evaluated by histopathological examination (FIG. 19). At necropsy, the untreated animal was shown to have a consolidated right lung. Histopathology of this lung demonstrated severe subacute to chronic, diffuse interstitial pneumonia with abscess formation and moderate interstitial fibrosis. The left lung revealed a more moderate interstitial pneumonia with much less scarring and no evidence of abscess formation. There also was moderate chronic multifocal organizing pleuritis with an area of abscess formation. In contrast, at necropsy, the lungs of the two treated animals were grossly normal. Histopathology sections from the right lung of one treated animal revealed very mild chronic interstitial pneumonia with evidence of very mild interstitial fibrosis. The left lung was essentially normal in appearance. For the other treated animal the right and left lungs had an essentially normal appearance with the only finding being mild to moderate lymphoid hyperplasia of the bronchial associated lymphoid tissue (BALT). Thus, the untreated animal demonstrated changes of severe pneumonia, whereas the lungs of the treated animals were either normal or demonstrated very mild pneumonia.

The white blood cell counts and nasal bacterial counts of the infected baboons were assessed (FIGS. 20A and 20B). The untreated animals developed a leukocytosis that peaked well above 40,000 cells per uL. In these animals, the elevated white count persisted and was not normalized by Day 20. In contrast, the two treated animals displayed an elevated white blood cell count at the time of antibody treatment on Day 3, however, the white blood cell count never reached levels observed with the untreated animals, and by Day 20, both treated animals white blood cell counts had returned to normal levels. Similarly, the *B. pertussis* bacterial cell counts in the nasal washes demonstrated a similar amount of bacteria at Day 3 (treatment). Following antibody treatment, the bacterial levels in the nose displayed a rapid decline for the antibody cocktail treated animals, while the bacterial counts in the nose of the two control animals remained well above $10^3$ cfu by Day 18.

The serum concentration and half-life of the humanized hu1B7 and the humanized hu11E6 antibodies were also measured. To measure the amounts of the humanized 1B7 and 11E6 antibodies in the baboon serum following intravenous administration of 20 mg/kg of each antibody, blood samples were collected at various time points, serum isolated, and serum samples were used in the anti-*pertussis* toxin (PTx) ELISA as described previously in Example 4. Specifically, the *pertussis* toxin protein was used for coating while anti-human Fc-HRP were used as secondary antibodies. TMB(3,3',5,5'-Tetramethylbenzidine) was used as substrate for the assay. Two treated baboons were used for this analysis (i.e., baboon #12913 and 15913). FIG. 21A shows the antibody serum concentration of the humanized hu1B7 and the humanized hu11E6 antibodies as calculated by the equation:

$$\text{Serum Conc}=ae^{-\alpha t}+be^{-\beta t}$$

FIG. 21B shows the antibody half-life of the humanized antibodies.

In summary, both humanized antibodies, either individually or in combination, mitigated the weight loss, leukocytosis, and pulmonary bacterial burdens in a mouse *pertussis* model. Moreover, in the baboon model, the combination of antibodies reversed the course of the disease in both treated animals enabling them to rapidly recover with normal or near-normal lung histology. These data support the clinical application of the humanized antibodies of the invention as a means to diminish morbidity, long-term sequelae, and mortality in children with *pertussis.*

Example 8

Prophylactic Administration of Humanized Antibodies to Newborns

The humanized hu1B7 and hu11E6 antibodies are administered via intramuscular injection to newborns to provide prophylactic treatment against *pertussis* via passive immunization. Since *pertussis* during the first four months of life portends the highest risk for death or serious illness with long-term sequelae, treatment at birth can protect children during this high risk period and/or until they are old enough to receive a standard *pertussis* vaccine. This may be particularly important in the developing world where the risk of contracting *pertussis* is high, the disease kills 160,000 to 300,000 children annually, and newborns only see a physician once at birth.

A cocktail of humanized hu1B7 and hu11E6 antibodies (aka SYN-005) is expected to provide at least four months of prophylaxis due to its plasma half-life and potency.

The half-life of SYN-005 is estimated based on pharmacokinetic (PK) data obtained from baboon studies in conjunction with data available for other antibodies administered as prophylactic treatments to newborns. Specifically, SYN-005 was shown to have a beta half-life in baboons of 11 days.

The potency of SYN-005 was assessed vis-á-vis the World Health Organization's (WHO's) polyclonal serum standard routinely used to predict vaccine efficacy. The WHO potency is quantified in equivalent units (EU), and 5 EU/ml is considered a protective level in humans. See Storsaeter J. et al. (1998), Vaccine, 16(20):1907-16. Specifically, the potency of SYN-005 was determined to be 2 EU/ug. Moreover, in a CHO cell functional assay, an EU of SYN-005 was shown to be approximately seven-fold more potent than an EU of the WHO polyclonal standard. Particularly, the two humanized antibodies in SYN-005 were capable of neutralizing *pertussis* toxin, whereas many of the PTx-binding antibodies in a polyclonal setting did not interfere with *pertussis* toxin function.

Accordingly, the protective plasma level of the SYN-005 cocktail is expected to be greater than 5 EU/ml. Specifically, it is expected that a 40 mg/kg intramuscular dose of SYN-005 will provide a serum level of 100-130 ug/ml at one month and 5 ug/ml at four months. Since SYN-005 has a potency of 2 EU/ug, a serum level of 5 ug/ml is equivalent to 10 EU/ml, twice the level required by the WHO standard for prophylactic treatments. Further, the observation that one EU of SYN-005 is seven-fold more potent than one EU of the WHO polyclonal standard provides an additional margin to ensure ongoing prophylaxis at four months.

Altogether, these data suggest that a single dose of SYN-005 will maintain plasma levels above the threshold required to protect newborns from *pertussis* for at least four months.

INCORPORATION BY REFERENCE

The entire disclosure of each of the patent documents and scientific articles referred to herein is incorporated by reference for all purposes.

The publications discussed herein are provided solely for their disclosure prior to the filing date of the present application. Nothing herein is to be construed as an admission that the present invention is not entitled to antedate such publication by virtue of prior invention.

As used herein, all headings are simply for organization and are not intended to limit the disclosure in any manner. The content of any individual section may be equally applicable to all sections

EQUIVALENTS

The invention may be embodied in other specific forms without departing from the spirit or essential characteristics thereof. The foregoing embodiments are therefore to be considered in all respects illustrative rather than limiting on the invention described herein.

EMBODIMENTS

Embodiments

Embodiment 1. A humanized 1B7 antibody that binds a *pertussis* toxin protein, comprising an immunoglobulin heavy chain variable region and an immunoglobulin light chain variable region, wherein the immunoglobulin heavy chain variable region comprises an amino acid sequence selected from SEQ ID NO:1, SEQ ID NO:2, SEQ ID NO:3, SEQ ID NO:4, SEQ ID NO:5, and SEQ ID NO:6; and the immunoglobulin light chain variable region comprises an amino acid sequence selected from SEQ ID NO:7, SEQ ID NO:8, SEQ ID NO:9, SEQ ID NO:10, SEQ ID NO:11, and SEQ ID NO:12.

Embodiment 2. A humanized 1B7 antibody that binds a *pertussis* toxin protein, comprising an immunoglobulin heavy chain variable region and an immunoglobulin light chain variable region selected from: (a) an immunoglobulin heavy chain variable region comprising the amino acid sequence of SEQ ID NO: 2, and an immunoglobulin light chain variable region comprising the amino acid sequence of SEQ ID NO:8; (b) an immunoglobulin heavy chain variable region comprising the amino acid sequence of SEQ ID NO: 3, and an immunoglobulin light chain variable region comprising the amino acid sequence of SEQ ID NO:9; (c) an immunoglobulin heavy chain variable region comprising the amino acid sequence of SEQ ID NO: 4, and an immunoglobulin light chain variable region comprising the amino acid sequence of SEQ ID NO:10;(d) an immunoglobulin heavy chain variable region comprising the amino acid sequence of SEQ ID NO: 5, and an immunoglobulin light chain variable region comprising the amino acid sequence of SEQ ID NO:11; and (e) an immunoglobulin heavy chain variable region comprising the amino acid sequence of SEQ ID NO: 6, and an immunoglobulin light chain variable region comprising the amino acid sequence of SEQ ID NO:12.

Embodiment 3. A humanized 11E6 antibody that binds a *pertussis* toxin protein, comprising an immunoglobulin heavy chain variable region and an immunoglobulin light chain variable region, wherein the immunoglobulin heavy chain variable region comprises an amino acid sequence selected from SEQ ID NO:13, SEQ ID NO:14, SEQ ID NO:15, SEQ ID NO:16, SEQ ID NO:17, and SEQ ID NO:18; and the immunoglobulin light chain variable region comprises an amino acid sequence selected from SEQ ID NO:19, SEQ ID NO:20, SEQ ID NO:21, SEQ ID NO:22, SEQ ID NO:23, and SEQ ID NO:24.

Embodiment 4. A humanized 11E6 antibody that binds a *pertussis* toxin protein, comprising an immunoglobulin heavy chain variable region and an immunoglobulin light chain variable region selected from: (a) an immunoglobulin heavy chain variable region comprising the amino acid sequence of SEQ ID NO: 14, and an immunoglobulin light chain variable region comprising the amino acid sequence of SEQ ID NO:20; (b) an immunoglobulin heavy chain variable region comprising the amino acid sequence of SEQ ID NO: 15, and an immunoglobulin light chain variable region comprising the amino acid sequence of SEQ ID NO:21; (c) an immunoglobulin heavy chain variable region comprising the amino acid sequence of SEQ ID NO: 16, and an immunoglobulin light chain variable region comprising the amino acid sequence of SEQ ID NO:22; (d) an immunoglobulin heavy chain variable region comprising the amino acid sequence of SEQ ID NO:17, and an immunoglobulin light chain variable region comprising the amino acid sequence of SEQ ID NO:23; and (e) an immunoglobulin heavy chain variable region comprising the amino acid sequence of SEQ ID NO:18, and an immunoglobulin light chain variable region comprising the amino acid sequence of SEQ ID NO:24.

Embodiment 5. The antibody of embodiment 1 or 2, wherein the antibody binds the *pertussis* toxin protein with a $K_D$ of 3 nM or lower.

Embodiment 6. The antibody of embodiment 3 or 4, wherein the antibody binds the *pertussis* toxin protein with a $K_D$ of 12 nM or lower.

Embodiment 7. A humanized 1B7 antibody that binds a *pertussis* toxin protein, wherein the antibody binds the *pertussis* toxin protein with a $K_D$ of 3 nM or lower.

Embodiment 8. The antibody of embodiment 7, wherein the $K_D$ is about 3 nM, or about 2 nM, or about 1 nM, or about 0.5 nM.

Embodiment 9. A humanized 11E6 antibody that binds a *pertussis* toxin protein, wherein the antibody binds the *pertussis* toxin protein with a $K_D$ of 12 nM or lower.

Embodiment 10. The antibody of embodiment 9, wherein the $K_D$ is about 12 nM, or about 10 nM, or about 8 nM, or about 6 nM, or 4 nM, or 2 nM, or about 1 nM, or about 0.5 nM.

Embodiment 11. An isolated nucleic acid comprising a nucleotide sequence encoding an immunoglobulin heavy chain variable region of any one of embodiments 1-10.

Embodiment 12. An isolated nucleic acid comprising a nucleotide sequence encoding an immunoglobulin light chain variable region of any one of embodiments 1-10.

Embodiment 13. An expression vector containing the nucleic acid of embodiment 11.

Embodiment 14. An expression vector containing the nucleic acid of embodiment 12.

Embodiment 15. The expression vector of embodiment 14, further comprising the nucleic acid of embodiment 11.

Embodiment 16. A host cell comprising the expression vector of embodiment 13.

Embodiment 17. A host cell comprising the expression vector of embodiment 14.

Embodiment 18. A host cell comprising the expression vector of embodiment 15.

Embodiment 19. The host cell of embodiment 17, further comprising the expression vector of embodiment 13.

Embodiment 20. A method of producing a polypeptide comprising an immunoglobulin heavy chain variable region or an immunoglobulin light chain variable region, the method comprising: (a) growing the host cell of embodiment 16 or 17 under conditions so that the host cell express the polypeptide comprising the immunoglobulin heavy chain variable region or the immunoglobulin light chain variable region; and (b) purifying the polypeptide comprising the immunoglobulin heavy chain variable region or the immunoglobulin light chain variable region.

Embodiment 21. A method of producing an antibody that binds a *pertussis* toxin protein, the method comprising: (a) growing the host cell of embodiment 18 or 19 under conditions so that the host cell expresses a polypeptide comprising the immunoglobulin heavy chain variable region and/or the immunoglobulin light chain variable region, thereby producing the antibody; and (b) purifying the antibody.

Embodiment 22. A pharmaceutical composition comprising one or more antibodies of any one of embodiments 1-10, and a pharmaceutically acceptable excipient.

Embodiment 23. The pharmaceutical composition of embodiment 22, comprising the humanized 1B7 antibody of any one of embodiment 1, 2, 5, 7, or 8 and the humanized 11E6 antibody of any one of embodiment 3, 4, 6, 9 or 10.

Embodiment 24. The pharmaceutical composition of embodiment 23, wherein the composition is formulated as a colloidal dispersion system, macromolecular complex, nanocapsule, microsphere, bead, oil-in-water emulsion, micelle, mixed micelle, or liposome.

Embodiment 25. The pharmaceutical composition of any one of embodiments 22-24, wherein the composition is formulated for oral, intranasal, pulmonary, intradermal, transdermal, subcutaneous, intramuscular, intraperitoneal, or intravenous delivery.

Embodiment 26. A method of treating a patient infected with *Bordetella pertussis,* comprising administering to the patient the antibody of any of embodiments 1-10 or the pharmaceutical composition of any one of embodiments 22-25.

Embodiment 27. A method of treating a patient infected with *Bordetella pertussis,* comprising co-administering to the patient an effective amount of the humanized 1B7 antibody of any one of embodiments 1, 2, 5, 7, or 8 and an effective amount of the humanized 11E6 antibody of any one of embodiment 3, 4, 6, 9 or 10.

Embodiment 28. The method of embodiment 27, wherein the humanized 1B7 antibody and the humanized 11E6 antibody are administered simultaneously to the patient.

Embodiment 29. The method of embodiment 27, wherein the humanized 1B7 antibody is administered to the patient prior to administering the humanized 11 E6 antibody to the patient.

Embodiment 30. The method of embodiment 27, wherein the humanized 1B7 antibody is administered to the patient after administering the humanized 11E6 antibody to the patient.

Embodiment 31. The method of embodiment 27, wherein co-administration of the humanized 1B7 antibody and the humanized 11E6 antibody produces synergistic effects.

Embodiment 32. A method of treating a patient infected with *Bordetella pertussis,* comprising co-administering to the patient at least one antibody of any one of embodiments 1-10 or the pharmaceutical composition of any one of embodiments 22-25, and an antimicrobial agent.

Embodiment 33. The method of embodiment 33, wherein the antimicrobial agent is selected from azithromycin, clarithromycin, erythromycin, trimethoprim-sulfamethoxasole, roxithromycin, ketolides, ampicillin, amoxicillin, tetracycline, chloramphenicol, fluoroquinolones, and cephalosporins.

Embodiment 34. The method of any one of embodiments 26-33, wherein the patient is human.

Embodiment 35. The method of embodiment 34, wherein the human is an infant.

Embodiment 36. A method of preventing *Bordetella pertussis* infection in a subject previously exposed to *Bordetella pertussis,* comprising administering to the subject an effective amount of the antibody of any of embodiments 1-10 or an effective amount of the pharmaceutical composition of any one of embodiments 22-25.

Embodiment 37. The method of any one of embodiments 26-36, wherein the method comprises a reduction of white blood cell count.

Embodiment 38. The method of any one of embodiments 26-37, wherein the method comprises a reduction of the duration and/or the frequency of cough.

Embodiment 39. The method of any one of embodiments 26-38, wherein the method comprises a reduction of *Bordetella pertussis* level in the nasopharynx and/or the lung.

Embodiment 40. The method of any one of embodiments 26-39, wherein the *pertussis* toxin protein is neutralized.

Embodiment 41. The method of embodiment 40, wherein the *pertussis* toxin protein is prevented from binding to its cellular receptor.

Embodiment 42. The method of embodiment 40, wherein the *pertussis* toxin protein is prevented from reaching the cellular cytosol.

Embodiment 43. A method of treating a patient infected with *Bordetella parapertussis,* comprising administering to the patient an effective amount of the antibody of any of embodiments 1-10 or an effective amount of the pharmaceutical composition of any one of embodiments 22-25.

Embodiment 44. A method of treating a patient infected with *Bordetella parapertussis,* comprising co-administering to the patient an effective amount of the humanized 1B7 antibody of any one of embodiments 1, 2, 5, 7, or 8 and an effective amount of the humanized 11E6 antibody of any one of embodiment 3, 4, 6, 9 or 10.

Embodiment 45. A method of preventing *Bordetella parapertussis* infection in a subject previously exposed to *Bordetella pertussis*, comprising administering to the subject an effective amount of the antibody of any of embodiments 1-10 or the pharmaceutical composition of any one of embodiments 22-25.

P1 Embodiments:

Embodiment 1. A humanized 1B7 antibody that binds a *pertussis* toxin protein, comprising an immunoglobulin heavy chain variable region and an immunoglobulin light chain variable region, wherein the immunoglobulin heavy chain variable region comprises an amino acid sequence selected from SEQ ID NO:1, SEQ ID NO:2, SEQ ID NO:3, SEQ ID NO:4, SEQ ID NO:5, and SEQ ID NO:6; and the immunoglobulin light chain variable region comprises an amino acid sequence selected from SEQ ID NO:7, SEQ ID NO:8, SEQ ID NO:9, SEQ ID NO:10, SEQ ID NO:11, and SEQ ID NO:12.

Embodiment 2. A humanized 1B7 antibody that binds a *pertussis* toxin protein, comprising an immunoglobulin heavy chain variable region and an immunoglobulin light chain variable region selected from: (a) an immunoglobulin heavy chain variable region comprising the amino acid sequence of SEQ ID NO: 2, and an immunoglobulin light chain variable region comprising the amino acid sequence of SEQ ID NO:8; (b) an immunoglobulin heavy chain variable region comprising the amino acid sequence of SEQ ID NO: 3, and an immunoglobulin light chain variable region comprising the amino acid sequence of SEQ ID NO:9; (c) an immunoglobulin heavy chain variable region comprising the amino acid sequence of SEQ ID NO: 4, and an immunoglobulin light chain variable region comprising the amino acid sequence of SEQ ID NO:10; (d) an immunoglobulin heavy chain variable region comprising the amino acid sequence of SEQ ID NO: 5, and an immunoglobulin light chain variable region comprising the amino acid sequence of SEQ ID NO:11; and (e) an immunoglobulin heavy chain variable region comprising the amino acid sequence of SEQ ID NO: 6, and an immunoglobulin light chain variable region comprising the amino acid sequence of SEQ ID NO:12.

Embodiment 3. A humanized 11E6 antibody that binds a *pertussis* toxin protein, comprising an immunoglobulin heavy chain variable region and an immunoglobulin light chain variable region, wherein the immunoglobulin heavy chain variable region comprises an amino acid sequence selected from SEQ ID NO:13, SEQ ID NO:14, SEQ ID NO:15, SEQ ID NO:16, SEQ ID NO:17, and SEQ ID NO:18; and the immunoglobulin light chain variable region comprises an amino acid sequence selected from SEQ ID NO:19, SEQ ID NO:20, SEQ ID NO:21, SEQ ID NO:22, SEQ ID NO:23, and SEQ ID NO:24.

Embodiment 4. A humanized 11E6 antibody that binds a *pertussis* toxin protein, comprising an immunoglobulin heavy chain variable region and an immunoglobulin light chain variable region selected from: (a) an immunoglobulin heavy chain variable region comprising the amino acid sequence of SEQ ID NO: 14, and an immunoglobulin light chain variable region comprising the amino acid sequence of SEQ ID NO:20; (b) an immunoglobulin heavy chain variable region comprising the amino acid sequence of SEQ ID NO: 15, and an immunoglobulin light chain variable region comprising the amino acid sequence of SEQ ID NO:21; (c) an immunoglobulin heavy chain variable region comprising the amino acid sequence of SEQ ID NO: 16, and an immunoglobulin light chain variable region comprising the amino acid sequence of SEQ ID NO:22; (d) an immunoglobulin heavy chain variable region comprising the amino acid sequence of SEQ ID NO:17, and an immunoglobulin light chain variable region comprising the amino acid sequence of SEQ ID NO:23; and (e) an immunoglobulin heavy chain variable region comprising the amino acid sequence of SEQ ID NO:18, and an immunoglobulin light chain variable region comprising the amino acid sequence of SEQ ID NO:24.

Embodiment 5. The antibody of embodiment 1 or 2, wherein the antibody binds the *pertussis* toxin protein with a $K_D$ of 3 nM or lower.

Embodiment 6. The antibody of embodiment 3 or 4, wherein the antibody binds the *pertussis* toxin protein with a $K_D$ of 12 nM or lower.

Embodiment 7. A humanized 1B7 antibody that binds a *pertussis* toxin protein, wherein the antibody binds the *pertussis* toxin protein with a $K_D$ of 3 nM or lower.

Embodiment 8. The antibody of embodiment 6, wherein the $K_D$ is about 3 nM, or about 2 nM, or about 1 nM, or about 0.5 nM.

Embodiment 9. A humanized 11E6 antibody that binds a *pertussis* toxin protein, wherein the antibody binds the *pertussis* toxin protein with a $K_D$ of 12 nM or lower.

Embodiment 10. The antibody of embodiment 9, wherein the $K_D$ is about 12 nM, or about 10 nM, or about 8 nM, or about 6 nM, or 4 nM, or 2 nM, or about 1 nM, or about 0.5 nM.

Embodiment 11. An isolated nucleic acid comprising a nucleotide sequence encoding an immunoglobulin heavy chain variable region of any one of embodiments 1-10.

Embodiment 12. An isolated nucleic acid comprising a nucleotide sequence encoding an immunoglobulin light chain variable region of any one of embodiments 1-10.

Embodiment 13. An expression vector containing the nucleic acid of embodiment 11.

Embodiment 14. An expression vector containing the nucleic acid of embodiment 12.

Embodiment 15. The expression vector of embodiment 14, further comprising the nucleic acid of embodiment 11.

Embodiment 16. A host cell comprising the expression vector of embodiment 13.

Embodiment 17. A host cell comprising the expression vector of embodiment 14.

Embodiment 18. A host cell comprising the expression vector of embodiment 15.

Embodiment 19. The host cell of embodiment 17, further comprising the expression vector of embodiment 13.

Embodiment 20. A method of producing a polypeptide comprising an immunoglobulin heavy chain variable region or an immunoglobulin light chain variable region, the method comprising: (a) growing the host cell of embodiment 16 or 17 under conditions so that the host cell express the polypeptide comprising the immunoglobulin heavy chain variable region or the immunoglobulin light chain variable region; and (b) purifying the polypeptide comprising the immunoglobulin heavy chain variable region or the immunoglobulin light chain variable region.

Embodiment 21. A method of producing an antibody that binds a *pertussis* toxin protein, the method comprising: (a) growing the host cell of embodiment 18 or 19 under conditions so that the host cell expresses a polypeptide comprising the immunoglobulin heavy chain variable region and/or the immunoglobulin light chain variable region, thereby producing the antibody; and (b) purifying the antibody.

Embodiment 22. A pharmaceutical composition comprising the antibody of any one of embodiments 1-10, and a pharmaceutically acceptable excipient.

Embodiment 23. The pharmaceutical composition of embodiment 22, comprising the humanized 1B7 antibody of any one of embodiment 1, 2, 5, 7, or 8 and the humanized 11E6 antibody of any one of embodiment 3, 4, 6, 9 or 10.

Embodiment 24. The pharmaceutical composition of embodiment 23, wherein the composition is formulated as a colloidal dispersion system, macromolecular complex, nanocapsule, microsphere, bead, oil-in-water emulsion, micelle, mixed micelle, or liposome.

Embodiment 25. The pharmaceutical composition of any one of embodiments 22-24, wherein the composition is formulated for oral, intranasal, pulmonary, intradermal, transdermal, subcutaneous, intramuscular, intraperitoneal, or intravenous delivery.

Embodiment 26. A method of treating a patient infected with *Bordetella pertussis*, comprising administering to the patient the antibody of any of embodiments 1-10 or the pharmaceutical composition of any one of embodiments 22-25.

Embodiment 27. A method of treating a patient infected with *Bordetella pertussis*, comprising co-administering to the patient the humanized 1B7 antibody of any one of embodiments 1, 2, 5, 7, or 8 and the humanized 11E6 antibody of any one of embodiment 3, 4, 6, 9 or 10.

Embodiment 28. The method of embodiment 27, wherein the humanized 1B7 antibody and the humanized 11E6 antibody are administered simultaneous to the patient.

Embodiment 29. The method of embodiment 27, wherein the humanized 1B7 antibody is administered to the patient prior to administering the humanized 11 E6 antibody to the patient.

Embodiment 30. The method of embodiment 27, wherein the humanized 1B7 antibody is administered to the patient after administering the humanized 11E6 antibody to the patient.

Embodiment 31. The method of embodiment 27, wherein co-administration of the humanized 1B7 antibody and the humanized 11E6 antibody produces synergistic effects.

Embodiment 32. A method of treating a patient infected with *Bordetella pertussis*, comprising co-administering to the patient at least one antibody of any one of embodiments 1-10 or the pharmaceutical composition of any one of embodiments 22-25, and an antimicrobial agent.

Embodiment 33. The method of embodiment 33, wherein the antimicrobial agent is selected from azithromycin, clarithromycin, erythromycin, trimethoprim-sulfamethoxasole, roxithromycin, ketolides, ampicillin, amoxicillin, tetracycline, chloramphenicol, fluoroquinolones, and cephalosporins.

Embodiment 34. The method of any one of embodiments 26-33, wherein the patient is human.

Embodiment 35. The method of embodiment 34, wherein the human is an infant.

Embodiment 36. A method of preventing *Bordetella pertussis* infection in a subject previously exposed to *Bordetella pertussis*, comprising administering to the subject the antibody of any of embodiments 1-10 or the pharmaceutical composition of any one of embodiments 22-25.

Embodiment 37. The method of any one of embodiments 26-36, wherein the method comprises a reduction of white blood cell count.

Embodiment 38. The method of any one of embodiments 26-37, wherein the method comprises a reduction of the duration and/or the frequency of cough.

Embodiment 39. The method of any one of embodiments 26-38, wherein the method comprises a reduction of *Bordetella pertussis* level in the nasopharynx and/or the lung.

Embodiment 40. The method of any one of embodiments 26-39, wherein the *pertussis* toxin protein is neutralized.

Embodiment 41. The method of embodiment 40, wherein the *pertussis* toxin protein is prevented from binding to its cellular receptor.

Embodiment 42. The method of embodiment 40, wherein the *pertussis* toxin protein is prevented from reaching the cellular cytosol.

Embodiment 43. A method of treating a patient infected with *Bordetella parapertussis*, comprising administering to the patient the antibody of any of embodiments 1-10 or the pharmaceutical composition of any one of embodiments 22-25.

Embodiment 44. A method of treating a patient infected with *Bordetella parapertussis*, comprising co-administering to the patient the humanized 1B7 antibody of any one of embodiments 1, 2, 5, 7, or 8 and the humanized 11E6 antibody of any one of embodiment 3, 4, 6, 9 or 10.

Embodiment 45. A method of preventing *Bordetella parapertussis* infection in a subject previously exposed to *Bordetella pertussis*, comprising administering to the subject the antibody of any of embodiments 1-10 or the pharmaceutical composition of any one of embodiments 22-25.

Embodiment 46. A composition as disclosed herein.

Embodiment 47. The use of any composition described herein one or more of: treatment of *pertussis* and manufacture of a medicament for the treatment of *pertussis*.

What is claimed is:

1. A humanized 1B7 antibody that binds a *pertussis* toxin protein, comprising an immunoglobulin heavy chain variable region and an immunoglobulin light chain variable region, wherein the immunoglobulin heavy chain variable region comprises the amino acid sequence of SEQ ID NO1, SEQ ID NO:2, SEQ ID NO:3, SEQ ID NO:4, SEQ ID NO:5, or SEQ ID NO:6; and the immunoglobulin light chain variable region comprises the amino acid sequence of SEQ ID NO:7, SEQ ID NO:8, SEQ ID NO:9, SEQ ID NO:10, SEQ ID NO:11, or SEQ ID NO:12.

2. The humanized 1B7 antibody of claim 1, wherein the immunoglobulin heavy chain variable region comprises the amino acid sequence of SEQ ID NO:3 and the immunoglobulin light chain variable region comprises the amino acid sequence of SEQ ID NO:11.

3. The humanized 1B7 antibody of claim 1, wherein the antibody binds the *pertussis* toxin protein with a $K_D$ of 3 nM or lower.

4. A pharmaceutical composition comprising the humanized 1B7 antibody of claim 1 and a pharmaceutically acceptable excipient.

5. A method of treating a patient infected with *Bordetella pertussis* comprising administering to the patient an effective amount of the humanized 1 B7 antibody of claim 1.

* * * * *

SEQUENCE LISTING

<160> NUMBER OF SEQ ID NOS: 24

<210> SEQ ID NO 1
<211> LENGTH: 118
<212> TYPE: PRT
<213> ORGANISM: Artificial sequence
<220> FEATURE:
<223> OTHER INFORMATION: Synthetic polypeptide

<400> SEQUENCE: 1

Gln Val Gln Leu Gln Gln Pro Gly Ser Glu Leu Val Arg Pro Gly Ala
1               5                   10                  15

Ser Val Lys Leu Ser Cys Lys Ala Ser Gly Tyr Lys Phe Thr Ser Tyr
                20                  25                  30

Trp Met His Trp Val Lys Gln Arg Pro Gly Gln Gly Leu Glu Trp Ile
            35                  40                  45

Gly Asn Ile Phe Pro Gly Ser Gly Ser Thr Asn Tyr Asp Glu Lys Phe
    50                  55                  60

Asn Ser Lys Ala Thr Leu Thr Val Asp Thr Ser Ser Asn Thr Ala Tyr
65                  70                  75                  80

Met Gln Leu Ser Ser Leu Thr Ser Glu Asp Ser Ala Val Tyr Tyr Cys
                85                  90                  95

Thr Arg Trp Leu Ser Gly Ala Tyr Phe Asp Tyr Trp Gly Gln Gly Thr
                100                 105                 110

Thr Leu Thr Val Ser Ser
            115

<210> SEQ ID NO 2
<211> LENGTH: 118
<212> TYPE: PRT
<213> ORGANISM: Artificial sequence
<220> FEATURE:
<223> OTHER INFORMATION: Synthetic polypeptide

<400> SEQUENCE: 2

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Lys Phe Thr Ser Tyr
                20                  25                  30

Trp Met His Trp Val Arg Gln Ala Pro Gly Gln Gly Leu Glu Trp Ile
            35                  40                  45

Gly Asn Ile Phe Pro Gly Ser Gly Ser Thr Asn Tyr Asp Glu Lys Phe
    50                  55                  60

Asn Ser Arg Val Thr Leu Thr Val Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Trp Leu Ser Gly Ala Tyr Phe Asp Tyr Trp Gly Gln Gly Thr
                100                 105                 110

Thr Val Thr Val Ser Ser
            115

<210> SEQ ID NO 3
<211> LENGTH: 118
<212> TYPE: PRT
<213> ORGANISM: Artificial sequence
<220> FEATURE:
<223> OTHER INFORMATION: Synthetic polypeptide

<400> SEQUENCE: 3

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Lys Phe Thr Ser Tyr
                20                  25                  30

Trp Met His Trp Val Arg Gln Ala Pro Gly Gln Gly Leu Glu Trp Ile
            35                  40                  45

Gly Asn Ile Phe Pro Gly Ser Gly Ser Thr Asn Tyr Ala Gln Lys Phe
        50                  55                  60

Gln Gly Arg Val Thr Leu Thr Val Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Trp Leu Ser Gly Ala Tyr Phe Asp Tyr Trp Gly Gln Gly Thr
            100                 105                 110

Thr Val Thr Val Ser Ser
            115
```

```
<210> SEQ ID NO 4
<211> LENGTH: 118
<212> TYPE: PRT
<213> ORGANISM: Artificial sequence
<220> FEATURE:
<223> OTHER INFORMATION: Synthetic polypeptide

<400> SEQUENCE: 4

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Lys Phe Thr Ser Tyr
                20                  25                  30

Trp Met His Trp Val Arg Gln Ala Pro Gly Gln Gly Leu Glu Trp Ile
            35                  40                  45

Gly Asn Ile Phe Pro Gly Ser Gly Ser Thr Asn Tyr Ala Gln Lys Phe
        50                  55                  60

Gln Gly Arg Val Thr Leu Thr Val Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Trp Leu Ser Gly Ala Tyr Phe Asp Tyr Trp Gly Gln Gly Thr
            100                 105                 110

Thr Val Thr Val Ser Ser
            115
```

```
<210> SEQ ID NO 5
<211> LENGTH: 118
<212> TYPE: PRT
<213> ORGANISM: Artificial sequence
<220> FEATURE:
<223> OTHER INFORMATION: Synthetic polypeptide

<400> SEQUENCE: 5

Gln Val Gln Leu Gln Gln Ser Gly Ser Glu Leu Lys Lys Pro Gly Ala
1               5                   10                  15

Ser Val Lys Ile Ser Cys Lys Ala Ser Gly Tyr Lys Phe Thr Ser Tyr
                20                  25                  30

Trp Met His Trp Val Lys Gln Arg Pro Gly Gln Gly Leu Glu Trp Ile
            35                  40                  45

Gly Asn Ile Phe Pro Gly Ser Gly Ser Thr Asn Tyr Asp Glu Lys Phe
```

```
                    50                  55                  60
Asn Ser Arg Val Thr Leu Thr Val Asp Thr Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Thr Arg Trp Leu Ser Gly Ala Tyr Phe Asp Tyr Trp Gly Gln Gly Thr
                100                 105                 110

Thr Leu Thr Val Ser Ser
            115

<210> SEQ ID NO 6
<211> LENGTH: 118
<212> TYPE: PRT
<213> ORGANISM: Artificial sequence
<220> FEATURE:
<223> OTHER INFORMATION: Synthetic polypeptide

<400> SEQUENCE: 6

Gln Val Gln Leu Val Gln Ser Gly Ala Glu Leu Val Lys Pro Gly Ala
  1               5                  10                  15

Ser Val Lys Leu Ser Cys Lys Ala Ser Gly Tyr Lys Phe Thr Ser Tyr
                 20                  25                  30

Trp Met His Val Lys Gln Arg Pro Gly Gln Gly Leu Glu Trp Ile
             35                  40                  45

Gly Asn Ile Phe Pro Gly Ser Gly Ser Thr Asn Tyr Asp Glu Lys Phe
 50                  55                  60

Asn Ser Lys Ala Thr Leu Thr Val Asp Thr Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Thr Arg Trp Leu Ser Gly Ala Tyr Phe Asp Tyr Trp Gly Gln Gly Thr
                100                 105                 110

Thr Leu Thr Val Ser Ser
            115

<210> SEQ ID NO 7
<211> LENGTH: 106
<212> TYPE: PRT
<213> ORGANISM: Artificial sequence
<220> FEATURE:
<223> OTHER INFORMATION: Synthetic polypeptide

<400> SEQUENCE: 7

Gln Ile Val Leu Thr Gln Ser Pro Ala Leu Met Ser Ala Ser Pro Gly
  1               5                  10                  15

Glu Lys Val Thr Met Thr Cys Ser Ala Ser Ser Val Ser Phe Met
                 20                  25                  30

Tyr Trp Tyr Gln Gln Lys Pro Arg Ser Ser Pro Lys Pro Trp Ile Tyr
             35                  40                  45

Leu Thr Ser Asn Leu Pro Ser Gly Val Pro Ala Arg Phe Ser Gly Ser
 50                  55                  60

Gly Ser Gly Thr Ser Tyr Ser Leu Thr Ile Ser Ser Met Glu Ala Glu
 65                  70                  75                  80

Asp Ala Ala Thr Tyr Tyr Cys Gln Gln Trp Ser Ser His Pro Pro Thr
                 85                  90                  95

Phe Gly Ser Gly Thr Lys Leu Glu Ile Lys
                100                 105
```

<210> SEQ ID NO 8
<211> LENGTH: 106
<212> TYPE: PRT
<213> ORGANISM: Artificial sequence
<220> FEATURE:
<223> OTHER INFORMATION: Synthetic polypeptide

<400> SEQUENCE: 8

```
Gln Ile Val Leu Thr Gln Ser Pro Asp Phe Gln Ser Val Thr Pro Lys
1               5                   10                  15
Glu Lys Val Thr Ile Thr Cys Ser Ala Ser Ser Val Ser Phe Met
            20                  25                  30
Tyr Trp Tyr Gln Gln Lys Pro Asp Gln Ser Pro Lys Pro Leu Ile Tyr
            35                  40                  45
Leu Thr Ser Asn Leu Pro Ser Gly Val Pro Ala Arg Phe Ser Gly Ser
        50                  55                  60
Gly Ser Gly Thr Ser Tyr Thr Leu Thr Ile Asn Ser Leu Glu Ala Glu
65                  70                  75                  80
Asp Ala Ala Thr Tyr Tyr Cys Gln Gln Trp Ser Ser His Pro Pro Thr
                85                  90                  95
Phe Gly Ser Gly Thr Lys Val Glu Ile Lys
            100                 105
```

<210> SEQ ID NO 9
<211> LENGTH: 106
<212> TYPE: PRT
<213> ORGANISM: Artificial sequence
<220> FEATURE:
<223> OTHER INFORMATION: Synthetic polypeptide

<400> SEQUENCE: 9

```
Gln Ile Val Leu Thr Gln Ser Pro Asp Phe Gln Ser Val Thr Pro Lys
1               5                   10                  15
Glu Lys Val Thr Ile Thr Cys Arg Ala Ser Ser Val Ser Phe Met
            20                  25                  30
Tyr Trp Tyr Gln Gln Lys Pro Asp Gln Ser Pro Lys Pro Leu Ile Tyr
            35                  40                  45
Leu Thr Ser Asn Leu Pro Ser Gly Val Pro Ala Arg Phe Ser Gly Ser
        50                  55                  60
Gly Ser Gly Thr Asp Tyr Thr Leu Thr Ile Asn Ser Leu Glu Ala Glu
65                  70                  75                  80
Asp Ala Ala Thr Tyr Tyr Cys Gln Gln Trp Ser Ser His Pro Pro Thr
                85                  90                  95
Phe Gly Ser Gly Thr Lys Val Glu Ile Lys
            100                 105
```

<210> SEQ ID NO 10
<211> LENGTH: 106
<212> TYPE: PRT
<213> ORGANISM: Artificial sequence
<220> FEATURE:
<223> OTHER INFORMATION: Synthetic polypeptide

<400> SEQUENCE: 10

```
Gln Ile Val Leu Thr Gln Ser Pro Asp Phe Gln Ser Val Thr Pro Lys
1               5                   10                  15
Glu Lys Val Thr Ile Thr Cys Arg Ala Ser Ser Ile Val Ser Phe Leu
            20                  25                  30
Tyr Trp Tyr Gln Gln Lys Pro Asp Gln Ser Pro Lys Pro Leu Ile Tyr
```

```
                    35                  40                  45
Leu Ala Ser Asn Leu Pro Ser Gly Val Pro Ala Arg Phe Ser Gly Ser
            50                  55                  60
Gly Ser Gly Thr Asp Tyr Thr Leu Thr Ile Asn Ser Leu Glu Ala Glu
 65                  70                  75                  80
Asp Ala Ala Thr Tyr Tyr Cys Gln Gln Trp Ser Ser His Pro Pro Thr
                85                  90                  95
Phe Gly Ser Gly Thr Lys Val Glu Ile Lys
            100                 105

<210> SEQ ID NO 11
<211> LENGTH: 106
<212> TYPE: PRT
<213> ORGANISM: Artificial sequence
<220> FEATURE:
<223> OTHER INFORMATION: Synthetic polypeptide

<400> SEQUENCE: 11

Gln Ile Val Leu Thr Gln Ser Pro Ala Thr Leu Ser Val Ser Pro Gly
 1               5                  10                  15
Glu Arg Val Thr Leu Thr Cys Ser Ala Ser Ser Ser Val Ser Phe Met
                20                  25                  30
Tyr Trp Tyr Gln Gln Lys Pro Gly Arg Ala Pro Lys Pro Leu Ile Tyr
            35                  40                  45
Leu Thr Ser Asn Leu Pro Ser Gly Val Pro Ala Arg Phe Ser Gly Ser
            50                  55                  60
Gly Ser Gly Thr Ser Tyr Thr Leu Thr Ile Asn Ser Leu Glu Ala Glu
 65                  70                  75                  80
Asp Ala Ala Thr Tyr Tyr Cys Gln Gln Trp Ser Ser His Pro Pro Thr
                85                  90                  95
Phe Gly Ser Gly Thr Lys Leu Glu Ile Lys
            100                 105

<210> SEQ ID NO 12
<211> LENGTH: 106
<212> TYPE: PRT
<213> ORGANISM: Artificial sequence
<220> FEATURE:
<223> OTHER INFORMATION: Synthetic polypeptide

<400> SEQUENCE: 12

Gln Ile Val Leu Thr Gln Ser Pro Asp Phe Met Ser Ala Thr Pro Gly
 1               5                  10                  15
Glu Lys Val Thr Met Thr Cys Ser Ala Ser Ser Ser Val Ser Phe Met
                20                  25                  30
Tyr Trp Tyr Gln Gln Lys Pro Arg Gln Ser Pro Lys Pro Trp Ile Tyr
            35                  40                  45
Leu Thr Ser Asn Leu Pro Ser Gly Val Pro Ala Arg Phe Ser Gly Ser
            50                  55                  60
Gly Ser Gly Thr Asp Tyr Thr Leu Thr Ile Asn Ser Met Glu Ala Glu
 65                  70                  75                  80
Asp Ala Ala Thr Tyr Tyr Cys Gln Gln Trp Ser Ser His Pro Pro Thr
                85                  90                  95
Phe Gly Ser Gly Thr Lys Leu Glu Ile Lys
            100                 105

<210> SEQ ID NO 13
<211> LENGTH: 123
```

```
<212> TYPE: PRT
<213> ORGANISM: Artificial sequence
<220> FEATURE:
<223> OTHER INFORMATION: Synthetic polypeptide

<400> SEQUENCE: 13

Glu Val Lys Val Val Glu Ser Gly Gly Gly Leu Val Gln Pro Gly Gly
1               5                   10                  15

Ser Leu Arg Leu Ser Cys Thr Thr Ser Gly Phe Thr Phe Thr Asp Tyr
            20                  25                  30

Tyr Val Ser Trp Val Arg Gln Pro Pro Gly Lys Ala Leu Glu Trp Leu
        35                  40                  45

Gly Phe Ile Arg Asn Lys Val Asn Gly Tyr Thr Thr Glu Phe Ser Ser
    50                  55                  60

Ser Val Lys Gly Arg Phe Thr Ile Ser Arg Asp Asn Ser Gln Ser Ile
65                  70                  75                  80

Leu Tyr Leu Gln Met Asn Thr Leu Arg Val Glu Asp Ser Ala Thr Tyr
                85                  90                  95

Tyr Cys Ala Arg Val Ser Tyr Tyr Gly Arg Gly Trp Tyr Phe Asp Tyr
            100                 105                 110

Trp Gly Gln Gly Thr Thr Leu Thr Val Ser Ser
        115                 120

<210> SEQ ID NO 14
<211> LENGTH: 123
<212> TYPE: PRT
<213> ORGANISM: Artificial sequence
<220> FEATURE:
<223> OTHER INFORMATION: Synthetic polypeptide

<400> SEQUENCE: 14

Glu Val Gln Val Val Glu Ser Gly Gly Gly Leu Val Gln Pro Gly Arg
1               5                   10                  15

Ser Leu Arg Leu Ser Cys Thr Thr Ser Gly Phe Thr Phe Thr Asp Tyr
            20                  25                  30

Tyr Val Ser Trp Val Arg Gln Ala Pro Gly Lys Ala Leu Glu Trp Leu
        35                  40                  45

Gly Phe Ile Arg Asn Lys Val Asn Gly Tyr Thr Thr Glu Phe Ser Ser
    50                  55                  60

Ser Val Lys Gly Arg Phe Thr Ile Ser Arg Asp Asn Ser Lys Ser Ile
65                  70                  75                  80

Leu Tyr Leu Gln Met Asn Ser Leu Lys Ile Glu Asp Thr Ala Val Tyr
                85                  90                  95

Tyr Cys Ala Arg Val Ser Tyr Tyr Gly Arg Gly Trp Tyr Phe Asp Tyr
            100                 105                 110

Trp Gly Gln Gly Thr Thr Val Thr Val Ser Ser
        115                 120

<210> SEQ ID NO 15
<211> LENGTH: 123
<212> TYPE: PRT
<213> ORGANISM: Artificial sequence
<220> FEATURE:
<223> OTHER INFORMATION: Synthetic polypeptide

<400> SEQUENCE: 15

Glu Val Gln Val Val Glu Ser Gly Gly Gly Leu Val Gln Pro Gly Arg
1               5                   10                  15

Ser Leu Arg Leu Ser Cys Thr Thr Ser Gly Phe Thr Phe Thr Asp Tyr
```

```
            20                  25                  30
Tyr Val Ser Trp Val Arg Gln Ala Pro Gly Lys Ala Leu Glu Trp Val
        35                  40                  45

Gly Phe Ile Arg Asn Lys Val Asn Gly Tyr Thr Thr Glu Phe Ala Ala
    50                  55                  60

Ser Val Arg Gly Arg Phe Thr Ile Ser Arg Asp Asn Ser Lys Ser Ile
65                  70                  75                  80

Leu Tyr Leu Gln Met Asn Ser Leu Lys Ile Glu Asp Thr Ala Val Tyr
                85                  90                  95

Tyr Cys Ala Arg Val Ser Tyr Tyr Gly Arg Gly Trp Tyr Phe Asp Tyr
            100                 105                 110

Trp Gly Gln Gly Thr Thr Val Thr Val Ser Ser
            115                 120
```

<210> SEQ ID NO 16
<211> LENGTH: 123
<212> TYPE: PRT
<213> ORGANISM: Artificial sequence
<220> FEATURE:
<223> OTHER INFORMATION: Synthetic polypeptide

<400> SEQUENCE: 16

```
Glu Val Gln Val Val Glu Ser Gly Gly Gly Leu Val Gln Pro Gly Arg
1               5                   10                  15

Ser Leu Arg Leu Ser Cys Thr Thr Ser Gly Phe Thr Phe Thr Asp Tyr
            20                  25                  30

Tyr Val Ser Trp Val Arg Gln Ala Pro Gly Lys Ala Leu Glu Trp Val
        35                  40                  45

Gly Phe Ile Arg Asn Lys Val Asn Gly Tyr Thr Thr Glu Phe Ala Ala
    50                  55                  60

Ser Val Arg Gly Arg Phe Thr Ile Ser Arg Asp Asn Ser Lys Ser Ile
65                  70                  75                  80

Leu Tyr Leu Gln Met Asn Ser Leu Lys Ile Glu Asp Thr Ala Val Tyr
                85                  90                  95

Tyr Cys Ala Arg Val Ser Tyr Tyr Gly Arg Gly Trp Tyr Phe Asp Tyr
            100                 105                 110

Trp Gly Gln Gly Thr Thr Val Thr Val Ser Ser
            115                 120
```

<210> SEQ ID NO 17
<211> LENGTH: 123
<212> TYPE: PRT
<213> ORGANISM: Artificial sequence
<220> FEATURE:
<223> OTHER INFORMATION: Synthetic polypeptide

<400> SEQUENCE: 17

```
Glu Val Gln Val Val Glu Ser Gly Gly Gly Leu Val Gln Pro Gly Gly
1               5                   10                  15

Ser Leu Arg Leu Ser Cys Thr Thr Ser Gly Phe Thr Phe Thr Asp Tyr
            20                  25                  30

Tyr Val Ser Trp Val Arg Gln Pro Pro Gly Lys Ala Leu Glu Trp Leu
        35                  40                  45

Gly Phe Ile Arg Asn Lys Val Asn Gly Tyr Thr Thr Glu Phe Ser Ser
    50                  55                  60

Ser Val Lys Gly Arg Phe Thr Ile Ser Arg Asp Asn Ser Lys Ser Thr
65                  70                  75                  80
```

```
Leu Tyr Leu Gln Met Asn Thr Leu Arg Val Asp Asp Thr Ala Val Tyr
                85                  90                  95

Tyr Cys Ala Arg Val Ser Tyr Tyr Gly Arg Gly Trp Tyr Phe Asp Tyr
            100                 105                 110

Trp Gly Gln Gly Thr Thr Leu Thr Val Ser Ser
        115                 120
```

<210> SEQ ID NO 18
<211> LENGTH: 123
<212> TYPE: PRT
<213> ORGANISM: Artificial sequence
<220> FEATURE:
<223> OTHER INFORMATION: Synthetic polypeptide

<400> SEQUENCE: 18

```
Glu Val Gln Val Val Glu Ser Gly Gly Leu Val Gln Pro Gly Arg
1               5                   10                  15

Ser Leu Arg Leu Ser Cys Thr Thr Ser Gly Phe Thr Phe Thr Asp Tyr
                20                  25                  30

Tyr Val Ser Trp Val Arg Gln Ala Pro Gly Lys Ala Leu Glu Trp Leu
            35                  40                  45

Gly Phe Ile Arg Asn Lys Val Asn Gly Tyr Thr Thr Glu Phe Ser Ser
    50                  55                  60

Ser Val Lys Gly Arg Phe Thr Ile Ser Arg Asp Asn Ser Lys Ser Ile
65                  70                  75                  80

Leu Tyr Leu Gln Met Asn Ser Leu Lys Ile Glu Asp Thr Ala Val Tyr
                85                  90                  95

Tyr Cys Ala Arg Val Ser Tyr Tyr Gly Arg Gly Trp Tyr Phe Asp Tyr
            100                 105                 110

Trp Gly Gln Gly Thr Thr Leu Thr Val Ser Ser
        115                 120
```

<210> SEQ ID NO 19
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 19

```
Asp Ile Val Met Thr Gln Ser Thr Ser Ser Leu Ser Ala Ser Leu Gly
1               5                   10                  15

Asp Arg Val Thr Ile Ser Cys Arg Ala Ser Gln Asp Ile Asp Asn Tyr
                20                  25                  30

Leu Ser Trp Phe Gln Gln Lys Pro Asp Gly Thr Val Lys Leu Leu Ile
            35                  40                  45

Tyr Tyr Thr Ser Arg Leu His Ser Gly Val Pro Ser Arg Phe Ser Gly
        50                  55                  60

Ser Gly Ser Gly Thr Asp Tyr Ser Leu Thr Ile Ser Ser Leu Asp Gln
65                  70                  75                  80

Glu Asp Ile Ala Thr Tyr Phe Cys Gln Gln Gly Asn Thr Phe Pro Trp
                85                  90                  95

Thr Phe Gly Gly Gly Thr Lys Leu Glu Ile Lys
            100                 105
```

<210> SEQ ID NO 20
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 20

Asp Ile Val Met Thr Gln Ser Pro Ser Ser Leu Ser Ala Ser Val Gly
1               5                   10                  15

Asp Arg Val Thr Ile Ser Cys Arg Ala Ser Gln Asp Ile Asp Asn Tyr
            20                  25                  30

Leu Ser Trp Phe Gln Gln Lys Pro Gly Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Ile Ala Thr Tyr Phe Cys Gln Gln Gly Asn Thr Phe Pro Trp
                85                  90                  95

Thr Phe Gly Gly Gly Thr Lys Val Glu Ile Lys
            100                 105

<210> SEQ ID NO 21
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 21

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Asp Ile Asp Asn Tyr
            20                  25                  30

Leu Ser Trp Phe Gln Gln Lys Pro Gly Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Ile Ala Thr Tyr Phe Cys Gln Gln Gly Asn Thr Phe Pro Trp
                85                  90                  95

Thr Phe Gly Gly Gly Thr Lys Val Glu Ile Lys
            100                 105

<210> SEQ ID NO 22
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 22

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Asp Ile Asp Asn Tyr
            20                  25                  30

Leu Ser Trp Phe Gln Gln Lys Pro Gly Gly Thr Val Lys Leu Leu Ile
        35                  40                  45

Tyr Tyr Thr Ser Arg Leu His Ser Gly Val Pro Ser Arg Phe Ser Gly
            50                  55                  60

Ser Gly Ser Gly Thr Asp Tyr Thr Leu Thr Ile Ser Ser Leu Gln Pro
65                  70                  75                  80

Glu Asp Ile Ala Thr Tyr Phe Cys Gln Gln Gly Asn Thr Phe Pro Trp
                85                  90                  95

Thr Phe Gly Gly Gly Thr Lys Val Glu Ile Lys
            100                 105

<210> SEQ ID NO 23
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 23

Asp Ile Val Met Thr Gln Ser Pro Ser Ser Leu Ser Ala Ser Val Gly
1               5                   10                  15

Asp Arg Val Thr Ile Ser Cys Arg Ala Ser Gln Asp Ile Asp Asn Tyr
                20                  25                  30

Leu Ser Trp Phe Gln Gln Lys Pro Gly Gly Thr Val Lys Leu Leu Ile
            35                  40                  45

Tyr Tyr Thr Ser Arg Leu His Ser Gly Val Pro Ser Arg Phe Ser Gly
            50                  55                  60

Ser Gly Ser Gly Thr Asp Tyr Thr Leu Thr Ile Ser Ser Leu Gln Pro
65                  70                  75                  80

Glu Asp Ile Ala Thr Tyr Phe Cys Gln Gln Gly Asn Thr Phe Pro Trp
                85                  90                  95

Thr Phe Gly Gly Gly Thr Lys Leu Glu Ile Lys
            100                 105

<210> SEQ ID NO 24
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 24

Asp Ile Val Met Thr Gln Ser Pro Ser Ser Leu Ser Ala Ser Val Gly
1               5                   10                  15

Asp Arg Val Thr Ile Ser Cys Arg Ala Ser Gln Asp Ile Asp Asn Tyr
                20                  25                  30

Leu Ser Trp Phe Gln Gln Lys Pro Gly Gly Thr Val Lys Leu Leu Ile
            35                  40                  45

Tyr Tyr Thr Ser Arg Leu His Ser Gly Val Pro Ser Arg Phe Ser Gly
            50                  55                  60

Ser Gly Ser Gly Thr Asp Tyr Thr Leu Thr Ile Ser Ser Leu Gln Pro
65                  70                  75                  80

Glu Asp Ile Ala Thr Tyr Phe Cys Gln Gln Gly Asn Thr Phe Pro Trp
                85                  90                  95

Thr Phe Gly Gly Gly Thr Lys Leu Glu Ile Lys
            100                 105